United States Patent [19]
Scheinberg

[11] Patent Number: 6,007,814
[45] Date of Patent: *Dec. 28, 1999

[54] THERAPEUTIC USES OF THE HYPERVARIABLE REGION OF MONOCLONAL ANTIBODY M195 AND CONSTRUCTS THEREOF

[75] Inventor: David A. Scheinberg, New York, N.Y.

[73] Assignee: Sloan-Kettering Institute for Cancer Research, New York, N.Y.

[ * ] Notice: This patent is subject to a terminal disclaimer.

[21] Appl. No.: 07/861,967

[22] Filed: Jun. 15, 1992

Related U.S. Application Data

[63] Continuation-in-part of application No. 07/450,918, filed as application No. PCT/US90/07436, Dec. 14, 1990.

[51] Int. Cl.[6] ........................... C07K 16/28; C07K 16/46; A61K 39/395
[52] U.S. Cl. .................................... 424/130.1; 424/133.1; 424/152.1; 424/153.1; 424/155.1; 424/173.1; 424/178.1; 424/183.1; 530/387.3; 530/387.7; 530/388.2; 530/388.7; 530/388.6; 530/388.8; 530/389.6; 530/389.7; 530/391.3; 530/391.7
[58] Field of Search .............................. 530/387.3, 387.7, 530/387.73, 387.75, 388, 8, 391.7, 391.3, 388.2, 388.7, 389.6, 389.7; 435/240.27, 72.2, 70.21; 424/134.1, 138.1, 153.1–156.1, 130.1, 133.1, 152.1, 173.1, 178.1, 183.1

[56] References Cited

U.S. PATENT DOCUMENTS 5,225,539 7/1993 Winter .

*Primary Examiner*—Toni R. Scheiner
*Assistant Examiner*—Nancy A. Johnson
*Attorney, Agent, or Firm*—John P. White; Cooper & Dunham LLP

[57] ABSTRACT

Therapeutic agents and methods for treating and diagnosing leukemia are provided. Such agents comprises monoclonal antibody M195, a polypeptide capable of binding to the antigen of M195, or a chimeric antibody such a peptide, conjugated to a cytotoxic agent, e.g. a radioisotope or alone. Methods for delivering genetic information to a targeted cell is also provided.

31 Claims, 27 Drawing Sheets

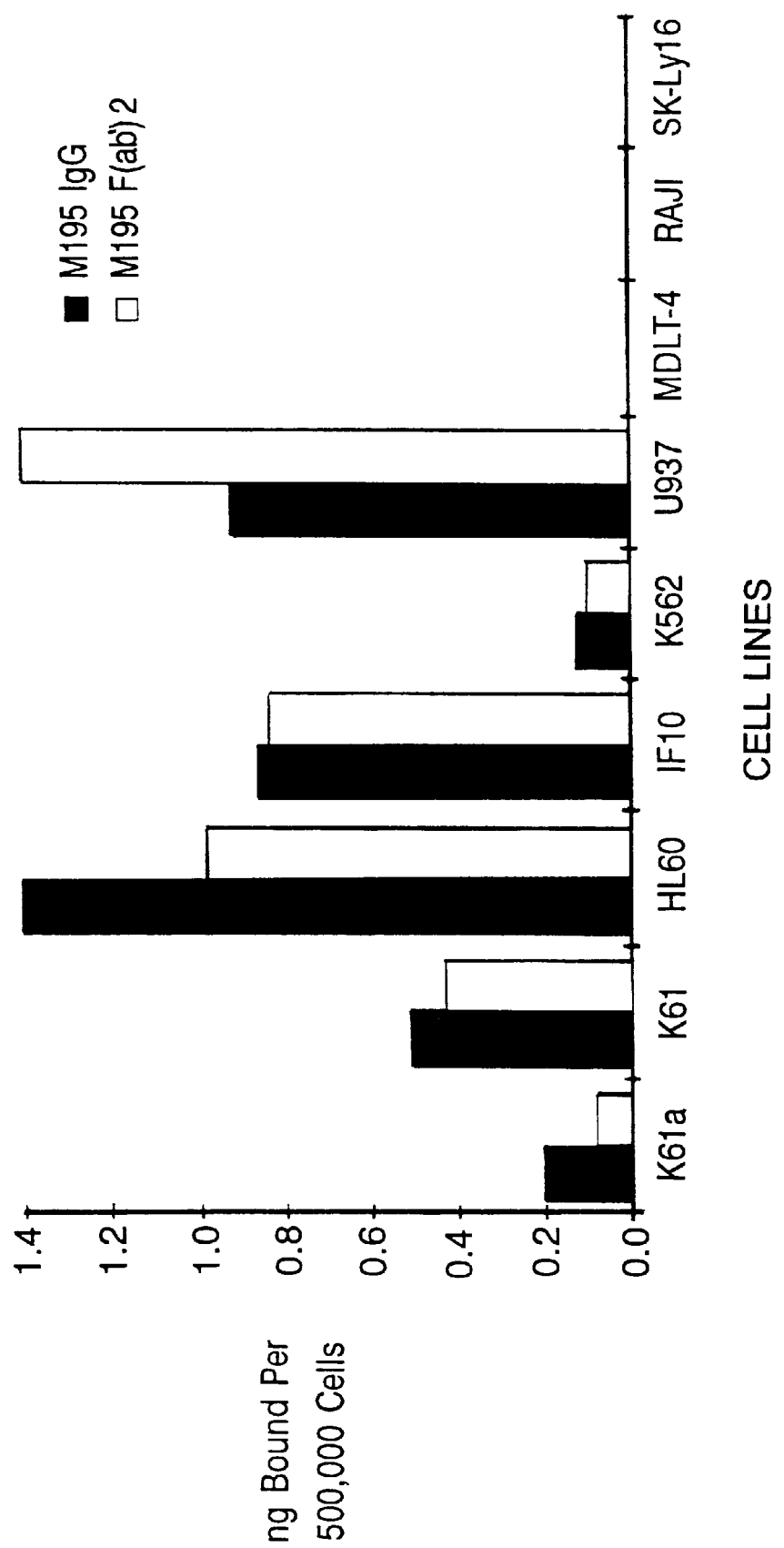

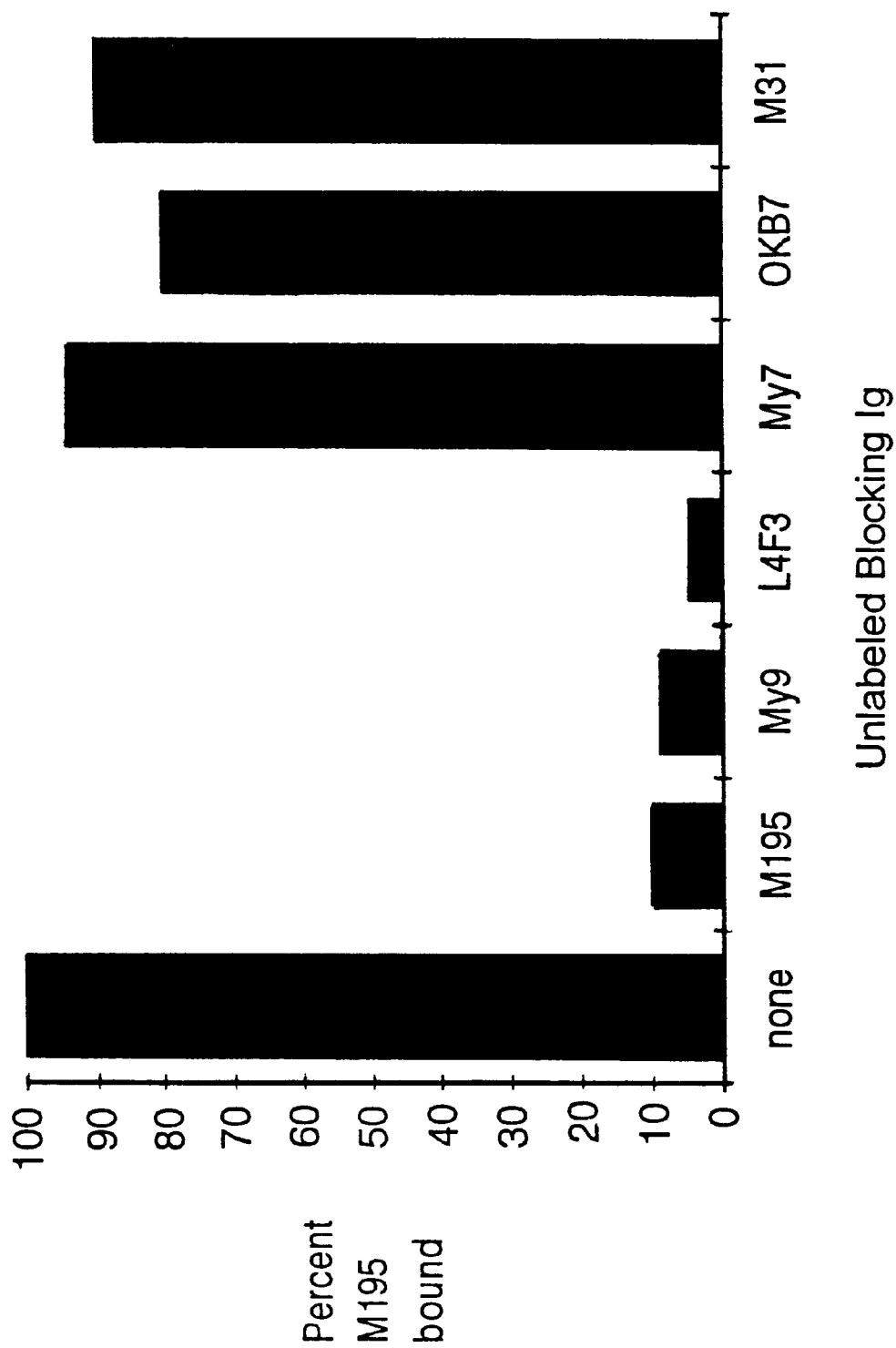

In-111 M195 Internalization

I-125 M195 F(ab')2 Internalization

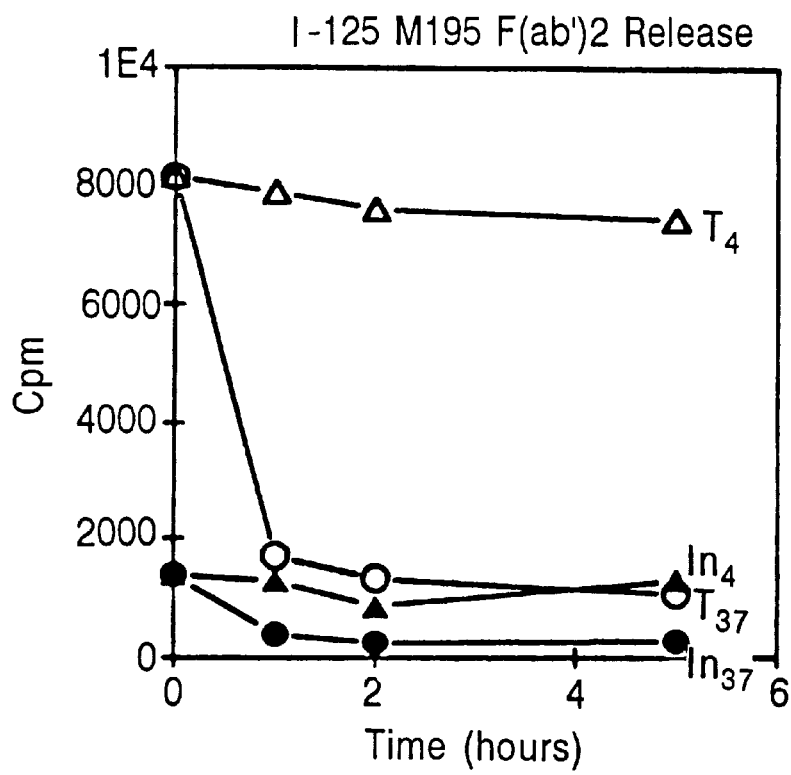
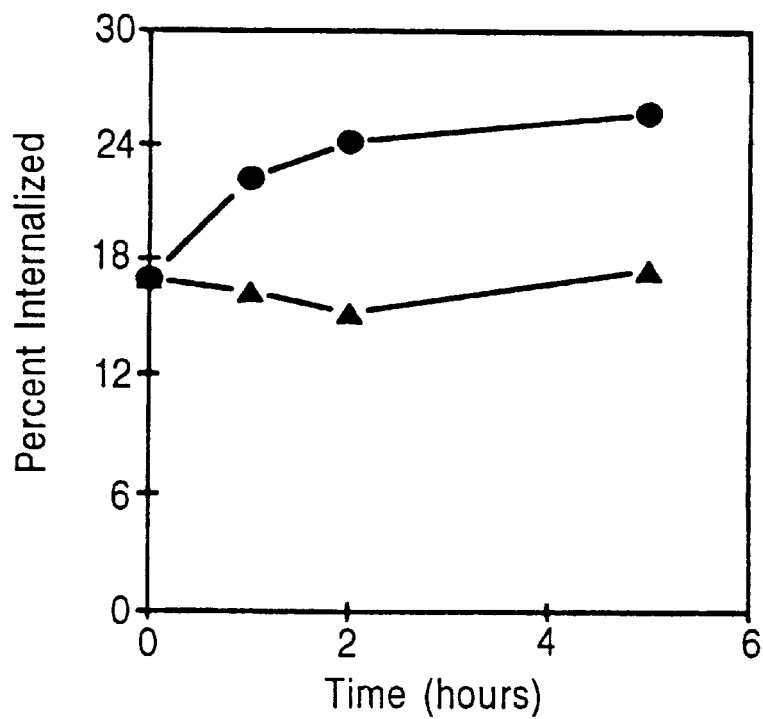

Expression of The M195 Antigen

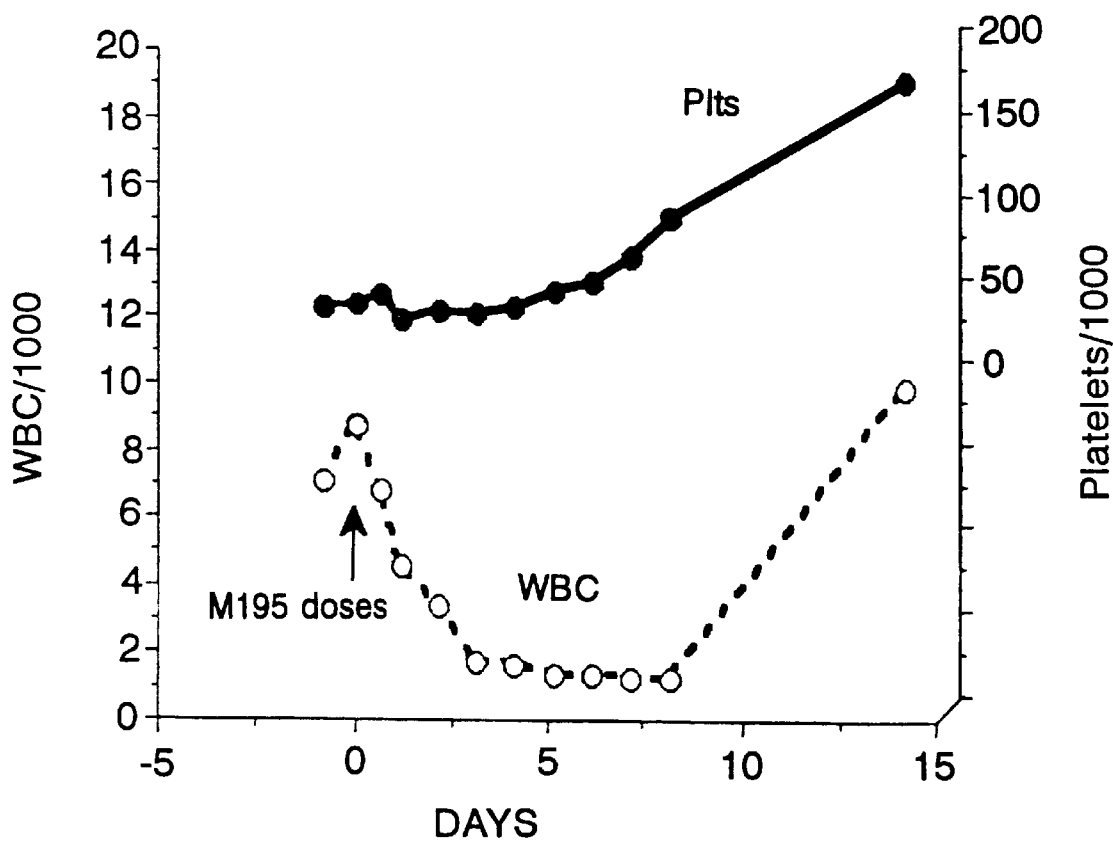

Retroviral vector — mouse monoclonal anti-retroviral coat protein

Step 1:
Bind and wash

Step 2:
Add rabbit anti-mouse and wash

Step 3:
Add M195 and wash

Step 4:
Allow targeted retroviral vector to specifically bind to progenitor cells followed by internalization (next figure)

a  M195 or contruct
b  retroviral vector
c  envelope with protein and lipid
d  genetic information

THERAPEUTIC USES OF THE HYPERVARIABLE REGION OF MONOCLONAL ANTIBODY M195 AND CONSTRUCTS THEREOF

This application is a 371 of PCT/U.S.90/07436 filed Dec. 14, 1990 which is a continuation-in-part of U.S. Ser. No. 07/450,918, filed Dec. 14, 1989, now abandoned, the contents of which are hereby incorporated by reference into the present application.

Throughout this application various publications are referenced by numbers within parentheses. Full citations for these publications may be found at the end of the specification immediately preceding the claims. The disclosure of these publications, in their entireties, are hereby incorporated by reference into this application in order to more fully describe the state of the art to which this invention pertains.

BACKGROUND OF THE INVENTION

MONOCLONAL ANTIBODY M195. Mouse monoclonal antibody M195 is an IgG2a (1, 2) which reacts with 60–70% of samples of leukemia cells from patients with acute myelogenous leukemia (AML). M195 also binds to early myeloid cells (CFU-GM) and some monocytes but not to the earliest myeloid progenitors. The target antigen is not expressed on any other hematopoietic or non-hematopoietic tissue. Antibodies to a related antigen on the same protein (CD33), My9 and L4F3, are currently being used to purge bone marrow of ANLL before autologous transfusion (3, 4). M195 is rapidly internalized into cells after binding and this effect can enhance delivery of radiometals, radioiodine or conjugated toxins into cells (5). M195 is able to kill leukemia cells with rabbit or guinea pig complement, but not by use of human complement or human antibody-dependent cellular cytotoxicity in vitro. Activation of these mediators in vitro has correlated with these effects in vivo (6), but it is not known if the lack of in vitro effects will predict lack of in vivo effects. Because M195 also reacts with early myeloid cells, normal marrow progenitors may be affected also.

MYELOID LEUKEMIAS. Long-term survival for patients with acute leukemia given the best current chemotherapeutic regimens is generally less than 20% (7). Survival of patients who relapse or who fail first attempts at induction chemotherapy is far lower. Autologous or allogeneic bone marrow transplantation may improve survival, but only in a small subset of patients (8). There are no effective therapies for myelodysplastic syndromes or chronic monocytic leukemias and long term survival in these diseases is rare. Among patients with chronic myeloid leukemias (CML), only allogeneic bone marrow transplant has had an impact on survival (9). An approach to therapy which may be more effective is the use of monoclonal antibodies.

MONOCLONAL ANTIBODIES TO MYELOID ANTIGENS. Monoclonal antibodies (mAb) reactive with differentiation antigens present on myeloid cells and their progenitors are being used to study hematopoietic differentiation, to identify acute nonlymphoid leukemia (ANLL), to study the effects of hematopoietic growth factors, to purge bone marrow of leukemia cells, and for therapy in vivo (10–24).

The antigens displayed on the surface of acute nonlymphocytic leukemia (ANLL) cells and hematopoietic progenitor cells are being mapped in a number of laboratories using monoclonal antibodies (mAbs)(25).

These studies have been directed at identifying antigens that are useful in distinguishing lymphoid from nonlymphoid leukemias (26–28), in subtyping of acute myelogenous leukemia, and in predicting outcome (29–34) and in therapy in vivo (35) or via bone marrow purging ex vivo (36). Antigens defining ANLL cells also identify normal hematopoietic cells during early stages of their development and thus should be classified as differentiation antigens rather than leukemia specific antigens.

Antigens restricted to the earliest stages of hematopoietic development are of particular interest since ANLL is thought to be derived from these cells (37–40). Monoclonal antibodies identifying these early cells can help in their purification or the study of growth regulation and control of differentiation (41). Such early progenitors may be useful for autologous reinfusion in bone marrow rescue (42). Studies of bone marrow from patients with ANLL have shown that the clonogenic cells are probably derived from a subset of cells which are phenotypically more immature that the majority of cells in circulation (38, 39). This suggests that analysis of the development of leukemia cells, as well as therapeutic trials, should also be directed at these early cells and not simply the phenotypically predominant cells in the marrow and peripheral blood.

Several mAbs restricted to hematopoietic progenitors have been described: MY10, 3C5, and 12.8 recognize a 115-kDa glycoprotein (gp115 [CD34]) found on normal colony forming cells, myeloblasts, and leukemic blasts from most patients with ANLL and acute lymphoid leukemias (42–44). Monoclonal anitbody NHL-30.5 identifies a 180-kDa protein found on a similar distribution of cells (45–46). The My9 and L4F3 antibodies identify a 67-kDa glycoprotein (CD33) (48–50) which is expressed on slightly more mature progenitors (subsets of CFU-GEMM and some older cells) and is restricted to leukemias of the myeloid and monocytic lineage. Long-term culture studies suggest that elimination of cells bearing the CD33 antigen will still allow regrowth of normal marrow cells of all lineages, presumably because of the presence of more immature antigen negative progenitors (48). Sabbath et al. (39) show that the CD33 antigen is expressed on leukemic colony-forming cells whereas other more mature markers are less commonly expressed. Finally, studies with ANLL marrow suggest it may be possible to purge leukemia cells from the bone marrow of many patients with ANLL using complement fixing antibodies to CD33 without destroying the ultimate normal progenitors (47). Several other antibodies with a less restricted distribution have also been described (38, 51, 52).

RADIOLABED ANTIBODIES. Since the discovery of hybridoma technology by Kohler and Milstein (53), there has been considerable interest in the utility of monoclonal antibodies as carriers of radioactivity for the diagnosis and therapy of cancer (54, 55). After the initial report by Goldenberg et al. on the utility of radiolabeled antibodies in the detection of cancer (56), there have been several clinical trials utilizing radiolabeled monoclonal antibodies in lymphoma and leukemia (57–63), both for radioimmunolocalization and radioimmunotherapy. Most of these trials have employed radioiodine (57–62); Carrasquillo and associates have also studied $^{111}$In-labeled monoclonal antibody T101 (57, 61) in the diagnosis of T-cell lymphoma. One obvious advantage of radiolabeled antibodies is that the specificity of antibody for the target antigen, often expressed in increased quantities on neoplastic cells, offers a potentially useful method for the selective delivery of radioactivity to the tumor site; moreover, the range of potentially lethal radiation emitted by most currently used radionuclides extends over several cell diameters, making it theoretically possible for the radiation to be cytotoxic to neighboring neoplastic cells that lack the target antigen.

Historically, beta-minus particle emitters such as $^{131}$I have been preferred for mAb directed radioimmunotherapy. Radionuclides such as $^{125}$I that decay by electron capture are also of interest in radioimmunotherapy because they are cytotoxic when internalized by the cell (64). $^{125}$I labeled antibodies that are internalized into the cell following interaction with the target antigen may thus be cytotoxic (65). Studies in both animals and humans have shown that the radiometal $^{111}$In concentrates to a significantly greater extent in tumor compared to radioiodine (66, 69). Thus, use of beta-minus emitting radiometals such as $^{90}$Y are of interest for therapy as well. Therefore, the choice of radionuclide used to label monoclonal antibodies may be of importance in the design of clinical trials utilizing radiolabeled mAbs for diagnosis and therapy.

INTERNALIZATION OF MONOCLONAL ANTIBODIES. Antigen-antibody complexes may either be shed from the cell or internalized into the cell following interaction with antibody. This process, known as modulation, was first described in mice (70) and later confirmed to occur during trials of mAb in humans (71). The process appears to be a general phenomenon found in many antigen-antibody systems of hematopoietic cells (72) and neoplasms as well as in solid tumors (73). Modulation may result in mAb shedding, internalization, or both processes. Shedding may result in residence time of the antibody on the target cell too short to achieve cell kill. On the other hand, internalized antigen-antibody complexes may theoretically deliver significant amounts of cytotoxic antibody into the cell if the cytotoxic label attached to the antibody is internalized into the cell and retained.

The cell biology of modulation and receptor internalization has been studied elsewhere (74, 75).

MONOCLONAL ANTIBODY THERAPY OF LEUKEMIA. Monoclonal antibody based therapies are ideally applicable to the hematopoietic neoplasms because of readily accessible neoplastic cells in the blood, marrow, spleen and lymph nodes which allow rapid and efficient targeting of specific mAb. The well characterized immunophenotypes of the various lineages and stages of hematopoietic differentiation should enable identification of antigen targets for selective binding of mAb to neoplastic cells while sparing other necessary hematopoietic lineages and progenitor cells.

In some models of leukemia, specific uptake of antibodies onto target cells can be demonstrated within minutes, followed by losses of mAb from the cells by modulation (76–79). Similar modulation has been seen in pilot studies in acute leukemia in humans (80, 81). Based on this biology and pharmacokinetics, it has been proposed that mAb tagged with short-lived nuclides emitting short-ranged, high linear energy transfer (LET) alpha particles (79) or short-ranged auger electrons (82, 83) may be effective in therapy.

A challenge in treating AML with mAb is the necessity for selection of an antigen target found on clonogenic myeloid leukemia blasts, but not on the ultimate normal hematopoietic progenitors. Gp67 (CD33) appears to be one such target. Cytotoxic murine mAb to this target can selectively kill early myeloid cells (CFU-GM, BFU-E) and leukemia cells without eliminating the potential for regrowth of normal bone marrow progenitors. This selectivity has been applied to the purging of bone marrow before autologous reinfusion in the treatment of AML (84–91). M195 is a mouse IgG2a reactive with gp67 which is capable of rapidly internalizing into target cells upon binding, but is unable to kill cells in vitro by use of human complement or effector cells (88, 89). Other than committed hematopoietic progenitor cells and some monocytes, M195 does not appear to react with any normal cells or tissues (26, 27).

Previously all of the antibody therapy work done had used the mouse monoclonal antibody. This approach has certain limitations. The mouse antibody has limited biological activity for killing cells, and it has a relatively short half life in human serum. Additionally because the antibody used is derived from a mouse it can trigger an immune response to the foreign material. Thus use of a humanized antibody helps to improve the therapeutic attributes of the molecule. It improves half life of the molecule in human serum and reduces the immune response.

GENETIC THERAPY. A new powerful tool to introduce genes into mammalian cells is the construction of recombinant retroviral vectors in which exogenous genes replace portions of the viral genome (95). However, some constraints may limit the use of retroviral vectors. One concerns cell tropism: this limitation has been in part circumvented by the development of amphotropic viral vectors, able to infect a wide range of cells from different species. On the contrary, it may be advantageous for particular purposes, including gene therapy, to infect only a chosen suppopulation of cells. This is not possible with either ecotropic or amphotropic viruses if the whole cell population bears membrane receptors for the virus. One method to allow selective targeting of specific cells within a mixture is the use of specific antigenic targets. The development of a technology that would allow us to introduce a recombinant retrovirus into selected cells is a way to considerably extend the potentiality of retroviral vectors.

SUMMARY OF THE INVENTION

This invention provides a polypeptide which consists essentially of an amino acid sequence capable of specifically binding to the antigen which monoclonal antibody M195 (ATCC No. HB 10306) binds, for example, a polypeptide whose amino acid sequence is the same or substantially the same as the amino acid sequence of the hypervariable region of monoclonal antibody M195.

The invention further provides a chimeric antibody which comprises such a polypeptide, that is, an amino acid sequence consisting essentially of the amino acids necessary to bind to the antigen to which M195 binds.

Still further, this invention provides a therapeutic agent comprising such a polypeptide, chimeric antibody, or the M195 anitibody per se to any of which a cytotoxic agent, for example, a radioisotope or a toxin is conjugated.

The invention further provides pharmaceutical compositions which comprise such a chimeric antibody or therapeutic agent, or M195 per se.

Finally, this invention additionally provides methods of treating or diagnosing leukemia in human patients; of effecting bone marrow transplants; and of introducing genetic information into hematopoietic cells.

BRIEF DESCRIPTION OF THE FIGURES

FIG. 1A, Total (◊), nonspecific (binding of $^{125}$I-IgG in the presence of excess unlabeled IgG (♦), and specific (■) binding of M195 IgG to HL60 leukemia cells, FIG. 1B, Scatchard plot of M195 IgG binding. FIG. 1C, Scatchard plot of M195 F(Ab)'2 binding.

FIG. 2. Radioimmunoassay of M195 IgG and F(Ab)'2 on cell lines of hematopoietic origin. $^{125}$I-M195 binding was determined at saturation as described in Materials and Methods. Nonspecific binding was 0.2 ng 500,000 cells. Only specific binding is shown: IgG, ■; F(Ab)'2, ▨.

FIG. 6. Blocking of M195 direct radioimmunoassay by excess unlabeled Ig. A 50–100 fold molar excess of the antibodies designated along the X axis were added to HL60 target cells followed by $^{125}$I-M195 at 4° C. for 60 min. The amount of bound $^{125}$I-M195 is shown on the Y axis. Binding of M195 without competing IG was normalized to 100%

Figure 7A:
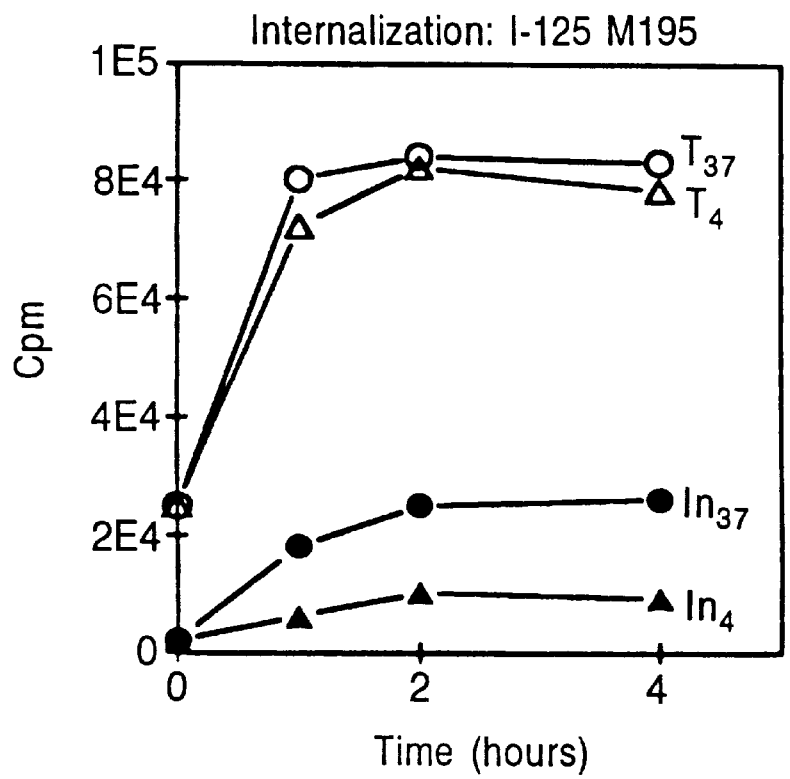
FIGS. 7A–7D. $^{125}$I-M195 Internalization & Release.
Figure 7B:
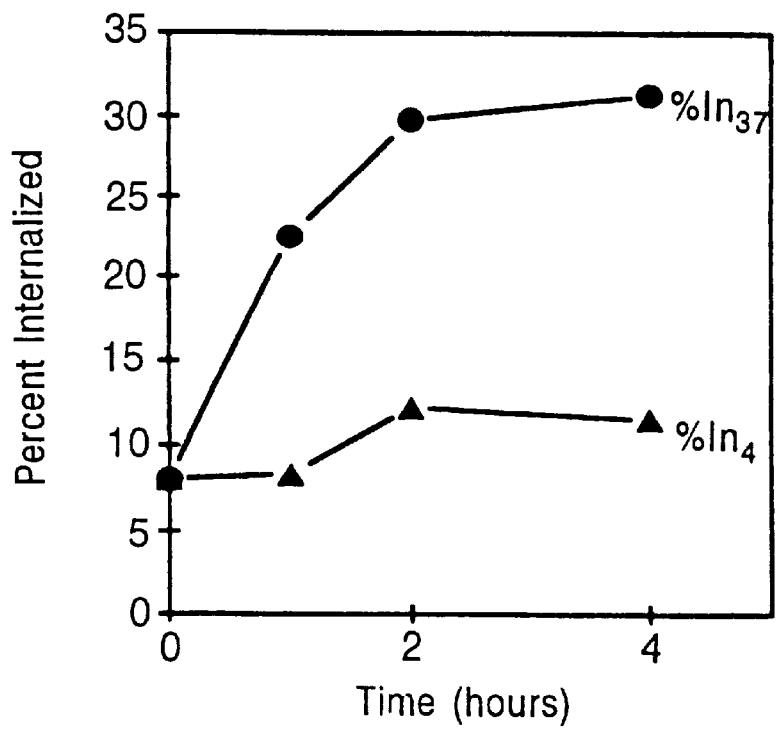

Internalization (FIGS. 7A, 7B): 5 million HL60 cells were mixed with 5 μg mAb or fragment and incubated at 4° or 37°. Aliquots were taken at appropriate time points and measured for total and internalized cell-associated radioactivity.

All graphs showing radioactivity in counts per minute over time are labeled as follows: (△—△): total cell-associated radioactivity at 4° C.; (○—○): total cell-associated radioactivity at 37° C.; (▲—▲): internalized radioactivity at 4° C.; (●—●) internalized radioactivity at 37° C.

All graphs showing percent internalized radioactivity are labeled as follows (▲—▲): percent internalized at 4° C.; (○—○); percent internalized radioactivity at 37° C.

Figure 7C:
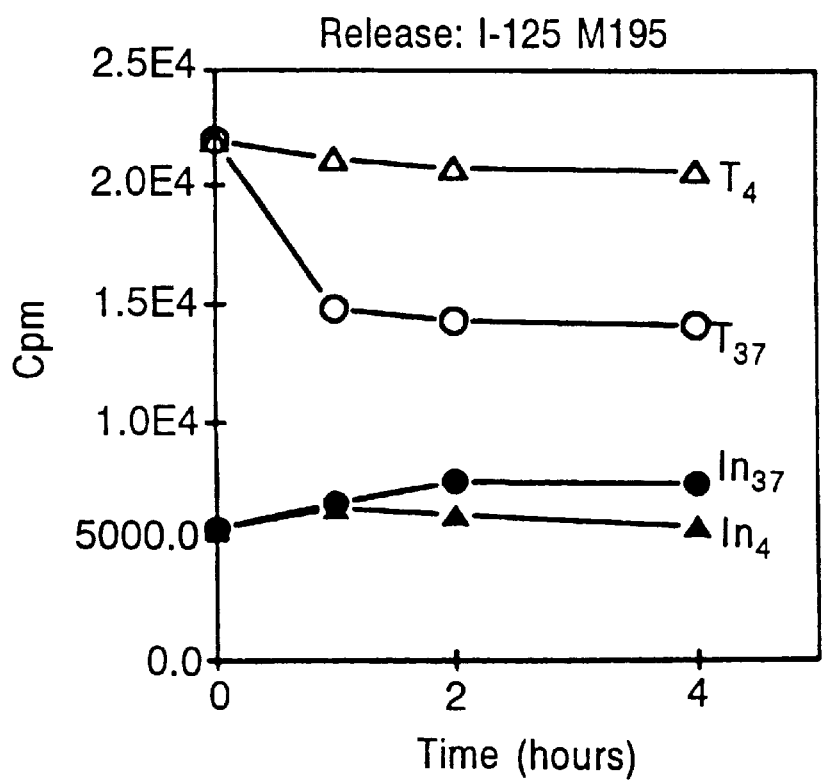
Figure 7D:
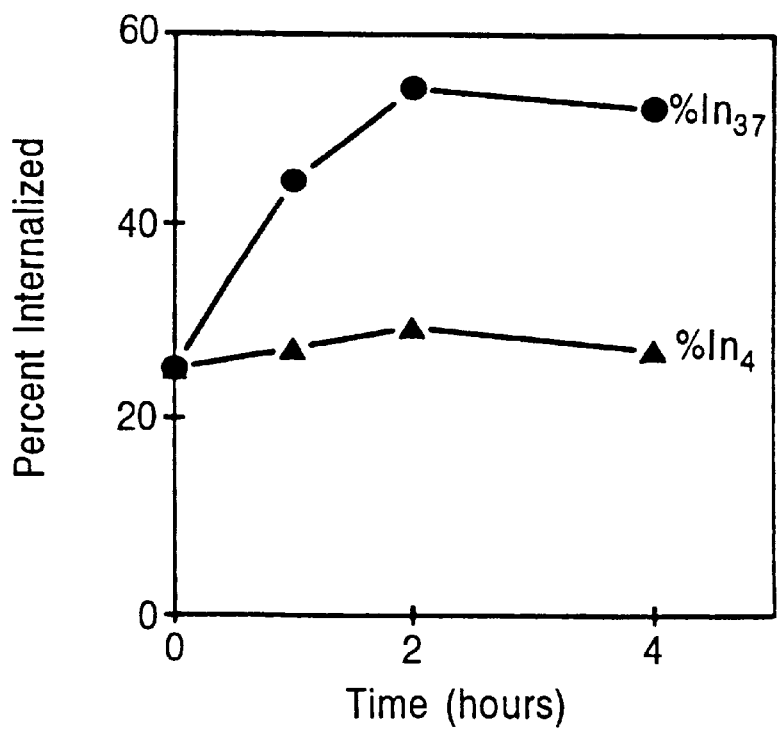

Release (FIGS. 7C, 7D): 5 million cells were incubated with 5 μg mAb or fragment at 4° for 60 minutes, then washed free of ambient mAb. Measurements of internalized radioactivity were carried out as described above with the washed cells being kept at 4° or 37°. The symbols for these graphs are as for internalization data.

FIGS. 8A–8D. $^{111}$In-M195 Internalization & Release.

Internalization (FIGS. 8A, 8D): Conducted exactly as described in FIGS. 8a, 8b except M195 is now labeled with In-111.

Release (FIGS. 8C, 8D): Conducted exactly as described in FIGS. 7c, d except M195 is now labeled in this experiment with In-111.

FIGS. 9A–9D. $^{125}$I-M195 F(ab')2 Internalization & Release.

Internalization (FIGS. 9A, 9B): Conducted exactly as described in FIGS. 8A, 8B except I-125 is now attached to F(ab')$_2$ fragment of M195.

Release (FIGS. 9C, 9D): Conducted as described in FIGS. 7C, 7D except M195 F(ab')$_2$ is now labeled with I-125.

Figure 10:
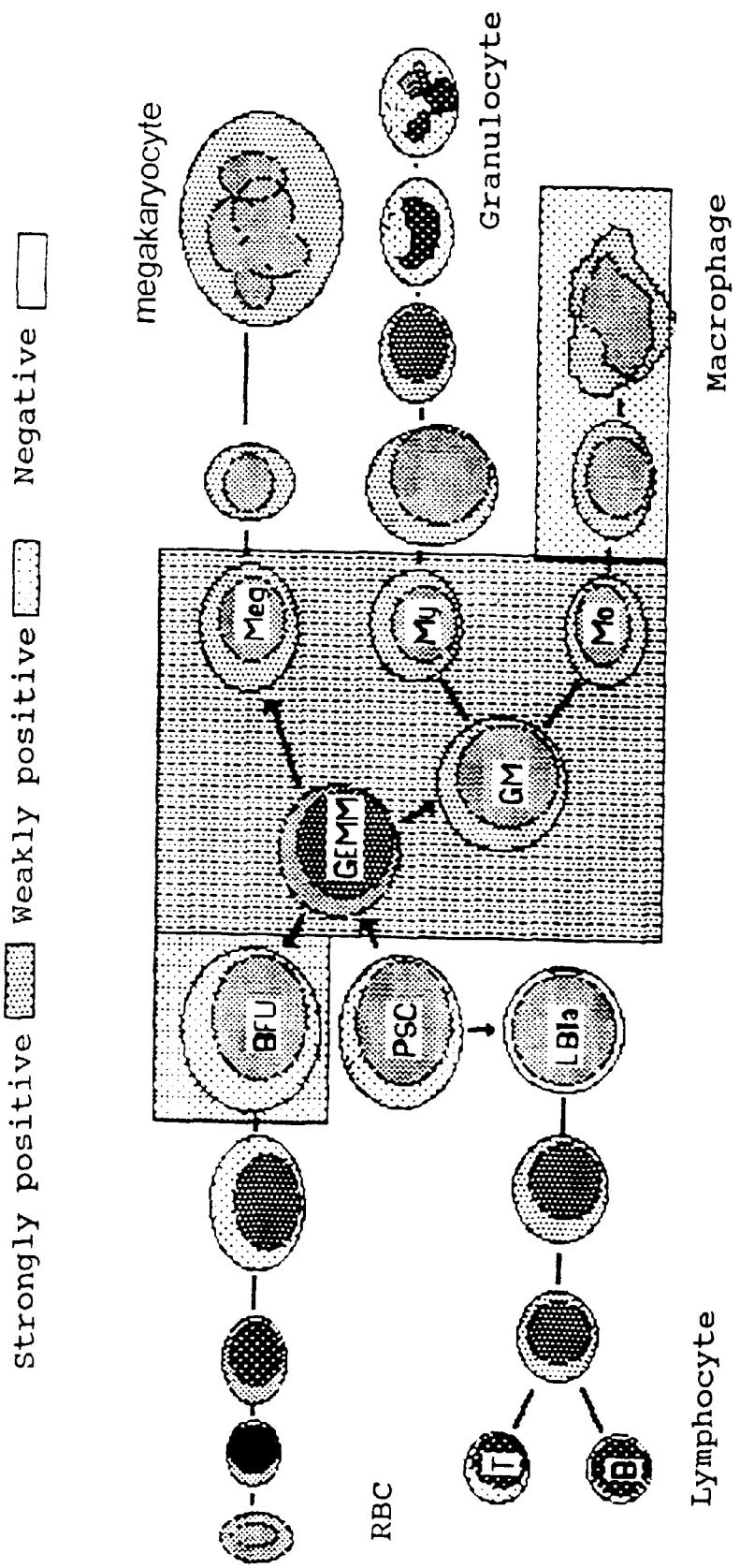

FIG. 10. Schematic diagram of the distribution of the M195 antigen in human tissues. The antigen is not known to be present on any adult non-hematopoietic tissues, so they are not shown. The distribution in the hematopoietic cells is shown.

Figures 11A, 11B:

FIGS. 11A–11B. Posterior and anterior whole body gamma camera images of patient #1, injected 18 hours earlier with 5 mCi iodine-131 M195 (1.5 mg). All known areas of leukemic involvement (bone marrow, spleen, liver, mediastinal chloroma) show marked uptake of M195.

FIGS. 12A–12F. Posterior and anterior images at 24 hrs. of patients injected with $^{131}$I-M195. Bone marrow, liver, and spleen are image.

Figure 13A:
Figure 13B:
Figure 13C:

FIGS. 13A–13C. A comparison of $^{131}$I-M195 imaging (FIG. 13A) with $^{99}$TC-Bone marrow imaging at low (FIG. 1B) or high (FIG. 1C) exposure.

Figure 14:
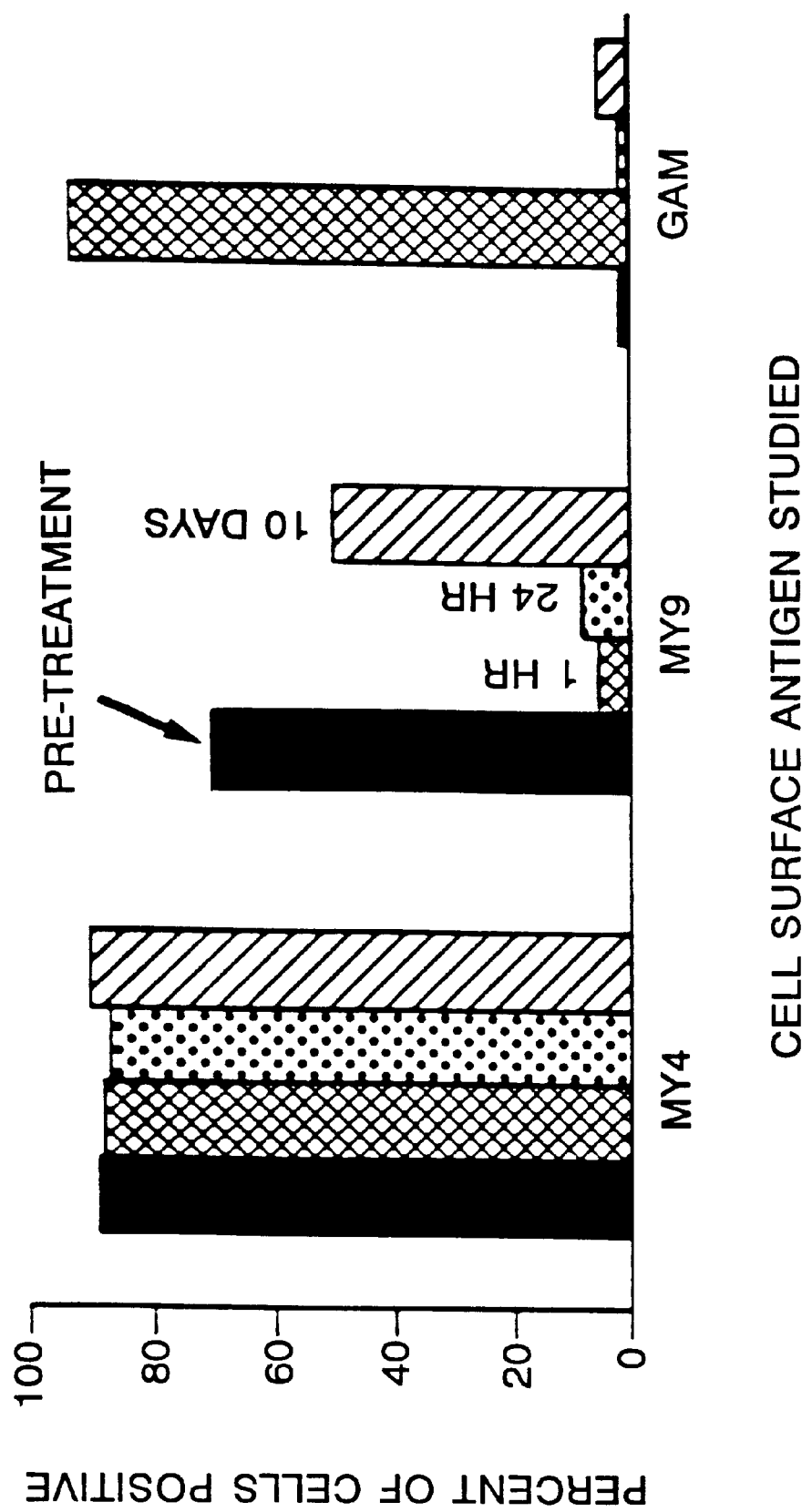

FIG. 14. Modulation of M195 in vivo on leukemia cells in humans as determined by serial flow cytometry at pretreatment and 1 hr, 24 hrs, and 10 days.

Figure 15A:
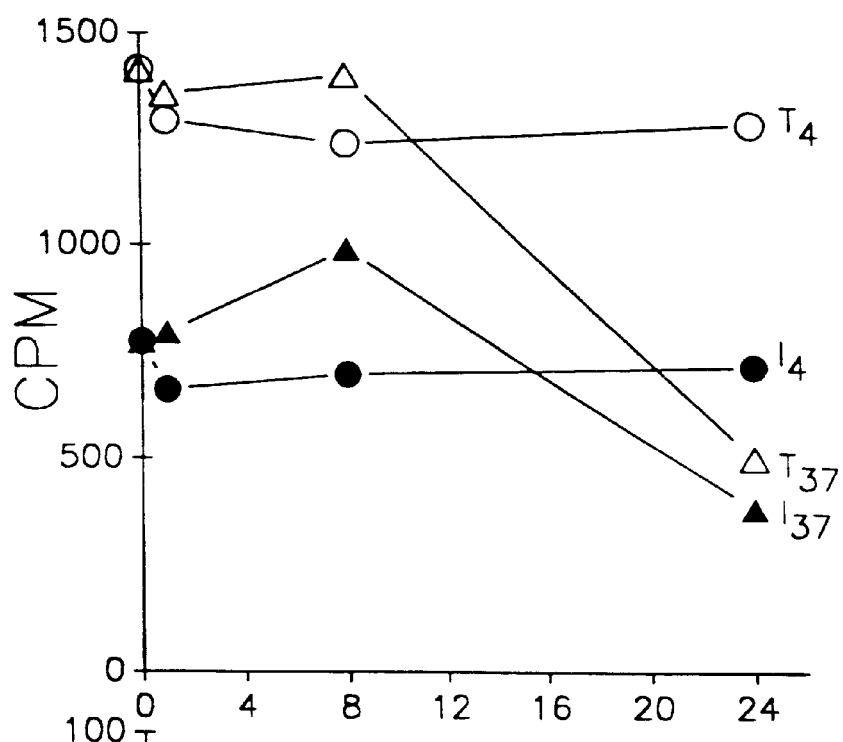
Figure 15B:
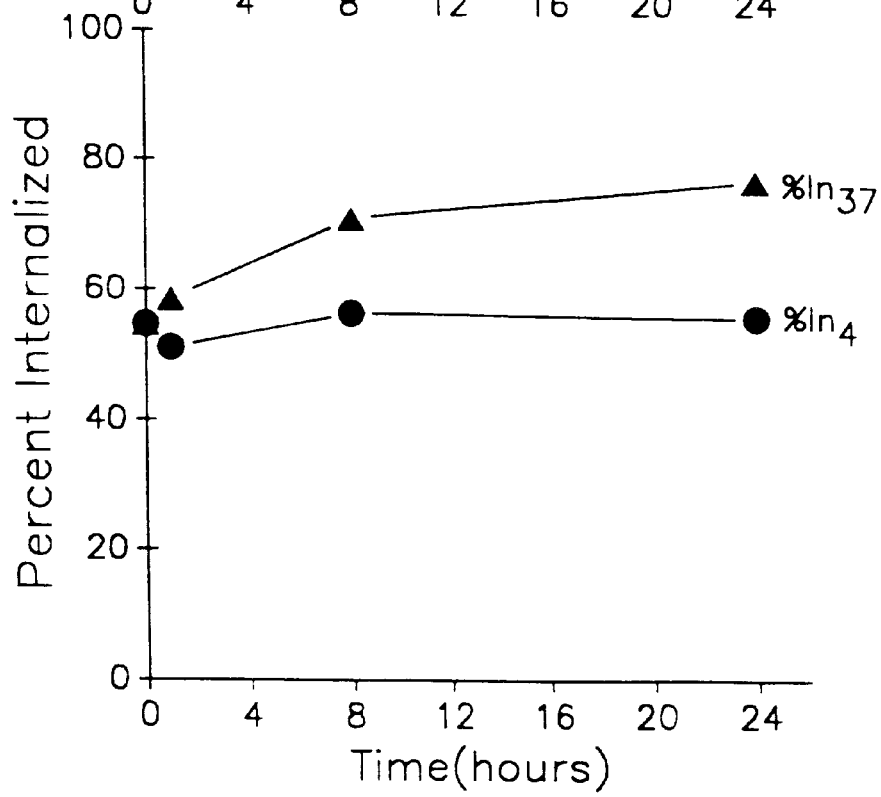

FIGS. 15A–15B. Internalization of M195 into leukemia cells Ex Vivo after injection in vivo into a human patient. FIG. 15A is absolute cpm-FIG. 15B is percentage internalized. 37 is 37°. 4 is 4°. T is total cpm. I is "internalized."

Figure 16:
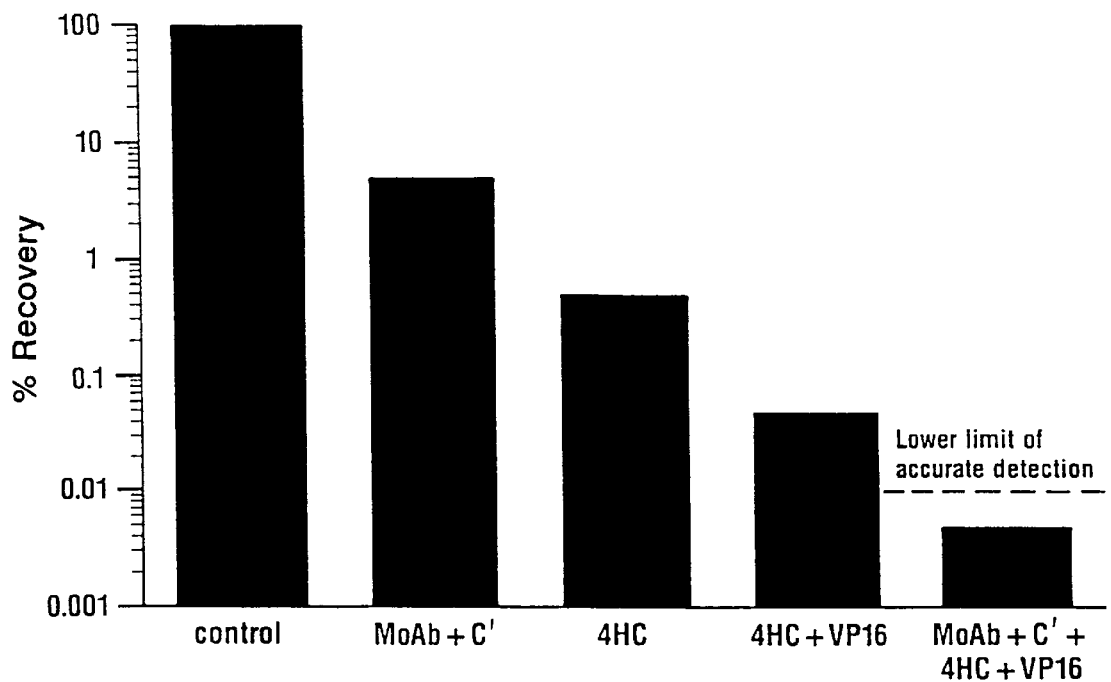

FIG. 16. Cytotoxic activity of four protocols on HL-60 cell line. MoAb+C treatment represents one cycle of 40 μg/ml of M195 and F23 with complement at 1/6(v/v) dilution. 4HC concentration is 100 μM when used alone. 80 μM or 100 μM of 4HC gave the same result when the drug was combined to VP-16 with and without MoAbs.

Figure 17:
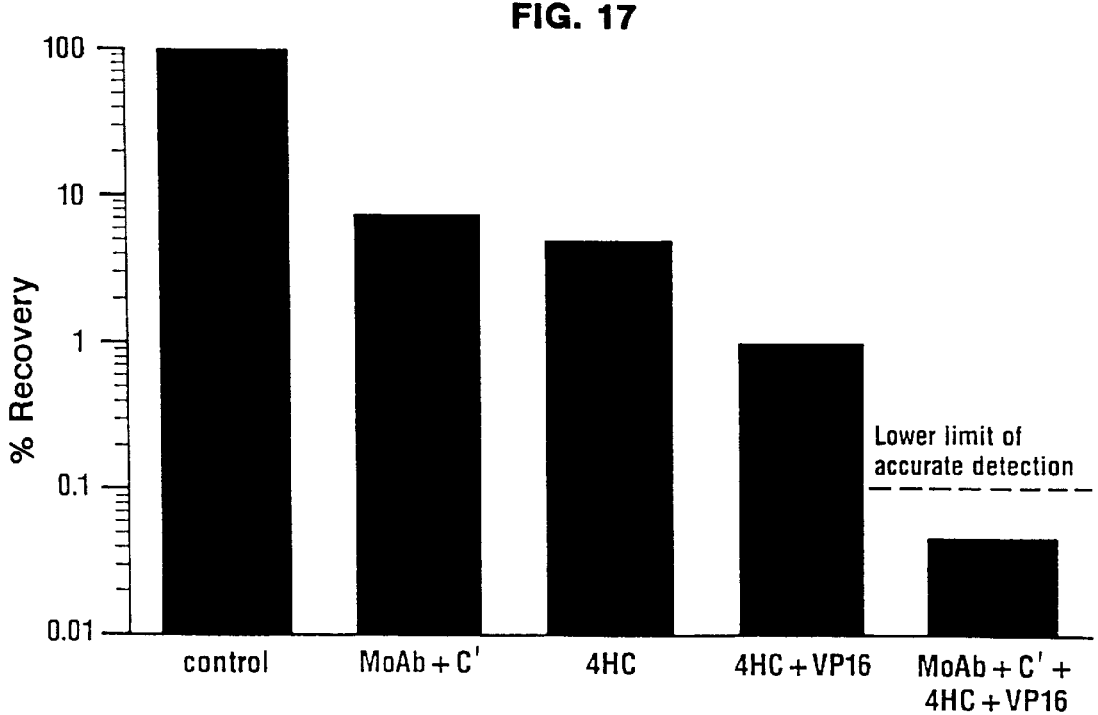

FIG. 17. Cytotoxic activity of four protocols on CFU-L. For details see Legend to FIG. 1.

Figure 18:
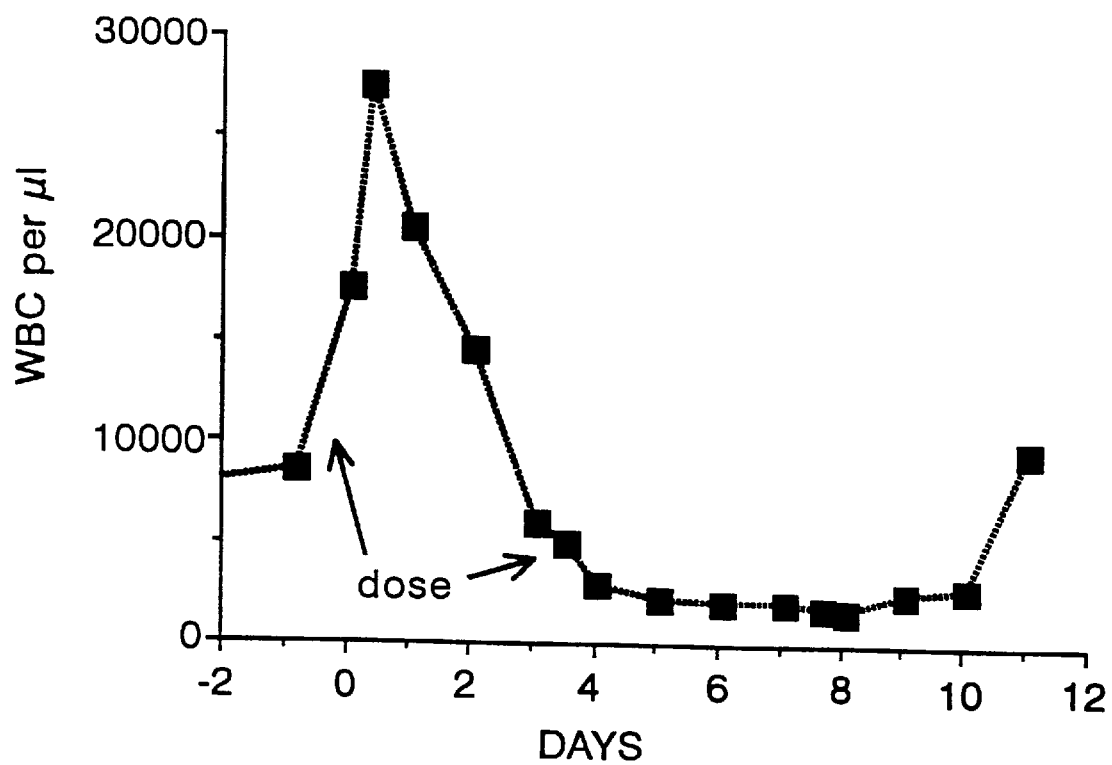

FIG. 18. Peripheral blood leukemia cell counts after 2 doses of $^{131}$I-M195 in patient #1.

FIG. 19. Peripheral white blood cell and platelet counts in patient #7. Patient 7 had relapsed AML after chemotherapy with falling platelets. Following treatment with M195 (90 mCi/M) platelets immediately began to rise despite the killing of blasts in the blood and marrow. On day 7 bone marrow blast had been reduced by 50% and platelets had increased by 50%. There was no toxicity and the patient was discharged. This demonstrates the selective killing by 131-I-M195.

Figure 20A:
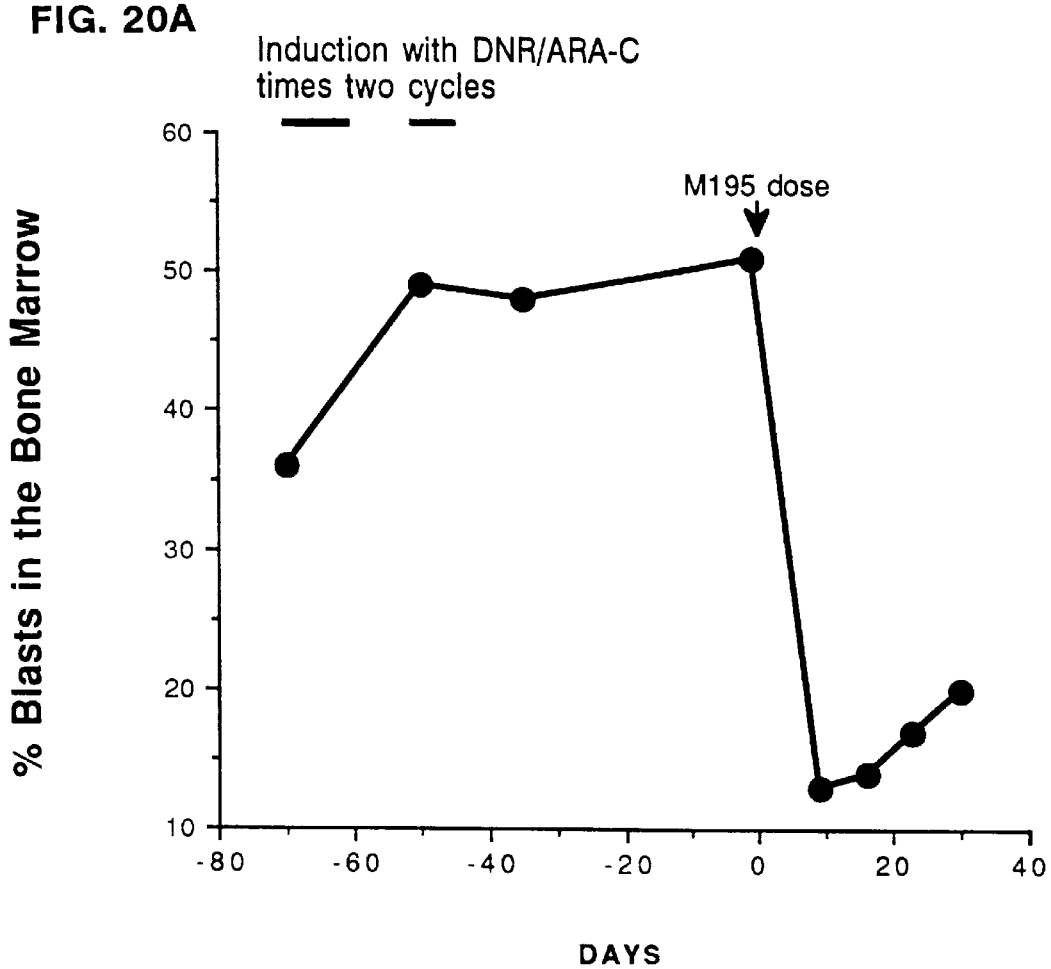
Figure 20B:
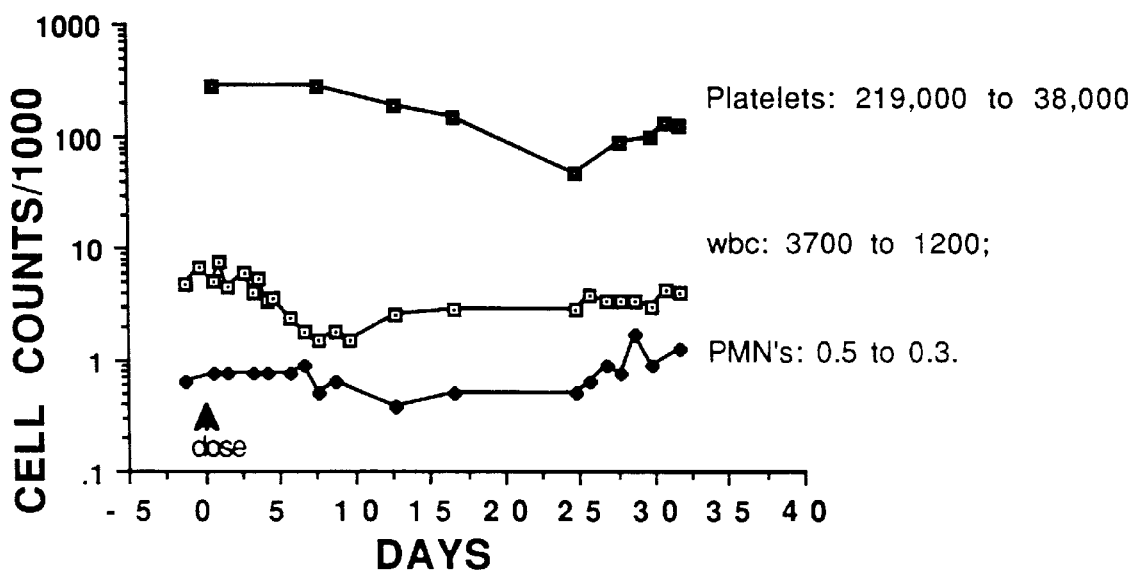

FIGS. 20A–20B Bone marrow blasts (A) peripheral blood cell counts (B) in patient #5. Patient #5 had a myelodysplastic syndrome which evolved into acute myelogenous leukemia. Despite 2 cycles of the best available chemotherapy (Daunomycin and ARA-C for 5 days each time) her bone marrow blast counts continued to rise. One cycle of 131-I-M195 (70 mCi/M) cytoreduced her leukemia and dropped her blast counts in the marrow to 13%. (see above) Effects on her normal cells were present, but tolerable. (see below) Therefore, M195 is effective in refractory, pretreated patients and is relatively selective in cell kill. About 500, 000,000,000 cells were killed.

Figure 21:
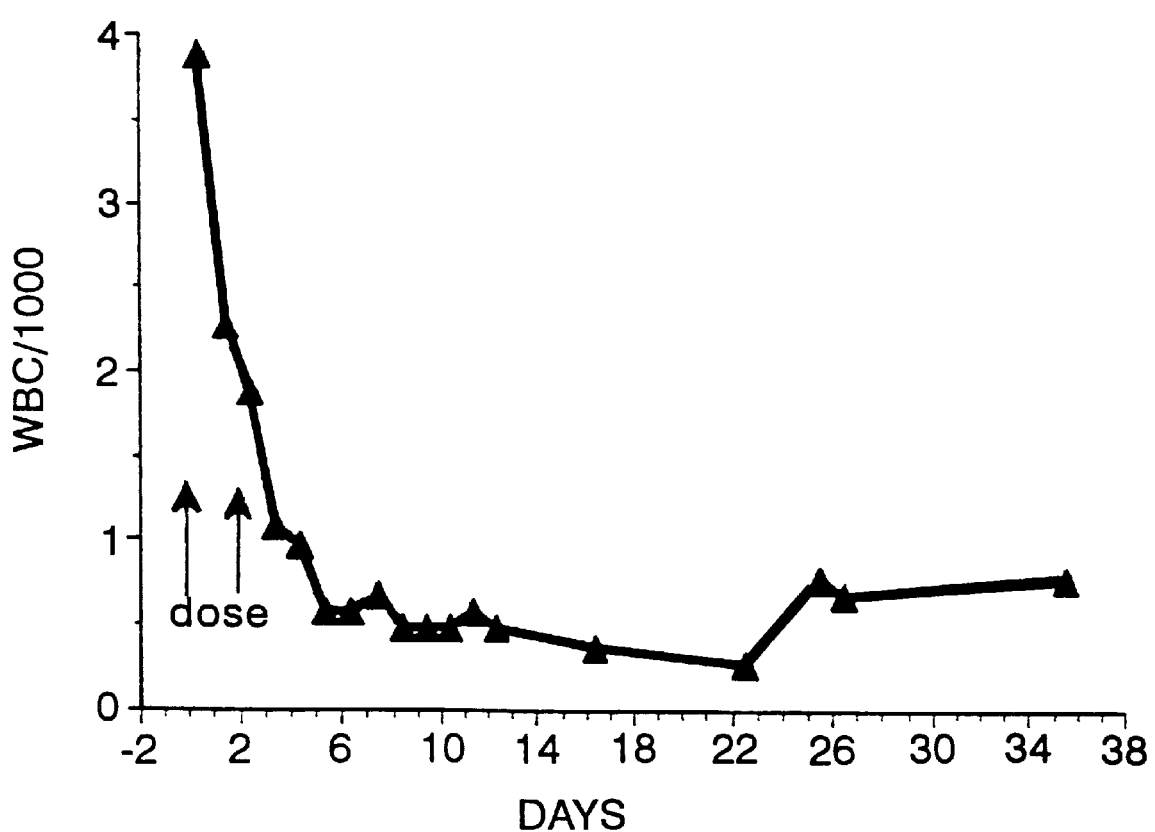
Figure 22A:
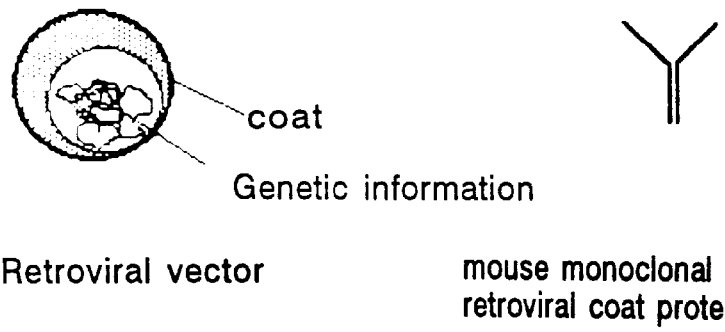
Figure 22B:
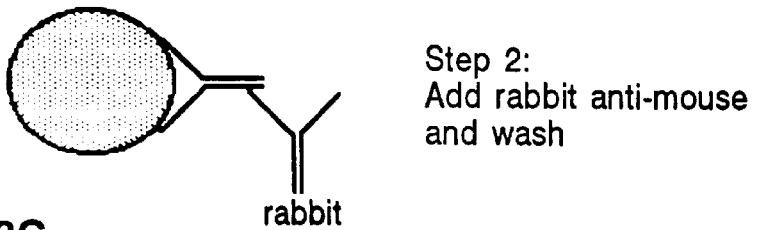
Figure 22C:
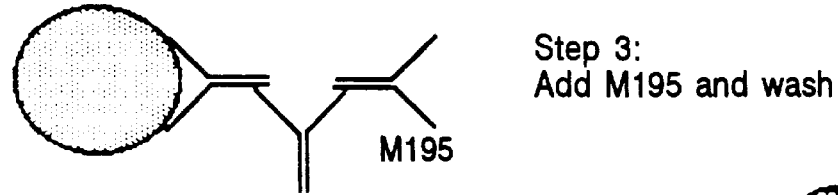
Figure 22D:
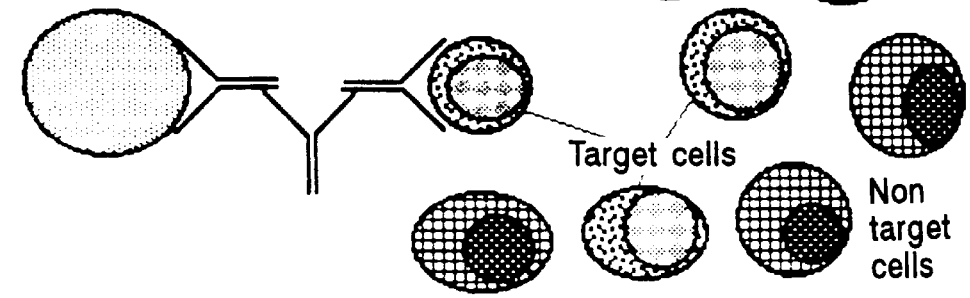

FIG. 21. Peripheral WBC counts post treatment for patient #6 (A). Total marrow blasts decreased by over 99%. Estimated total leukemia cells killed was about $10^{12}$. There was no non-hematologic toxicity.

FIGS. 22A–22D. Schematic diagram of the method of allowing targeted retroviral vectors to specifically bind to progenitor cells as described in text.

Figure 23A:
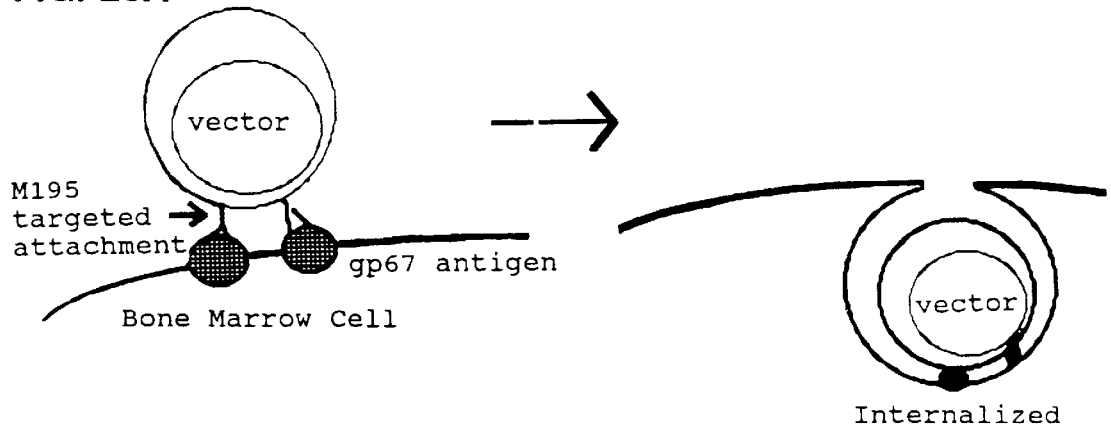
Figure 23B:
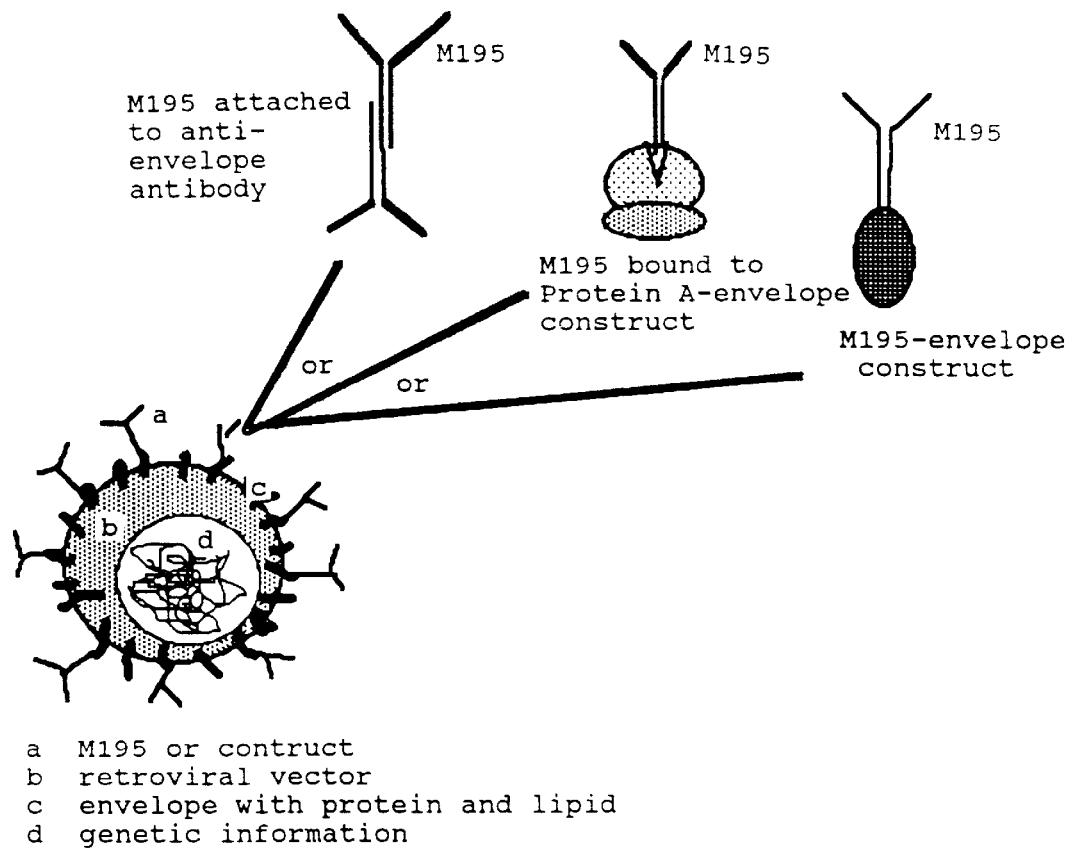

FIG. 23A–23B. (FIG. 23A) Internalization of an mAb targeted retroviral vector. (FIG. 23B) Alternate methods for attaching mAb to retroviral vectors.

DETAILED DESCRIPTION OF THE INVENTION

The invention provides a polypeptide which consists essentially of an amino acid sequence capable of specifically binding to the antigen to which monoclonal antibody M195 (ATCC No. HB 10306) binds, for example, an amino acid sequence which consists essentially of the amino acids of the hypervariable region of monoclonal antibody M195 which are necessary for binding to the antigen. In one embodiment, the polypeptide consists essentially of an amino acid sequence which is the same, or substantially the same, as the amino acid sequence of the hypervariable region of mouse monoclonal antibody M195.

The hybridoma which produces the monoclonal antibody designated M195 has been deposited on Dec. 12, 1989 with the American Type Culture Collection (ATCC) 12301 Parklawn Drive, Rockville, Md., U.S.A. 20852, under ATCC Accession No. HB 10306. This deposit was made pursuant to the provisions of the Budapest Treaty on the International Recognition of the Deposit of Microorganisms for the Purposes of Patent Procedure (Budapest Treaty).

Thus, one may obtain a polypeptide of the type described hereinabove by first obtaining monoclonal antibody M195 from the deposited hybridoma and then treating the M195 antibody so as to obtain from it the hypervariable region, e.g. by proteolytic digestion.

Alternatively, one may clone the DNA which encodes the hypervariable region of the M195 antibody and express the DNA, using standard recombinant DNA procedures, in a suitable unicellular or other host. In this way one may obtain a polypeptide within the scope of the invention.

Further, the polypeptide may be synthesized using well known techniques for synthesizing polypeptides, by chemical procedures.

The subject invention is not limited to polypeptides which contain an amino acid sequence which corresponds to the hypervariable region of the M195 antibody. The invention also embraces polypeptides which consist essentially of an amino acids sequence capable of specifically binding to the same antigen, i.e. the CD33 antigen, to which M195 binds. One way to obtain such a polypeptide is to substitute amino acid selectively for those present in the M195 hypervariable region so as to identify amino acids which when substituted affect, or do not affect, binding of the polypeptide to the antigen.

Another way to obtain such a polypeptide is to first obtain DNA encoding a polypeptide which is capable of specifically binding to the M195 antibody and then altering the DNA by site-directed mutagenesis so as to obtain DNA which, when expressed results in a polypeptide which consists of the amino acids present in M195 or another CD33-specific antibody which are essential for binding to the CD33 antigen.

An antibody typically comprises two pairs of two polypeptide chains. Each pair contains a light chain (having a molecular weight of about 25 kD) and a heavy chain (having a molecular weight of about 50–70 kD) held together by one or more disulfide bonds. Two such pairs are bound together by one or more disulfide bonds to form an antibody. The constant region of the antibody is located at the COOH-terminus of each chain and provides the effector function of the antibody. The variable region of the antibody is located at the $NH_2$-terminus of each chain and gives the antibody its specificity to a particular antigen. Within the variable region are hypervariable regions, segments of the variable regions in which most of the variation in amino acid sequence is found. The remainder is made up of relatively conserved amino acid sequences in a single species, which are called the framework regions (96,97). As used in this patent, the term "human framework region" is a framework region that is similar (85% or more homology) to the corresponding sequence of a naturally occurring human antibody.

A chimeric antibody is one in which portions of the antibody are derived from two or more different organisms. Typically, such a chimeric antibody is prepared in an effort to provide a broader range of functions for, or broader host acceptability of, the antibody.

In a further embodiment, this invention provides chimeric antibodies comprising a polypeptide described hereinabove. Thus, a chimeric antibody in accordance with this invention is one in which at least one chain, either the heavy chain or the light chain, comprises an amino acid sequence consisting essentially of an amino acid sequence capable of specifically binding to the antigen to which monoclonal antibody M195 binds; for example, an amino acid sequence which consists essentially of the amino acids of the hypervariable region of monoclonal antibody M195 necessary for binding to the antigen, i.e. an amino acid sequence which is the same, or substantially the same, as the hypervariable region of M195.

Although as few as one chain may in principle comprise such an amino acid sequence it will generally be the case that at least two of the chains will do so, usually, both chains of the same type, i.e. both heavy chains or both light chains. Of course, the antibody may comprise four such amino acid sequences by including such sequences in both heavy and in both light chains.

Such an antibody may be prepared by methods well known in the art, including, for example, the methods described in U.S. Pat. Nos. 4,816,397 and 4,816,567; PCT Patent Publication Nos. WO86/01533 and WO89/01975; and reference 98, using DNA encoding such an amino acid sequences, e.g. DNA encoding the hypervariable region of an antibody directed to the CD33 antigen, e.g. M195.

Preferably, the constant region of such a chimeric antibody is the same, or substantially the same, as the constant region of a human immunoglobulin in order to minimize an antigenic response in a human subject to whom the antibody is administered.

One particularly preferred type of chimeric antibody is a "humanized" antibody, that is, an antibody produced by molecular modeling techniques to identify an optimal combination of human and mouse antibody sequences, that is, a combination in which the human content of the antibody is maximized while causing little or no loss of the binding affinity attributable to the variable region of mouse antibody. Thus, in one embodiment the invention provides a chimeric antibody comprising the amino acid sequence of a human framework region and of a constant region from a human antibody so as to "humanize" or render nonimmunogenic the hypervariable region from a mouse monoclonal antibody such as M195 (99, 100, 101 and 102).

It is well known that hypervariable regions are tertiary structures derived from triplets of non-contiguous variable regions of amino acid sequence (CDRS). CDRs may be genetically grafted into an amino acid sequence to achieve a desired hypervariable sequence. (103, 104) Thus, the invention specifically includes chimeric antibodies which comprise polypeptides i.e. amino acid sequences of the type discussed above containing grafted CDR segments, together with human framework and constant regions.

This invention also provides therapeutic agents comprising either such polypeptides or chimeric antibodies as described above, or monoclonal antibody M195 per se and a cytotoxic agent conjugated thereto.

Of particular interest are therapeutic agents in which the cytotoxic agent is a radioisotope, such as an alpha particle emitter, for example, Lead-212, Bismuth-212, or Astatine-211, particularly Bismuth-212. Alternatively, the cytotoxic agent may be a beta particle emitter, for example, Iodine-131, Scandium-47, Rhenium-186, Rhenium-188, or Yttrium-90, particularly Iodine-131 or Yttrium-90. Still further, the radioisotope may be an auger electron generator, for example, Iodine-123, Iodine-125, Bromine-77, or Indium-111, particularly Iodine-123; or a fissionable nuclide such as Boron-10 or an Actinide.

Alternatively, the cytotoxic agent may be any of the well known toxins such as ricin, conjugation of which to polypeptides and antibodies has previously been described.

Still further, the cytotoxic agents may be any of the well known cytotoxic drugs such as adriamycin or 5-fluorouracil, conjugation of which to polypeptides and antibodies has previously been described.

The precise method by which the cytotoxic agent is conjugated to the polypeptide or antibody will vary depending upon the nature of the cytotoxic agent. However, those skilled in the art are well aware of such methods. Merely by way of example, a radioisotope may be conjugated to either the polypeptide, the chimeric antibody or the M195 antibody per se by means of a bifunctional chelate.

The invention also provides a pharmaceutical composition comprising a chimeric antibody in accordance with the invention in an amount be effective to treat leukemia, and a pharmaceutically acceptable carrier.

As used herein, leukemia includes, but is not limited to, acute and chronic myeloid and thymphoid leukemia as well as myelodysplastic syndromes, preleukemia syndromes, refractory anemias, and myeloproliferative disorders. Additionally, the invention encompasses pharmaceutical compositions which comprise any of the therapeutic agents described hereinabove in an amount effective to treat leukemia and a pharmaceutically acceptable carrier. Further, the invention also includes a pharmaceutical composition comprising an amount of monoclonal antibody M195 effective to treat leukemia and a pharmaceutically acceptable carrier.

The effective amount for use in the pharmaceutical compositions of the invention will vary depending upon a number of factors all of which are well known to those skilled in art. Such factors include the precise identity of the therapeutic agent, including the identity of the cytotoxic agent; the identity of the carrier; the sex, age and other characteristics of the patient to be treated as well as the disorder to be treated; and the route of administration to be employed. Persons skilled in the art are well versed in determining such effective amounts by routine methods. In general, effective amounts will vary from about 0.1 mg to about 500 mgs, preferably from about 1 mg to about 200 mg for an adult patient.

Pharmaceutically acceptable carriers are likewise well known in the art and include both liquids such as agueous buffered solutions and solids including appropriate excipients. Other ingredients including preservative, flavoring agents, and the like may optionally be present.

This invention also provides a method of treating a patient who has leukemia which comprises administering to the patient an amount of a therapeutic agent or a chimeric antibody in accordance with the invention so as to destroy the leukemic cells and thereby treat the patient. In such methods, the amount of therapeutic agent or chimeric antibody is typically from about 0.05 mg. to about 500 mg, i.e. from about 0.1 mg to about 100 mg.

Although the therapeutic agent or chimeric antibody may, in principle, be administered in any of the various methods known in the art, intravenous administration is typically the methods of choice.

In one embodiment, the therapeutic agent comprises Iodine-131 and the effective amount comprises from about 50 mCi to about 200 mCi. In another embodiment, the therapeutic agent comprises Yttrium-90 and the effective amount comprises from about 10 mCi to about 50 mCi. In yet another embodiment, the therapeutic agent comprises Bismuth-212 and the effective amount comprises from about 20 mCi to about 80 mCi. In still another embodiment, the therapeutic agent comprises Iodine-123 and the effective amount comprises from about 100 mCi to about 300 mCi.

This invention additionally provides a method of destroying a human patient's natural bone marrow cells which comprises administering to the patient an amount of a chimeric antibody or a therapeutic agents of the invention effective to destroy the patient's bone marrow cells.

In such methods the amount of the therapeutic agent may vary, again within ranges well known to those skilled in the art. Typically, the amount of the therapeutic agent or the chimeric antibody is about 0.01 mg. to about 50 mg and is administered intravenously.

Additionally, this invention provides a method of treating leukemia which comprises removing bone marrow cells, including leukemia cells, from a human leukemic patient; contacting the bone marrow cells so removed with an amount of a chimeric antibody or a therapeutic agent of the invention, or of monoclonal antibody M195 so as to destroy the leukemia cells present in the bone marrow cells; and autologously reinfusing the resulting bone marrow cells into the patient. Preferably, the contacting of the bone marrow cells, including leukemia cells, removed from the patient is effected in the presence of rabbit, guinea pig, or human complement.

Additionally, this invention provides a method of diagnosing leukemia in a human patient which comprises administering to the patient a polypeptide or chimeric antibody of the invention labelled with an imaging agent under conditions so as to form a complex between the antibody and any leukemia cells present in the patient, imaging any complex so formed, and thereby diagnosing leukemia. The invention also encompasses a method of diagnosing leukemia by administering to the patient M195, or an antibody directed to the antigen to which the M195 monoclonal antibody (ATCC No. HB 10308) is directed, labelled with an imaging agent, under conditions so as to form a complex between the antibody and any leukemia cells present in the patient, imaging any complex so formed, and thereby diagnosing leukemia. Generally, the imaging agent is internalized into the leukemia cells.

In one embodiment, the antibody is monoclonal antibody M195 and the imaging agent is a radioisotope such as a positron-emitting radiometal; a gamma-emmitting radiometal; Iodine-131; Iodine-123; Indium-111 or Technetium-99m.

Finally, this invention provides a method of introducing or carrying genetic information into leukemia cells which comprises contacting cells with a polypeptide or a chimeric antibody of the invention, to either of which the genetic information is attached or with which it is associated, so that the polypeptide or the antibody, bind to the cells to form a complex, which is thereafter internalized into the cells so as to thereby introduce or carry the genetic information into the cells.

Additionally the invention provides a method of carrying genetic information into a hematopoietic cell by contacting the cell with either the M195 monoclonal antibody or an antibody which is directed the antigen which the M195 monoclonal antibody is directed, to either of which the genetic information is attached, so that the antibody binds to the cell to form a complex, which is thereafter internalized into the cell so as to carry the genetic information into the cell.

In one embodiment, the genetic information comprises a retroviral vector attached to the antibody.

The following experiments are set forth to aid in an understanding of the inverting as defined by the claims which follow hereafter, but are not intended to, and should not be construed so as to limit, in any way the scope of the invention defined thereby.

EXPERIMENT 1

This experiment, and experiment 2, describe a mouse monoclonal antibody, M195, which defines an antigen restricted to early myeloid cells, monocytic cells, and ANLL. The antigen is carried on the CD33 protein. The antigen is not detectable on any other adult tissues and is useful in the study of myelomonocytic differentiation and in the diagnosis and therapy of ANLL. This experiment describes the distribution of the antigen on cell lines, normal tissues, and mature hematopoietic cells. The antibody's biological activity, affinity, and quantitative distribution on individual cells are presented.

MATERIALS AND METHODS mAbs. mAb M195 was produced from hybridomas resulting from a fusion of SP2/0-Ag14 mouse myeloma cells and the spleen cells of a 5-week-old BALB/c mouse immunized with leukemia cells from a patient with AML (FAB-M2). Supernatant fluids from cloned hybridoma cultures were screened against a panel of leukemia cell lines and the original ANLL leukemia cells using *Staphylococcus aureus* protein A (PA) erythrocyte rosetting (see below). The repeatedly sub-cloned M195 hybridoma was expanded in the peritoneal cavity of doubly pristine-primed (C57BL/6× BALB/c) F1 mice.

M195 was purified on PA-Sepharose (Pharmacia) by affinity chromatography using sequential pH step elutions. Purity was determined on sodium dodecyl sulfate (SDS)-polyacrylamide gels stained with Coomassie brilliant blue. Control antibodies included mAb AJ2, reactive with a broadly expressed cell surface antigen (VLA) (103), and mAb M31 (reactive with the Lewis X antigen).

Screening of Hybridoma Supernatants. Four thousand cells (HL60 or the original immunizing ANLL cells) in 10 μl of RPMI with 10% fetal calf serum (FCS) were allowed to settle and attach to concanavalin A-coated (Pharmacia) Terasaki 60-well plates (NUNC) for 45 min at 20° C. as described (104, 105). Hybridoma supernatants were tested for reactivity on these cells using PA-coated human O⁻ red blood cell rosettes as indicators (104).

Cells and Cell Lines. Heparinized peripheral blood samples and bone marrow aspirates were obtained from healthy volunteers and patients. Mononuclear cells were separated on Ficoll-Paque (Pharmacia), and adherent cells were isolated from the nonadherent mononuclear cells by plastic adherence for 2 hr. at 37° C. Polymorphonuclear leukocytes were purified from contaminative red blood cells after dextran sedimentation at 1×g for 60 min by ammonium chloride lysis in Tris buffer at pH 7.2. Platelets were separated from the Ficoll-Paque interface cells by differential centri-fugation. E-rosette-positive and negative fractions of mononuclear cells were separated after incubation and neuraminidase (Calbiochem) treated sheep red blood cells (GIBCO), followed by Ficoll-Paque gradient centrifugation and lysis of red cells with ammonium chloride.

Hematopoietic cell lines (Table 1) and nonhematopoietic cell lines (Table 3) were obtained from the human tumor banks of the Human Cancer Immunology Laboratory at Sloan-Kettering Institute. 1F10 and 1F10 (mono), an HL60 subclone and its monocytic differentiated form, were the gift of Dr. Y. Cayre (106).

Serologic Assays: Antibody specificity was determined on adherent cell lines plated in 60 well Terasaki plates using *Staphylococcus aureus* PA or rabbit antimouse Ig-coated human O red blood cells prepared as described (104) as indicators. Suspension target cells are assayed using the same indicator cells except that the target cells were attached to Terasaki plates immediately before testing using Concanavalin A (105). This assay is sensitive to concentrations of mAb M195 of about 1 ng/ml binding to HL60. Cells were considered negative if no rosettes formed below an ascites dilution of 200 and absorption analyses were also negative. Ascites fluids were considered "weakly positive" on a cell line if greater than 50% of cells formed rosettes at dilutions between 200 and 100,000. "Weakly positive" cells were confirmed as reactive by absorption analysis (see below). Ascites from mice bearing hybridomas were considered positive with a cell line if resetting of cells occurred at a dilution of greater than 100,000. If purified antibody was used, cell lines were scored "positive" for resetting at concentrations below 50 ng/ml and "weakly positive" at concentrations of 50–500 ng/ml. Reactivity was also confirmed by direct radioimmunoassay and by complement fixation assays (see below).

Absorption Analysis. Two to ten million cells were washed in PBS and pelleted at 500×g in a 5×50 mm glass tube and allowed to react with an equal volume of ascites diluted to a concentration four times that needed to form 50% rosettes on positive cells: HL60 cells or the immunizing ANLL cells. (This was typically a dilution of ascites of 100,000–200,000.) The absorption proceeded for 30 min. at 4° C., and the mixture was again pelleted at 500×g. The supernatant was reacted with target cells lines in resetting assays as described above.

Antibody-dependent Cellular Cytotoxicity (ADCC). Assays to determine if M195 was capable of mediating ADCC were conducted essentially as described by Welt et al. (107). Target cells were incubated in $^{51}$Cr for ninety minutes and then washed of free $^{51}$Cr. M195 antibody was added at concentrations of 1–100 μg/ml on ice, and fresh peripheral blood mononuclear cells added at effector to target ratios of 10–40/1. Cells were incubated at 37° C. for 6–18 hr and harvested using a Skatron cell harvester, and released $^{51}$Cr was counted in a Packard gamma counter. Detergent lysed cells were used as a 100% control, and isotype matched irrelevant antibody treated cells were used as a negative control.

Radioiodination and Radioimmunoassays. Purified antibodies were labeled with Na-$^{125}$I, (New England Nuclear)

using chloramine-T to start and sodium metabisulfite to stop the reaction. Specific activity was between 2 and 10 µCi/µg of protein. Immunoreactivity was between 40 and 60% as determined by serial binding to an excess of live HL60 cells. Radioimmunoassays were conducted on $5\times10^6$ live cells in 100 µl RPMI with 10% FCS and preincubated 15 min. with 2% heat inactivated normal rabbit serum to block nonspecific binding. Binding proceeded at 4° C. for 90 min followed by the tree washes with RPMI/FCS. Bound radioactivity was measured in the cell pellets in a Packard gamma counter.

Preparation of F(ab)'2 Fragments. One mg of purified immunoglobulin was reacted at 37° C. for 6 hr with immobilized pepsin beads (Pierce Chemicals) in acetate buffer at pH 4.5. The reaction was stopped by adjusting the pH to 8.8 and sedimenting the pepsin beads at 15,000×g for 1 min. Undigested immunoglobulins and Fc fragments were removed by reaction with Protein A Sepharose (Pharmacia). Purity of fragments was determined by SDS-polyacrylamide gel fractionation followed by Coomassie blue staining.

Competition Radioimmunoassay for Blocking Antigen in Serum. Serum from patients with hematopoietic neoplasms was obtained from fresh clotted blood and stored at −70° C. until use. The presence of blocking M195 antigen in sera was assayed by incubating 50 µl of freshly thawed serum and a dilution of $^{125}$T-labeled mAb M195 IgG for 20 min at 4° C. M195 IgG was at a concentration sufficient for 50% maximal binding to $5\times10^5$ HL60 target cells. The cells were then added and the incubation continued for 60 min at 4° C. followed by two washes with RPMI medium. Inhibition of M195 IgG binding was scored as the percent decrease in binding to HL60 as compared to mAb M195 incubated in the presence of 2% bovine serum albumin (BSA) in PBS and no competing sera.

Complement-mediated Cytotoxicity. Twenty-five µl of target cells at $2\times10^6$ cells/ml were mixed with 25 µl of complement and 25 µl monoclonal antibody at 4° C. The mixture was then incubated at 37° C. and occasional shaking for 45 min. Live and dead cells were enumerated using trypan blue exclusion as an indicator.

Guinea pig serum and baby rabbit serum were purchased from PelFreeze; human sera were obtained from volunteers. All complement sources were stored at −70° C. until use and not reused. Complement was used at the maximum concentrations not showing nonspecific lysis of the target cells: generally at 1:6–8 final dilution.

Indirect Immunoperoxidase and Immunofluorescence Assays. Histologically normal adult human tissues were obtained from surgical pathology specimens within 1–2 hr of resection. Several normal specimens of organs from several cases were used. Tissues were embedded in OCT compound after freezing in iopenthane/liquid $N_2$. Tissues were cut 4–8 µm thick, fixed in acetone, quenched with 0.1% $H_2O_2$, and blocked with either goat or horse sera. MAb M195 was used as supernatant, ascites, or purified IgG at 20 µg/ml. Positive and negative Ig controls were included in all studies. Goat anti-mouse IgG peroxidase conjugates (1:50 dilution) (Tago, Burlingame, Calif.) or biotinylated horse anti-mouse IgG with Avidin-biotin peroxidase complexes (Vector Laboratories, Burlingame, Calif.) were used as secondary reagents. Diaminobenzidine was used as a chromogen. For fluorescence studies, goat anti-mouse Ig fluorescein isothiocyanate conjugates (Becton-Dickenson) were used as secondary reagents.

Modulation of Cell Surface Antigen. Modulation of the cell surface antigen detected by mAb M195 after antibody binding was monitored by complement mediated cytotoxicity (108). HL60 cells were incubated with various concentrations of M195 IgG for up to 3 hr at 37° C. Additional antibody and rabbit complement were added at several time points and the amount of cell lysis was determined 45 min later.

Differentiation of HL60. A cloned variant of HL60, IF10 (106), and its differentiated monocytic variant (incubation with vitamin $D_3$ and phorbal myristate acetate for 3 days to promote monocytic maturation) were used (106). Both cell lines were kindly provided by Dr. Y. Cayre.

RESULTS

Distribution of M195 Antigen on Hematopoietic Cell Lines. mAb M195 was selected for detailed study from a group of several hundred hybridoma-produced antibodies generated from the fusion of a spleen from a mouse immunized with fresh live ANLL cells (FAB classification, M2). The antibody showed specific high titer binding in PA-rosette assays to the myeloid and monocytic cell lines. HL60, KG1, IF10, U937, and the monocytic variant of IF10 (Table 1). mAb m195 was weakly reactive with the erythroleukemic line K562 and not reactive with KG1a, an undifferentiated myeloid line. mAb M195 did not react with 18 lines of B cell origin at various stages of differentiation nor with 10 lines of T cell derivation. One null lymphocytic line, N-ALL-1 was weakly reactive. Activated B cells and activated T cells did not express antigen. Non-reactive cell lines were confirmed as negative by absorption assays which can detect about 1 ng of M195 binding in 1,000,000 cells; resetting assays detect binding at antibody concentrations of about 1 ng/ml. mAb AJ2 was used as a positive control in these assays where most cells were M195 antigen negative. This panel of cell lines showed that among hematopoietic cells M195 was restricted to the nonlymphoid lineages: it was most highly expressed on committed myeloid and monocytic cell lines and more weakly expressed on erythroid and earliest myeloid cells.

TABLE 1

Reactivity of M195 with Hematopoietic Cell Lines[a]

| Cell | M195 | AJ2 (positive control) |
|---|---|---|
| Myeloid | | |
| K562, HL60 | ⊖● | ● |
| KG-1, KG1a | ●○ | ●● |
| 1F10 | ○ | ● |
| Monocytic | | |
| U937, 1F10(mono) | ●● | ●● |
| THP-1 | ○ | |
| Pre-B cells | | |
| NALL-1, NALM-1 | ○○ | ● |
| NALM-6, NALM-16 | ○○ | |
| B cells | | |
| SK Ly-16, -18, Daudi, | ○○○ | ● |
| ARA-10, SK DHL-2, Raji | ○○○ | ●● |
| CCRF-SB, LICR/My-2 | ○○ | ● |
| BALL-1 | ○ | |
| Myelomas | | |
| Oda, U266, RPMI 8266 | ○○○ | ● |
| RCS, HAS, Brown | ○○○ | |
| EBV-transformed B cells (n = 15) | ○ | |

TABLE 1-continued

Reactivity of M195 with Hematopoietic Cell Lines[a]

| Cell | M195 | AJ2 (positive control) |
|---|---|---|
| T cells | | |
| T-45, CCRF-CEM, Molt 4 | ooo | ● |
| TALL-1, MT-1, HUT-102 | ooo | |
| RPMI 8402, CCRF-HSB2 | oo | |
| p12/chikawa, HPB-ALL | oo | ● |
| PHA blasts | o | |
| (n = 5) | | |

● = positive; ⊖ = weakly positive; o = negative.
[a]As determined by direct Protein A and mixed hemeadherence rosseting and absorption assays as described in the text.

Quantitative Analysis of Binding to Myeloid Cell Lines. In order to confirm the results of rosetting assays and absorption assays and to look at quantitative differences in the expression of the M195 antigen among the myeloid and monocytic cells a sensitive radioimmunoassay using direct binding of $^{125}$I-labeled purified M195 was used. Many of the hematopoietic cells have Fc receptors in addition to or instead of target antigen on their surfaces, and binding of radiolabeled IgG to these Fc receptors may confound the quantitative results of the radioimmunoassay. Therefore an F(ab')2 fragment of M195 was prepared and used in the assays to confirm the number of antigenic sites.

Figure 1A:
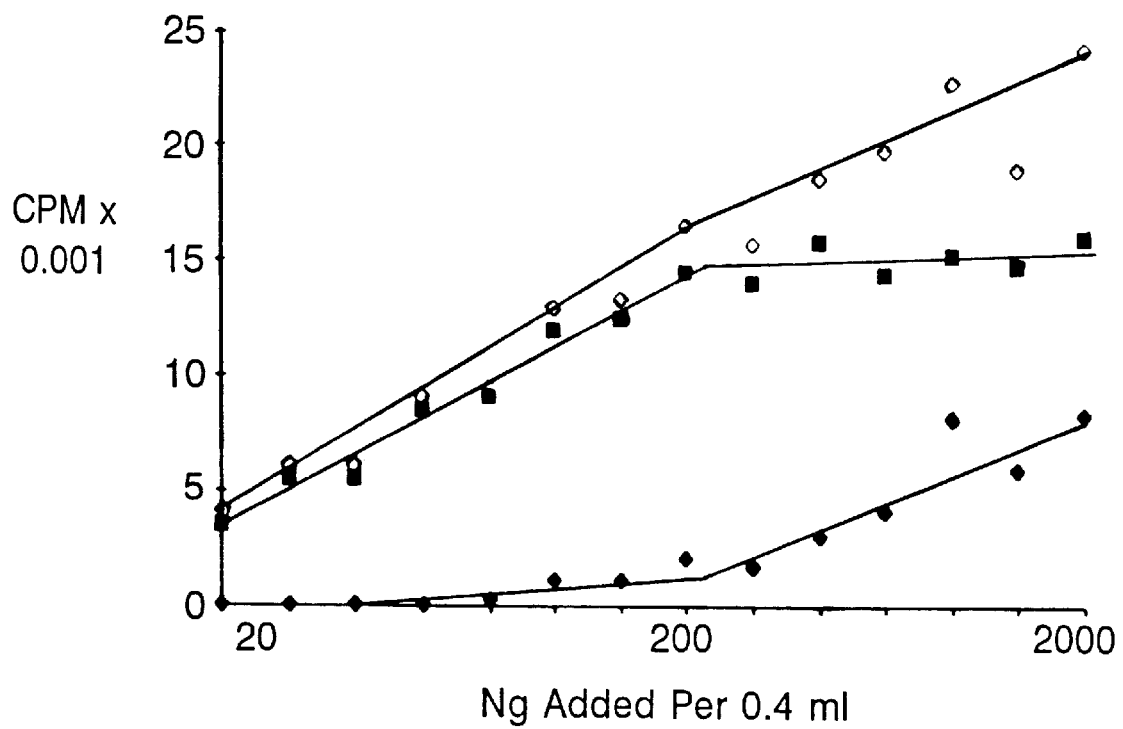
FIGS. 1A–1C. Radiobinding assays of M195 IgG and F(Ab)'2: Saturation and Scatchard analysis. Assays were conducted as described in Materials and Methods.
Figure 1B:
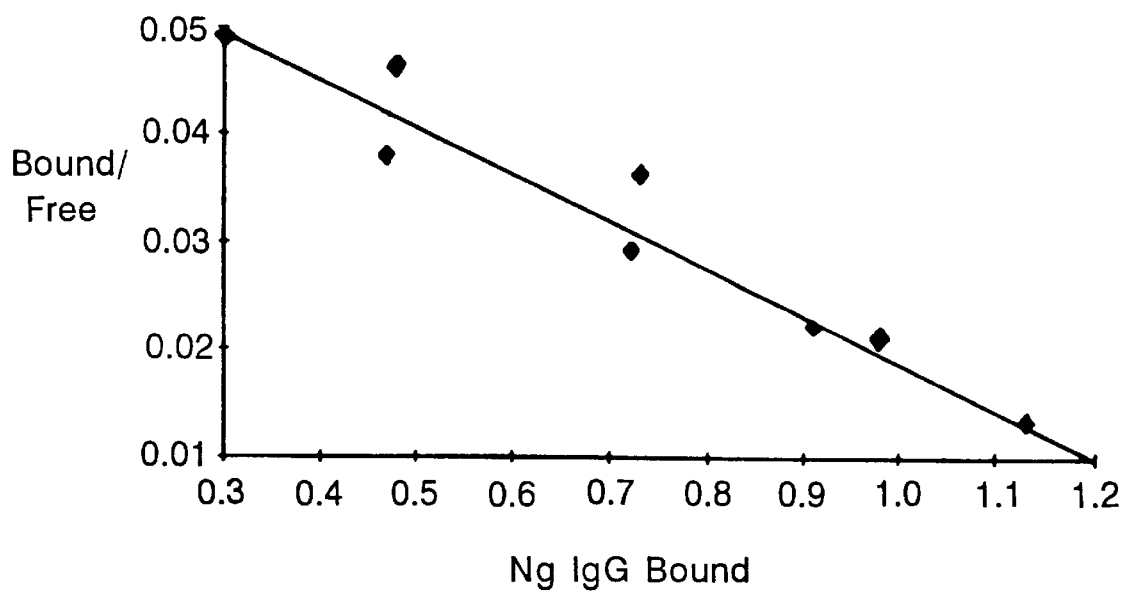
Figure 1C:
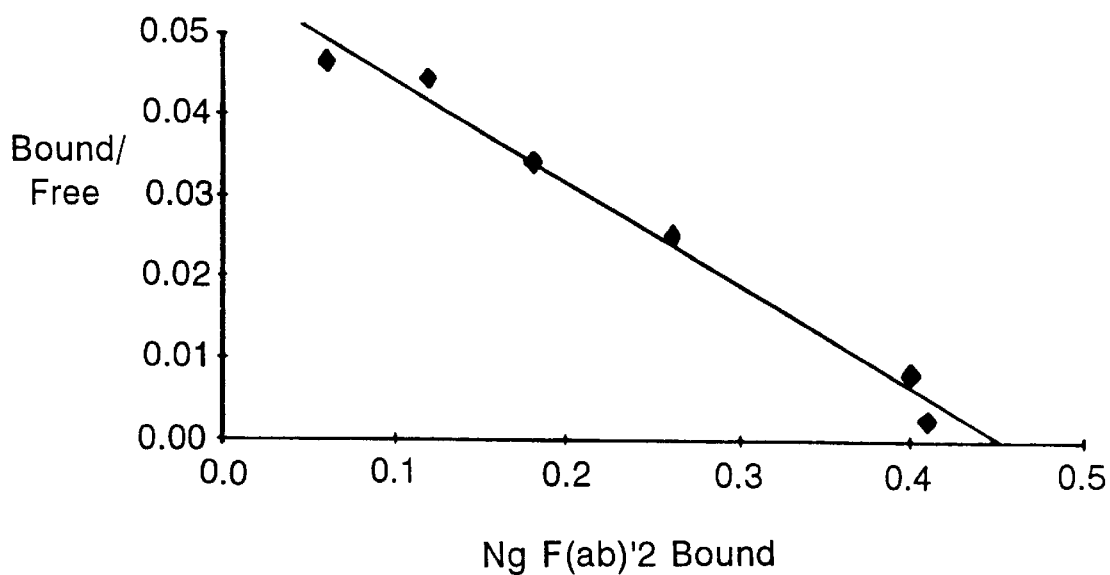

Binding of M195 IgG to HL60 showed saturation and specificity (FIG. 1A). Scatchard analysis showed an avidity of binding of 3×10$^9$ liters/mol (FIG. 1B) for the IgG. The number of binding sites calculated from this curve was approximately 100,000 per live HL60 cell. Scatchard analysis of several lots of M195 IgG on different passages of HL60 gave equivalent results. Analysis of purified F(ab)'2 of M195 (FIG. 1C) showed similar avidity (10$^9$ liters/mol) cells and numbers of binding sites (10,000/HL60 cell), suggesting that binding activity was not significantly altered by protease digestion of the fragment.

Both the intact IgG and the F(ab)'2, fragment were used for radioimmunoassays on hematopoietic cell lines (FIG. 2). Non-specific binding (binding of $^{125}$I-M195 in the presence of excess unlabeled M195) under the conditions of this assay was approximately 200 pg (1600 molecules) per 5×10$^5$ cells. Therefore, only binding above this level was considered significant. Since the assay was done under saturating concentrations of M195 IgG or F(ab)'2, the total binding could be used to calculate the number of sites per cell. HL60, IF10, and U937 had 6000–12,000 sites per cell. KG1 had about 3000 sites per cell. Binding to KG1a and K562 was not above the background of nonspecific binding (1600 sites), and the nonmyeloid cell lines were negative. The assays confirmed the specificity of M195 for these myeloid and monocytic cells and showed that binding was not Fc receptor related. The three cell lines positive by rosetting and absorption had similar quantities of M195 antigen expression.

Reactivity with Fresh Normal Hematopoietic Cells. M195 was tested by absorption analysis for reactivity with live peripheral blood elements and cells derived from the major hematopoietic organs (Table 2). mAb M31 was used as a positive control. No reactivity was seen with M195 on any of these cell types.

Quantitative Analysis of Binding to Hematonoietic Cells. Direct radioimmunoassays were performed on fresh hematopoietic cells to confirm reactivity and quantitative binding (Table 2). Red blood cells, platelets, spleen cells, bone marrow cells, and peripheral blood mononuclear cells were negative. Polymorphonuclear leukocytes showed binding to the intact IgG at about 800 sites per cell above background but did not show significant binding to the F(Ab)'2 fragment suggesting that even this minimal binding was via the Fc receptors. Peripheral blood adherent cells (macrophages) were positive and binding to the F(Ab)'2 showed about 5000 antigen sites per cell. Binding to peripheral blood E-rosette negative cells was marginally above background, possibly due to the presence of a small percentage of macrophages contained in this population. With the exception of macrophages, the direct radioimmunoassays shown here confirmed the specificity analysis by absorption. The lack of reactivity with macrophages in the absorption assay may be due to the inability to obtain the large quantity of viable cells containing enough antigen necessary to absorb M195 (1,000,000 macrophages with 5000 antigen sites per cell would absorb only about 1 ng of antibody). Lack of binding in these radioimmunoassays would rule out the presence of some M195 positive cells within a large heterogeneous population as in bone marrow, for example.

TABLE 2

Reactivity of M195 with Fresh Hematopoietic Cells[a]

| | Assay Type | | |
|---|---|---|---|
| Cell Type | Absorption | Radio-immunoasay | Complement Lysis |
| T-enriched PBL[b] | – | – | – |
| B-enriched PBL | – | – | – |
| Granulocytes | – | – | – |
| Adherent monocytes | – | – | + |
| Platelets | – | – | ND[c] |
| Red blood cells | – | – | ND |
| Nonadherent PBMC | ND | – | – |
| Splenic T enriched | ND | – | – |
| Splenic B enriched | ND | – | – |
| Splenic mononuclear | – | ND | –[d] |
| Bone marrow mononuclear | – | – | –[d] |
| Lymph node mononuclear | – | ND | ND |
| Fetal thymocytes | – | ND | ND |

[a]Conducted as described in the text.
[b]PBL = peripheral blood lymphocytes; PBMC = peripheral blood mononuclear cells.
[c]ND = not done.
[d]Nonadherent cells.

Complement-mediated Cytotoxicity Assays. Complement-mediated cytotoxicity was also used to confirm specificity. Assays were first done to determine if mAb M195 was capable of killing cells in the presence of rabbit, guinea pig, and human sera as sources of complement. Enzyme-linked immunosorbent assays showed mAb M195 to be an IgG2a class immunoglobulin, which is generally able to fix complement. Using HL60 as targets, M195 was capable of killing cells in the presence of guinea pig and rabbit complement but not human complement. In the presence of human complement, killing rarely occurred and was only 10–15% above background at its highest. Cell lines not expressing the antigen were not killed. No killing occurred in the absence of antibody or a source of complement.

Figure 3:
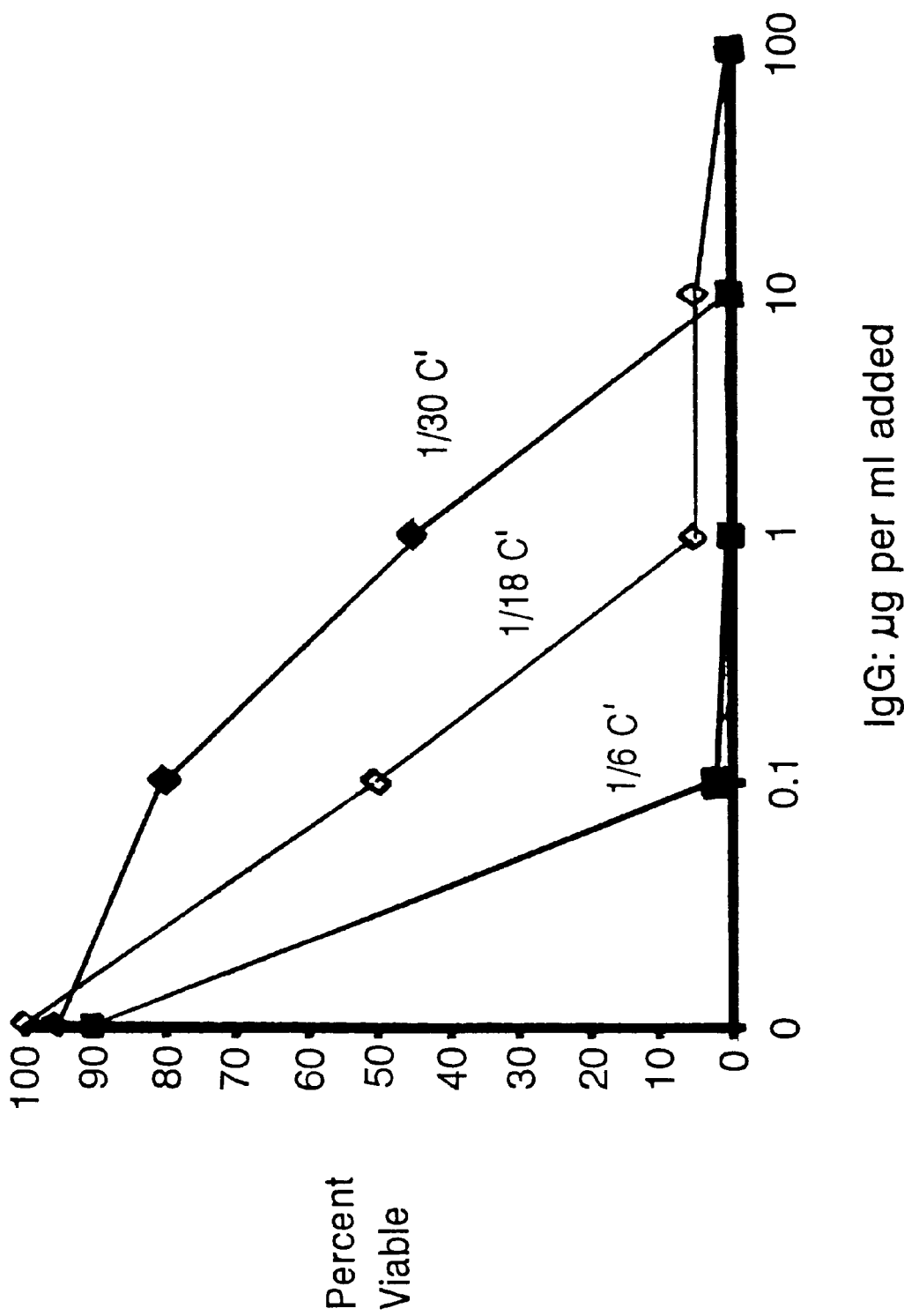
FIG. 3. Complement cytotoxicity by M195 IgG on HL60 cells using rabbit complement. The concentration of rabbit complement is shown in the figure: final dilution of 1/6 (■), 1/18 (◇), and 1/30 (◆). The assay was conducted as described in Materials and Methods.
Figure 4:
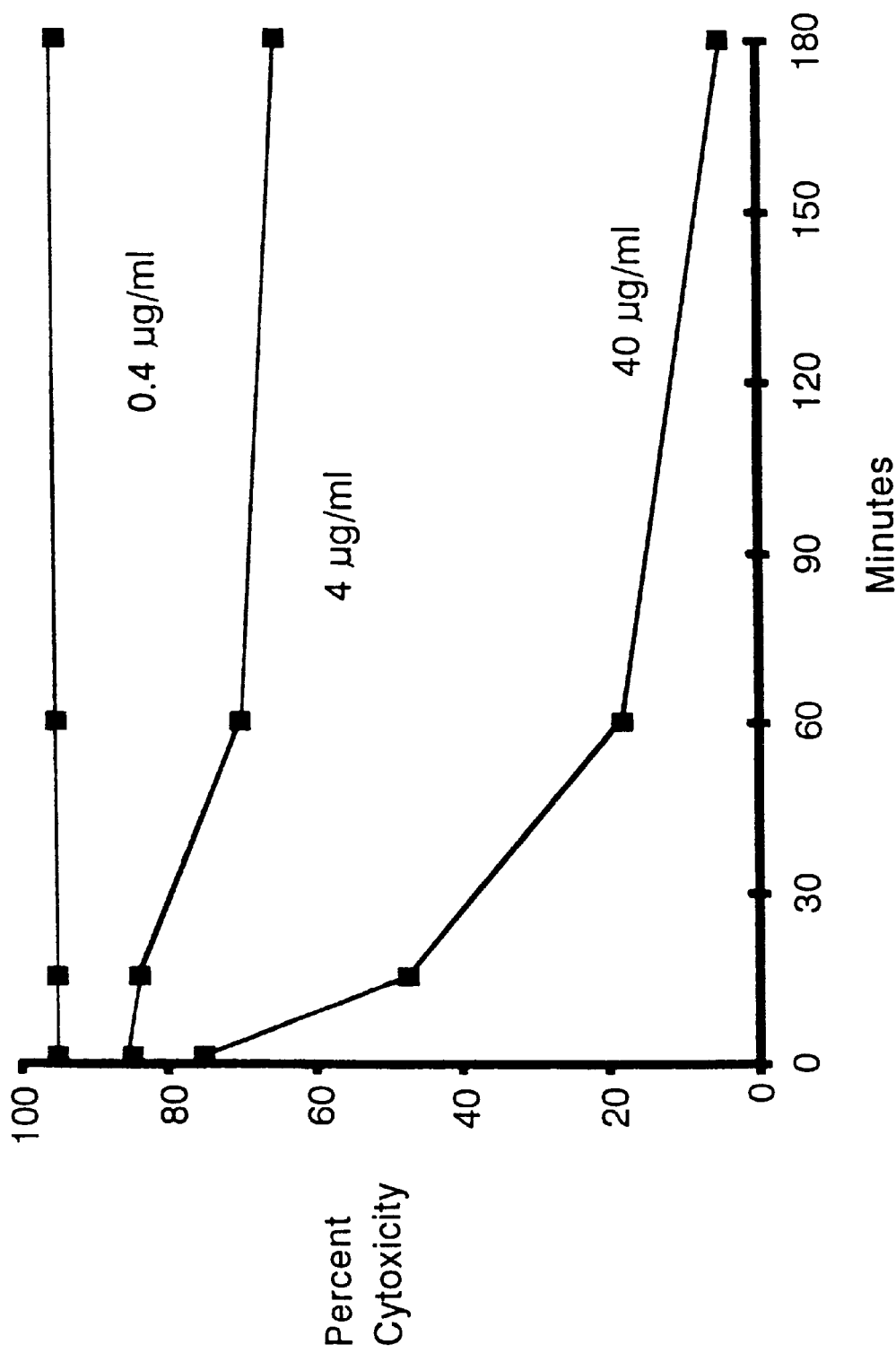
FIG. 4. Antigenic modulation after exposure of HL60 cells to mAb M195. The assay was conducted as described in Materials and Methods. M195 IgG was added at the concentrations shown in the figure and allowed to incubate at 37° C. for times indicated on the X axis. Cells were then tested for lysis by an additional aliquot of M195 IgG with rabbit complement at 37° C. for 45 min. Cytotoxicity after this second addition is shown on the y axis.

Cytotoxicity was antibody concentration dependent and complement concentration dependent (FIG. 3). However, at concentrations of 10 μg/ml or greater of M195, nearly all cells were killed even with rabbit serum diluted 30-fold.

The complement assay was used to confirm the specificity analysis derived from the absorption assays and radioimmunoassays (Table 2). Complement assays are not confounded by Fc receptor binding and are able to determine percentages of cells within a large population which are antigen positive. Assays were conducted at 10 and 100 μg/ml M195 with rabbit serum diluted to 1:18 final concentration. HL60 and fresh monocytic leukemias were used as positive controls and B cell lineage RAJI cells and chronic lymphocytic leukemia cells were used as negative controls. Complement and antibody alone controls were also included. Background killing was between 1–5% in the controls without antibody or complement and 5–10% in the spleen E-rosette negative cells. Because of this background of several percent, it is not possible to determine if positive cells are present in a sample at this level or lower.

Only one population of mature normal hematopoietic cells showed killing above background using M195 and rabbit complement: peripheral blood adherent cells. Among three samples of adherent cells, 35–50% of cells were killed, showing that a subpopulation of these cells expressed the M195 antigen. This assay confirmed the radioimmunoassay data.

In chronic myelogenous leukemia (CML) mononuclear cells, a low percent of cells (5–6%) were killed above background (not shown). The cells comprising the CML mononuclear cell population include blasts through band forms with a predominance of the more mature myeloid cells. Morphologic analysis of these cells before and after antibody and complement treatment did not show which cells, if any, had been selectively killed. Because peripheral blood cells from patients with CML represent the full spectrum of maturing myelogenous cells, this lack of significant cytotoxicity confirms the lack of reactivity of M195 with the vast majority of adult myelogenous cells.

Reactivity of M195 and Differentiated HL60 Cells. IF10 cells and differentiated monocytic IF10 cells were provided by Dr. Yvon Cayre. One hundred percent of the IF10 cells became morphologically changed and adherent. The reactivity of M195 was tested by both rosetting and radioimmunoassays before and after differentiation. In the differentiated monocytic 1F10 cells there was a 40% loss of antigen expression by radioimmunoassay. Rosetting assays remained positive but the titer of binding dropped 10-fold. Quantitative binding to the differentiated 1F10 was similar to fresh normal adherent monocytes, suggesting the loss of antigen with monocytic differentiation among fresh hematopoietic cells was paralleled by this model line in vitro.

ADCC Assays. M195 did not show any ability to mediate ADCC against HL60 cells or U937 under the conditions described in Materials and Methods. These cells are the highest expressors of the antigen among those tested.

Reactivity of M195 with Nonhematopoietic Cell Lines. M195 was tested for reactivity with 70 cell lines derived from a wide spectrum of cancers (Table 3). No reactivity was seen. Monoclonal antibody AJ2 was included as a positive control and was positive in every case tested. Therefore, the M195 antigen appears to be restricted to hematopoietic cells.

TABLE 3

Reactivity of M195 with Non-Hematopoietic Cell Lines[a]

| | | M195 | AJ2 (positive control) |
|---|---|---|---|
| Astrocytomas | SK-MG-1,-2,-3 | ooo | ● |
| | -4,-6,-7,-9 | | ● |
| | -12,-15,17,-23 | oooo | ● ● |

TABLE 3-continued

Reactivity of M195 with Non-Hematopoietic Cell Lines[a]

| | | M195 | AJ2 (positive control) |
|---|---|---|---|
| Bladder cancers | T-24, 253J,5637 | ooo | |
| Breast cancers | SK-BR-3,-5,-7 | ooo | |
| | BT-20,MCF-7 | oo | ● |
| Cervical cancers | CC-A, CC-B, HT-3 | ooo | ●●● |
| | C41 | o | ● |
| Choriocarcinomas | GCC-SV(c), Lu-75(c) | oo | |
| Colon cancers | SW-403,-480,-620 | ooo | ●●● |
| | -116,-1417 | oo | ●● |
| | HT-29,SK-C0-10 | oo | ●● |
| | CaCo-2,HCT-15 | oo | ●● |
| Lung Cancers | SK-LC-1,-4–6 | ooo | ● ● |
| | -8,9,-10,-17 | oooo | ● ● |
| | Calu-1,-6,Sk-Lu-1 | ooo | ●●● |
| | SK MES-10P | o | ● |
| Melanomas | SK MEL-13,23,-28 | ooo | ●●● |
| | -29,-37,-93 | ooo | ●●● |
| | -173,MeWo | oo | ● |
| Neuroblastomas | SK-N-MC,PNDW | oo | ●● |
| Ovarian cancers | SK-OV-3,OV-2774 | oo | ● |
| Pancreatic | ASPC-1,-2 | oo | ●● |
| Renal cancers | SK-RC,-1,-2,-7 | ooo | ● |
| | -8,-9,-20,-28, | oooo | ●● |
| | -29,-45,-48 | ooo | ●●● |
| Uterine cancer | ME 180, SK UT-1 | oo | ●● |

[a]Conducted as described in Table 1.

Tissue Distribution of M195. The reactivity of M195 with human tissues was determined in indirect immunofluorescence and indirect immunoperoxidase assays on fresh frozen tissue (Table 4). Among 25 different tissue types, reactivity was not seen. These data on fresh tissue are consistent with the specificity data obtained from the assays with cell lines above.

TABLE 4

Tissue Distribution of M195[a]

| Tissue | Fluorescence | Peroxidase |
|---|---|---|
| Adrenal | O | O |
| Bladder | O | O |
| Blood vessels | O | O |
| Brain | O | O |
| Breast | O | O |
| Capillaries | O | O |
| Cervix | O | O |
| Colon | O | O |
| Heart | O | O |
| Kidney | O | O |
| Liver | O | O |
| Lung | O | O |
| Lymph node | O | O |
| Ovary | O | O |
| Pancreas | | O |
| Placenta | O | O |
| Prostate | O | O |
| Skin | O | O |
| Small Intestine | O | O |
| Stomach | O | O |
| Testis | O | O |
| Thyroid | O | O |
| Ureter | O | O |
| Uterus | O | O |
| HL60 (positive control) | P | P |

O = negative; P = positive staining
[a]Conducted as described in the Materials and Methods M195 Reactivity with Fresh Leukemias. M195 reacted with most myelogenous leukemias and rarely with lymphoid leukemias in rosetting assays. Because of the nature of the rosetting assay, it was not possible to determine which cells were reactive or what percentage of blasts were positive. These issues and a detailed analysis of the specificity and activity of M195 in comparison to standard cell surface markers are described in detail in Experiment 2 below and in reference 109.

M195 Blocking Antigen in Serum. In order to determine if the M195 antigen was shed into sera from hematopoietic cells, sera from people with a variety of leukemias and lymphomas or from healthy individuals were tested for soluble antigen capable of blocking of the binding of radiolabeled mAb M195 to HL60 cells (Table 5). Three of 39 human sera blocked binding significantly. The blocking was not complete. One serum was from a patient with CML. Two sera of six patients with acute lymphocytic leukemia partially block binding. The leukemia cells from both of these patients were not reactive with M195 antibody suggesting that the blocking antigen was not shed from these cells or that the blocking activity was not specific. These data suggest that M195 antigen in the serum would not be capable of preventing mAb M195 from reaching target cells. Because the sensitivity of this assay is about 200 ng/ml of M195, it is possible that M195 is expressed at lower levels than this in sera. In addition, monovalent antigen with low avidity for the M195 IgG may be present but unable to block binding.

TABLE 5

M195 Blocking Factors in Sera of Patients with Leukemia

| Serum Source | Number Tested | Number Blocking[a] |
|---|---|---|
| Normal | 6 | 0 |
| AML | 13 | 0 |
| CML | 6 | 1 (52%)[b] |
| ALL | 6 | 2 (56%, 67%) |
| NHL/CLL | 8 | 0 |
| Rabbit, mouse, horse | 5 | 0 |

[a]A serum able to reduce by 50% or more, direct binding of 200 ng/ml radioiodinated M195 to HL60 target cells.
[b]The percent reduction by each positive serum.

Figure 5:
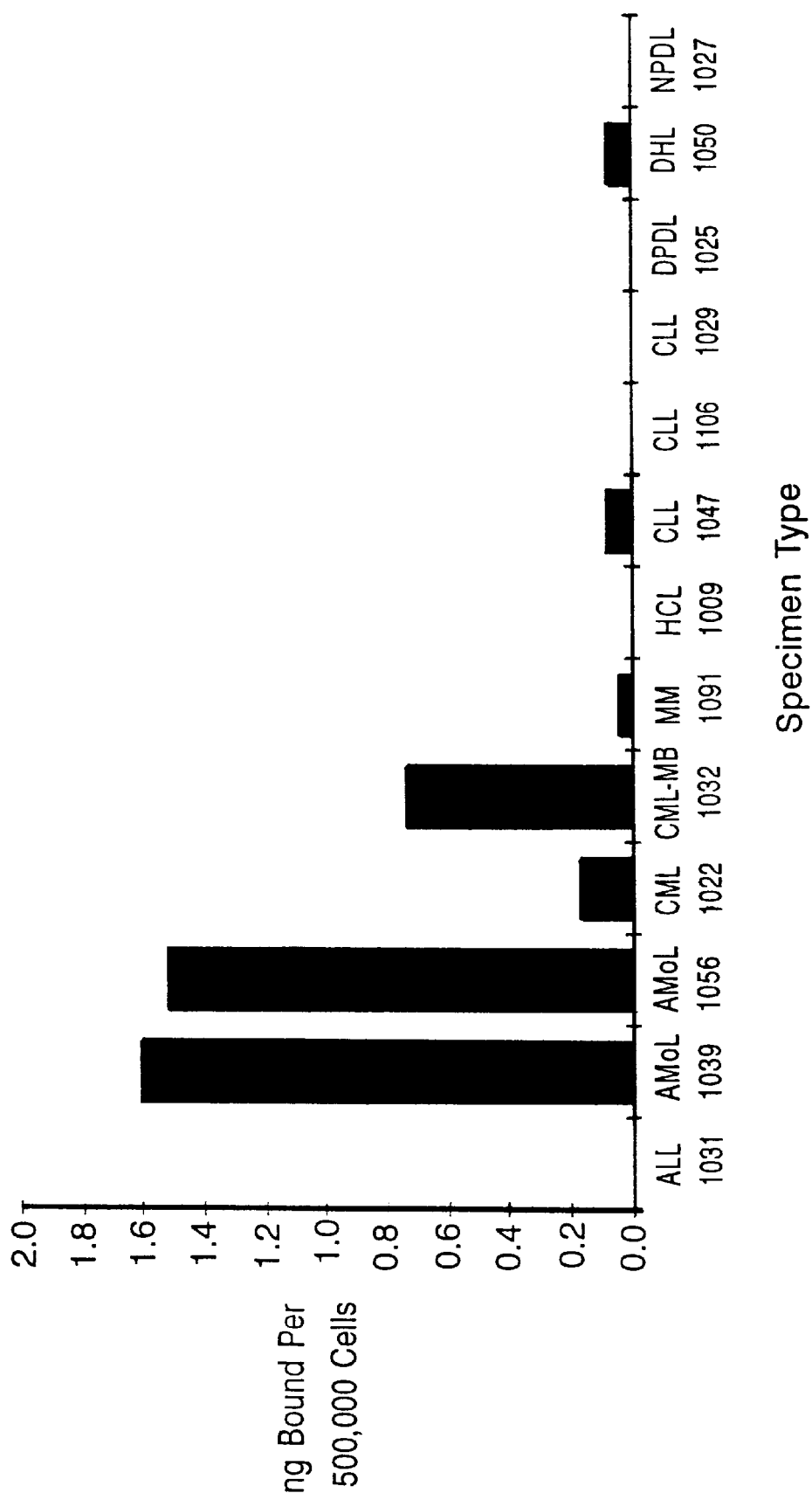
FIG. 5. Direct Radioimmunoassay for mAb M195 IgG on fresh hematopoietic neoplasms. The assay was conducted as described in Materials and Methods. The identities of the specimens are shown along the X axis; 1 ng bound per 500,000 cells is equivalent to 8000 IgG per cell. AMOL is acute monocytic leukemia; CML-MB is myeloblastic CML; MM is multiple myeloma; HCL is hairy cell leukemia; CLL is chronic lymphocytic leukemia; DPDL is diffuse poorly differentiated lymphoma; DHL is diffuse histiocytic lymphoma; NPDL is nodular poorly differentiated lymphoma; The lymphomas were suspensions made from lymph nodes. Background nonspecific binding was 0.2 ng bound. Only specific binding is shown.

Antigenic Modulation The ability of M195 to induce modulation of the antigen from the surface of HL60 cells was studied using complement-mediated cytotoxicity. HL60 cells were reacted with M195 at various concentrations, and the ability of M195 to kill the cells with added rabbit complement was measured versus time (FIG. 5). At the highest antibody concentrations complete modulation occurred within 3 hr. That is, the addition of complement to cells preincubated with mAb M195 for 3 hr resulted in no killing. Modulation was incomplete in cells exposed to lower mAb IgG concentrations. Other studies (experiment 3 below) demonstrated that the modulation occurred via antigen internalization after antibody binding.

Biochemical Nature of the M195 Antigen. Treatment of HL60 cells with 100° C. for 1 min eliminated all binding activity in radioimmunoassays and rosetting assays. This suggested that the antigen epitope is carried on a protein. However, treatment with trypsin, protease, and neuraminidase had no effects on binding of mAB M195 to HL60 cells. These experiments, therefore, did not confirm the biochemical nature of the antigen. Repeated attempts to immunoprecipitate the antigen for $^{35}$S-methionine-labeled cells or cells surface-labeled with iodine-125 using lactoperoxidase were unsuccessful. Wester immunoblotting on HL60 extracts were also negative. Although we were unable to identify the target, other data shown in Experiment 2 reference 109 indicated that the antigen was carried on the CD33 protein.

DISCUSSION

This experiment details the specificity of a new mouse mAb, M195, which is reactive with myelogenous leukemias, early myeloid cells and some monocytic cells. Qualitative and quantitative analyses of the mAb's binding, its biological activity, and its immunological functions are described.

Since two potential uses of M195 are diagnosis and in vivo therapy of ANLL, a comprehensive definition of its reactivity with all tissues and cells of the body was undertaken. Several assays were used in the specificity analysis of M195 on fresh cells and cell lines. Rosetting assays which are sensitive enough to detect 1 ng of mAb M195 per ml were used initially for specificity analysis. Direct radioimmunoassays using iodine-125 IgG and F(Ab)'2 were used next in order to quantitate the number of antigen sites expressed on various positive cells. The F(Ab)'2 has the advantage of defining non-Fc receptor binding quantitatively. Finally, a complement fixation assay was used to analyze reactivity. Since biological activity after binding to antigen in an appropriate fashion is required in this assay, the effects of nonspecific binding are reduced. Indirect immunofluorescence followed by confirmation with indirect immunoperoxidase assays were used to define M195 antigen expression on a broad spectrum of normal tissues. These results supported data obtained from the rosetting and absorption analysis on cell lines. Because the tissues were frozen sectioned and fixed, binding to cytoplasmic as well as membrane antigen could be detected in these assays.

M195 was found to bind specifically only to myeloid cell lines and monocytic cells. Lymphoid cells, including peripheral blood T and B cells, lymph node, spleen, and bone marrow cells, T and B cell lines representing pre-B, early B, B, and late B cell stages and T cell leukemias, and activated fresh B and T cells, did not express the M195 antigen. Red cells and platelets were also negative. Among 95 nonhematopoietic cell lines and nonhematopoietic tissues, no adult tissues were reactive with M195. The presence of myeloid antigens in the cytoplasm of choriocarcinoma cells but not normal trophoblast has been reported (110), but its significance is unknown.

With the myelomonocytic lineage, the distribution of M195 antigen was even further restricted. Polymorphonuclear leukocytes were not reactive nor could significant binding be demonstrated in normal bone marrow mononuclear cells. A small percentage of cells from the peripheral blood mononuclear cells from patients with chronic myelogenous leukemia were positive. These samples contain largely granulocytic precursors up to the band stage. The lack of reactivity with polymorphonuclear leukocytes and this slight reactivity with CML suggests that the vast majority of mature and precursor myeloid cells do not express M195 antigen. In contrast, myeloid leukemia lines and fresh myeloid leukemias were strongly positive. Cell lines representing the earliest myeloid cells or erythroid cells were either negative or less positive than the myeloid cell lines representing later leukemias. These data place the M195 antigen expression to cells in the early to middle part of myeloid differentiation: the antigen is not present at first and is lost as the cells mature toward granulocytes.

Among monocytic cells, M195 reacted with both monocytic leukemia lines and a fraction of mature peripheral blood adherent cells. It was present on the HL60 variant, IF10, and in reduced amounts after monocytic differentiation of IF10 with vitamin D3 and phorbal esters. Likewise, AMOL blasts contained about 10,000 sites (Experiment 2) compared to macrophages with 5000 sites. Therefore, like its expression on granulocytic precursors, the expression of the M195 antigen or monocytic cells appears to be maturation dependent.

Analysis of quantitative binding to HL60 cells gave an avidity of binding of the M195 IgG of $3 \times 10^9$ liters/mol. Binding was saturable and cell number dependent. These data showed that positive cell lines expressed about 10,000 antigen sites per cell. Therefore, M195 was rather weakly expressed compared to many other cell surface antigens. Although we have been unable to identify the target antigen of mAb M195, several of its features suggest it is a polypeptide. The antigen is heat labile; there are small numbers expressed on the surface. The antigen is rapidly modulated after antibody binding, and the antigen was detected by an IgG2a (which is this laboratory rarely identify carbohydrate).

The extremely restricted expression of this antigen among the cell types tested, the biochemical features noted above, including rapid modulation and internalization, and the small number of sites per cell all suggested that the M195 target may be a receptor important in growth and differentiation of myeloid progenitors. However, studies of the effects of M195 alone on the growth of myeloid cell lines, peripheral blood mononuclear cells (data not shown), and colony forming units (109) have not so far shown any stimulating or inhibiting effects of the mAb.

mAbs reactive with restricted myeloid antigens may be useful in a least four areas.

A) Study of the Growth and Differentiation of Myeloid and Monocytic Cells. Of the many antigen and antibody systems that have been described in myelomonocytic differentiation, three systems which have defined different states of myeloid maturation have been most widely studied: the CD34 system (mAbs MY10, 12.8, 3C5) (42–44) which identifies a gp115 found on the earliest hematopoietic progenitors, both lymphoid and myeloid, and which rapidly disappears upon differentiation is also found on some non-hematopoietic tissues including endothelium. mAbs to this antigen have been used to purify progenitors for reconstitution of bone marrow (42). The CD33 antigen system (mAbs MY9, L4F3, L1B2) (47–50) identifies a gp67 (41) restricted to early myeloid and monocytic cells. It is absent from the earliest hematopoietic progenitors and other normal tissues and has been used to eliminate leukemia cells, while sparing the ultimate progenitors, from bone marrow. The CD15 antigen system (multiple mAbs) identifies the Lewis X antigen found on granulocyte colonies from the day 7 stage on and increases expression as cells mature to the polymorphonuclear cell. The antigen is also widely distributed throughout normal tissues (111).

The distribution of the M195 antigen detailed in this paper shows it to fall into the myelomonocytic-restricted second category. Competition binding studies and binding to CD33 transfectants (discussed in Experiment 2 and in reference 109) demonstrated that M195 was carried on the CD33 protein. However, cotyping on fresh leukemias showed that the antigen detected by mAb M195 was not identical to the other CD33 antigens (109).

B) Diagnosis of Hematopoietic Neoplasms. mAbs useful in diagnostic applications must be lineage specific, but not necessarily stage specific. For this reason, the CD34 antigen which is also present on lymphoid cells is less useful than the myelomonocytic antigen systems CD13 and CD15 or the monocytic specific antigens CD14 (50, 112, 113). M195 was restricted to myelomonocytic cells and is useful in the diagnosis of ANLL.

C) Purging of ANLL from Bone Marrow. In order to be useful in bone marrow purging, in addition to being myelomonocytic specific, the mAb must spare the ultimate progenitor cell. Reactivity with other tissues outside of the bone marrow is not important. The ability to fix complement is important but new methods to kill cells with toxins (114) or remove them with magnetic beads (115) may reduce this requirement. CD15 antibodies have proven most useful in this application and are in clinical trials currently (36). CD33 antibodies may be even more useful, if adequate recovery of the bone marrow progenitors can be assured. M195, which rapidly and efficiently kills leukemic cells with rabbit complement, can be successfully applied to this problem. (see Experiment 5). Because the antigen can also be found on clonogenic neoplastic cells, the mAb can also be used to treat lymphoid neoplasms.

D) Therapy with mAb in Vivo. This application is most difficult as it optimally requires limited reactivity with normal tissues, in addition to the criteria described above. Of the many antigen systems described for myelomonocytic cells, CD33 appears most suited for this application in vivo. M195 may be used in application. However, because of M195's demonstrated lack of cytotoxicity in the presence of human complement or PBMC in vitro the mAb should preferably carry a cytotoxic isotope or toxin to be most effective. Since the antigen and antibody are rapidly internalized, this therapeutic modality is feasible.

EXPERIMENT 2 (Ref.a)

In experiment 1 we described a mouse monoclonal antibody, M195, which detects an antigen found on early myeloid cells, monocytes, and ANLL cells but not on cells of other hematopoietic or nonhematopoietic lineages (18). The antigen described has several features in common with the myelomonocytic antigen CD33 (13, 14) which is found on early myeloid cells and ANLL cells but not on the ultimate progenitor cells (119), a characteristic which may allow selective killing of ANLL cells (119). In this study, we describe the specific reactivity of M195 with ANLL among 227 different fresh hematopoietic neoplasms, The reactivity was similar but not identical to that of MY9 (CD33). Cross-blocking of the binding of these two antibodies to target cells was found. In combination with MY9, M195 showed specificity in diagnosing ANLL by flow cytometry of clinical specimen. M195 bound to most CFU-GM, as measured by colony forming assays. This pattern of reactivity of M195, together with its lack of reactivity with adult tissues (118) make mAb M195 useful in therapeutic trials in humans.

MATERIALS AND METHODS

Monoclonal Antibodies. M195, a mouse IgG2a, was prepared in this laboratory as described in the Experiment 1 (above). The following mAbs were purchased from Coulter Immunology (Hialeah, Fla.): MY9, an IgG2b, (CD33); B4, and IgG1 (CD19); B1, an IgG2A (CD20); $I_2$ or $I_3$, IgG2As (anti-HLA-DR); MY4, an IgG2b (CD14); and MY7, an IgG2b (CD13). These were either obtained as fluorescein isothiocyanate conjugates or pure immunoglobulins. The following mAbs were purchased from Becton-Dickinson (Mountain View, Calif.): MY10, an IgG1 (CD34) and goat anti-mouse Ig fluorescein isothiocyanate conjugate of F(ab)'2. L4F3, IgM (CD33) ascites was the gift of Dr. Irwin Berstein. M31, IgM, (CD15) and OKB7, IgG2B (CD21) from a hybridoma provided by Ortho Biotech (Raritan, N.J.) were prepared in this laboratory.

Flow Cytometry. Five million fresh live mononuclear cells from bone marrow or blood from patients on the Hematology-Lymphoma Service at Memorial Hospital were incubated in 0.1 ml final volume with the fluorescein conjugated monoclonal antibodies for 30 min at 4° C. and then washed twice and fixed with 0.1% paraformaldehyde before analysis. For indirect immunofluorescence, after the primary antibody incubation for 30 min at 4° C., 50 µl of goat anti-mouse fluorescein conjugate were added for 30 min, followed by washing and fixing. In some samples, whole blood was analyzed by direct immunofluorescence using the Q prep method (Coulter). Ten thousand cells were analyzed on either an EPICS C or an EPICS profile (Coulter) flow cytometer. Blasts were gated for analysis. Samples containing greater than 25% positive cells (using an isotype matched control Ig to designate the upper limit of negative fluorescence intensity) were scored as positive.

Radioimmunoassays. M195 IgG2a was purified by protein A affinity chromatography, radiolabeled with iodine-125, and used in direct radioimmunoassays on live leukemia and bone marrow cells as described before (118). M195 was labeled to 2–10 µCi/µg protein. Specific binding was determined by subtracting the amount of M195 IgG2a bound in the presence of an excess of unlabeled M195 IgG2a. Non-specific binding was about 400 pg per million cells (1600 sites per cell). Binding at this level or below was therefore considered insignificant.

Morphological Designation of Leukemias. Acute leukemias in patients on the Leukemia Service at Memorial Hospital were classified according to the French-American-British (FAB) criteria (120). Undifferentiated cells with negative histochemical stains which did not appear to be lymphoid and which did not meet FAB criteria for other diagnoses were classified as M0 (two cases only). Bone marrow aspirates and peripheral blood smears were stained with McNeil's tetrachrome (Polyscience, Warrington, Pa.) for morphology. Histochemical analysis included staining with Sudan black B and/or peroxidase and periodic acid Schiff, alphanaphthylbutyrate and ASD chloroacetate esterase, acid phosphatase, terminal deoxynucleotidyl transferase (Tdt). Potential B cell neoplasms were analyzed by mouse red cell rosetting and by indirect immunoperoxidase for immunoglobulin products. The presence of the sheep red blood cell receptor on T cells was determined by rosetting at 37° C. and 4° C. (and by monoclonal antibody by flow cytometry).

Determination of Bone Marrow Colony-forming Units. Bone marrow mononuclear cells were assayed for colonies derived from CFU-GM, CFU-GEM, and BFU-E as described (22). Cultures consisted of Iscove's modified Dulbecco's medium (Gibco, Grand Island, N.Y.) with 24% fetal calf serum, 0.8% deionized bovine serum albumin (Sigma Chemical, St. Louis, Mo.), $10^{-4}$ M 2-mercaptoethanol (Sigma Chemical), 1 U partially purified human urinary erythropoietin (49 U/mg) (Toyobo, New York, N.Y.), 10% MO T cell line conditioned media, and 1.3% methylcellulose. Cultures were prepared in quadruplicate and scored on days 7 or 14. In some assays, adherent cells were depleted first by plastic adherence at 37° C. for 90 min. Antibody mediated complement cytotoxicity of colony forming units was determined by incubating the marrow mononuclear cells first in excess monoclonal antibody (10–100 µg/ml) and low toxicity baby rabbit complement (Pel freeze), at a final dilution of 1:8, for 30 min at 37° C. followed by two washes with media. Alternatively, human serum was used as a complement source.

Preparation of Purified Normal Progenitor Blasts. Normal bone marrow cells were depleted of accessory and maturing cells to obtain enriched populations of progenitors by negative selection using density separations and a panel of monoclonal antibodies followed by immune rosetting or panning as described (22). The 12 antibodies reacted with cell surface antigens present on mature T, B, myeloid, and monocytic cells. Cells were then frozen in liquid $N_2$, and thawed once, then reseparated on Ficoll-Paque (Pharmacia, Piscataway, N.J.) before use.

RESULTS

Distribution of M195 on Hematopoietic Neoplasm. The binding of mAb M195 to mononuclear cells from 227 patients as measured by flow cytometry is shown in Table 1. M195 was found on the majority of myeloblastic leukemias; 80% of the positive ANLL cases had greater than 50% of cells positive for M195. Forty percent of positive cases had greater than 75% of cells positive for M195. Lymphoid leukemias, lymphoproliferative disorders, and other nonmyeloid samples were virtually always negative (4% of cases positive).

A quantitative analysis of the total number of binding sites on several of the positive hematopoietic neoplasms was conducted by radioimmunoassay. A previous study (118) showed that myelomonocytic leukemia cell lines expressed approximately 10,000 antigen sites per cell. The same quantity was seen on fresh ANLL cells from several patients (FIG. 6). Lymphoid leukemias and lymphomas, and chronic myclogenous leukemia (CML) cells in chronic phase did not express antigen on their surfaces.

TABLE 1

Distribution of M195 on Hematopoietic Neoplasms By Cytometry[a]

|  | No. Tested | No. Positive | (%) |
|---|---|---|---|
| Acute nonlymphoblastic leukemia | 54 | 34 | (63) |
| Tdt-positive cases only | 10 | 3 | (30) |
| Chronic myelogenous leukemia-Accelerated and myeloblastic phase | 7 | 7 | (100) |
| Total myeloid, blastic cases | 61 | 41 | (67) |
| Chronic myelomonocytic leukemia | 3 | 3 | (100) |
| Myelodysplastic syndromes | 25 | 12 | (40) |
| Chronic myelogenous leukemia (chronic) | 17 | 7 | (41) |
| Acute lymphoblastic leukemia: |  |  |  |
| Calla + | 33 | 4 | (12) |
| Calla − | 8 | 0 |  |
| T-ALL | 5 | 0 |  |
| Chronic myelogenous leukemia-Lymphoblastic phase | 5 | 0 |  |
| Total lymphoid, blastic cases | 51 | 4 | (8) |
| Lymphoproliferative disorders (T + B) | 19 | 1 | (5) |
| Normal, nondiagnostic, and other | 51 | 0 |  |
| Total cases |  | 227 |  |

[a]Conducted as described in the Materials and Methods.

The expression of M195 was compared to the FAB classification of ANLL (Table 2). M195 was expressed in all subclasses of ANLL except M0 and M6. Since there were very few leukemias of these two classes, the significance of this is not clear. However, when both the M0 and M1 classes were pooled, only 3 of 14 (23%) were positive compared to 30 of 44 M2, M3, or M4 leukemias (68%).

TABLE 2

Distribution of M195 Antigen among FAB Morphological Subgroups of AML

| FAB Group | No. Tested | No. M195-Positive | (%) |
|---|---|---|---|
| M0 | 2 | 0 | (0) |
| M1 | 12 | 3 | (25) |
| M2 | 24 | 15 | (63) |
| M3 | 5 | 5 | (100) |
| M4 | 15 | 10 | (67) |
| M5a | 5 | 3 | (60) |
| M5b | 18 | 8 | (44) |
| M6 | 2 | 0 | (0) |
| M7 | 1 | 1 | (100) |

Tdt-positive ANLL (>320 ng/$10^8$ cells) also tended to be M195-negative (30%) compared to the Tdt-negative myeloid leukemias (74%). These data supported the suggestion from our earlier paper on cell lines that the M195 antigen was more highly expressed on early committed granulocytic precursor cells than on more undifferentiated earlier myeloid cells (118).

M195 was found on about a third of CML samples in chronic phase, all CML samples in myeloblastic or accelerated phase but not on lymphoblastic CML cells (Table 3A). Four of 46 acute lymphocytic (ALL) leukemias were M195-positive (Table 3B). These ALL samples were CALLA-positive pre-B leukemias. The total number of cells positive for M195 in these samples was rather low: 26%, 32%, 39%, and 42%. Other markers are shown for comparison. MY9 was present on five pre-B leukemias, with 27%, 28%, 35%, 35%, and 62% MY9-positive cells; four of these were different from those that were M195-positive. One case was 28% MY9-positive and 42% M195-positive. MY9 was also found on one of five cases of lymphoblastic CML (Table 3A).

TABLE 3A

Immunophenotype of Chronic Myelogenous Leukemia at Memorial Hospital[a]

| | No. tested | M195 | My9 | My10 | My7 | My4 | Calla/B4 | Ia |
|---|---|---|---|---|---|---|---|---|
| CML chronic phase | 17 | 41 | 41 | 19 | 18 | 6 | 6 | 24 |
| CML accerlated and myeloblastic | 7 | 100 | 70 | 100 | 86 | 28 | ND | 86 |
| CML lymphoblastic | 5 | 0 | 20 | 100 | 50 | 0 | 80 | 80 |

TABLE 3B

Immunopheotype of Acute Lymphoblastic Leukemias at Memorial Hospital[a]

| ALL type | No. tested | Ia | My10 | B4 | B1 | Calla M195 | My9 |
|---|---|---|---|---|---|---|---|
| CALLA + | 33 | 82 | 58 | 91 | 52 | 12 | 15 |
| CALLA − | 8 | 88 | 88 | 100 | 0 | 0 | 0 |
| T-ALL | 5 | 0 | 0 | 0 | 0 | 0 | 0 |
| Total non-T ALL | 41 | 83 | 64 | 95 | 41 | 10 | 12 |
| Total ALL | 46 | 74 | 57 | 85 | 37 | 9 | 11 |

[a]Conducted as described in Materials and Methods.

A Comparison of M195 with CD33 Antigens. The distribution of M195 appeared similar to that described for CD33-reactive antibodies MY9 and L4F3. The protein target of M195 has thus far eluded detection (118). A comparison of M195 reactivity to other well characterized myeloid markers on the same leukemias is shown in Table 4 (this table does not include 30 leukemias that were not characterized by other markers that were included in Table 2). MY10, MY7, and MY4 were distributed among all subtypes in patterns dissimilar to M195. MY9 was strikingly similar to M195 in its pattern of distribution. An analysis of the concordance of M195 and MY9 in the flow cytometric studies on fresh, acute blastic leukemias (lymphoid and nonlymphoid) is shown in Table 5. In 93 cases of ANLL or acute lymphoid leukemias, either both markers were positive or both were negative. In 19 cases the binding differed, resulting in a concordance rate of 83% overall. This high, but not complete, concordance suggested that the M195 antigen might be related to or coexpressed with the CD33 antigen.

TABLE 4

Immunophenotype of FAB Subgroups of AML at Memorial Hospital[a]

| | No. | % Testing Positive for: | | | | |
|---|---|---|---|---|---|---|
| Group | tested | My10 | My7 | My9 | M195 | My4 |
| M0 | 2 | 100 | 100 | 0 | 0 | 0 |
| M1 | 5 | 80 | 50 | 60 | 40 | 0 |
| M2 | 15 | 67 | 33 | 73 | 73 | 7 |
| M3 | 4 | 100 | 50 | 100 | 100 | 75 |
| M4 | 10 | 70 | 40 | 80 | 70 | 44 |
| M5a | 3 | 100 | 33 | 100 | 67 | 0 |
| M5b | 12 | 58 | 45 | 75 | 58 | 17 |
| M6 | 2 | 50 | 100 | 50 | 0 | 0 |
| M7 | 1 | 100 | 0 | 100 | 100 | 0 |

[a]Conducted as described in Materials and Methods.

TABLE 5

Concordance Data for M195 and My9 amount 112 Blastic Leukemias

| Reactivity Pattern | No. of Cases |
|---|---|
| My9 + and M195 + | 38 |
| My9 − and M195 − | 55 |
| My9 + and M195 −, or My9 − and M195 + | 19 |
| Over all concordance | 83% |

Cross-blocking experiments using iodine-125-labeled M195 IgG or F(Ab)'2 binding to HL60 leukemia cells in the presence of excess concentrations of various immunoglobulins are shown in FIG. 2. Both MY9 and L4F3 (CD33-reactive), as well as the original M195 IgG, blocked binding of the $^{125}$I-M195. MY7 (CD13), M31 (CD15), and OKB7 (CD21) did not inhibit binding. These data further confirmed the association between the M195 antigen and CD33 antigens. In other experiments (not shown) excess unlabelled M195 was able to block binding of about 50% of FITC-labeled MY9 to HL60 cells as measured by flow cytometry.

mAb M195 was also tested by Dr. T. Look (St. Jude, Memphis, Tenn.) for reactivity with NI-3T3 cells transfected with the DNA from myeloid cells and expressing the CD33 antigen (121). Both L4F3 (CD33) and MY9 (CD33) are reactive with these cells; M195 was reactive as well. This result, when taken in context with the nonidentical concordance data shown above, suggested that the M195 antigen was carried on the p67 (CD33) but was not the same as the previously described CD33 antigen epitopes recognized by L4F3 and MY9.

Diagnostic Utility of M195. MY9 is widely regarded as the standard marker for ANLL (122,123). We compared the diagnostic utility of MY9 with M195 either alone or together on 81 blastic leukemias of either myeloid or lymphoid origin (Table 6). Eighty-four percent of ANLL expressed either M195 or MY9, but each antibody alone failed to identify more than a quarter of cases. Among lymphoid cases either MY9 or M195 was occasionally expressed, but both antibodies were expressed together only once. In this case the reactivity was weak: 28% MY9+ and 42% M195+. Thus, the presence of both M195 and MY9 positivity on a leukemia sample had 98% specificity in defining that leukemia as ANLL.

TABLE 6

Diagnostic Utility of M195 and My9 among Blastic Leukemias.

| | Positive Cases with the Indicated Marker(s) | | | |
|---|---|---|---|---|
| | M195 Alone | My9 Alone | Both M195 and My9 | Either M195 and My9 |
| Sensitivity[a] in 61 Myeloblastic cases | 67%[a] | 74% | 67% | 84% |
| Specificity[c] in 51 lymphoblastic cases | 8% | 12% | 2% | 20% |

[a]Antibody(s) should be positive in all cases.
[b]Percent of cases positive by flow cytometry.
[c]Antibody(s) should be negative in all cases.

Expression of M195 on Hematopoietic Colony-forming Cells. The expression of M195 on leukemia cells, but not on mature nonadherent peripheral blood cells nor on any detectable nonadherent bone marrow cells (118), suggested that M195 might be expressed on a small group of hematopoietic progenitors. The expression of M195 antigen on hematopoietic progenitors was studied by analyzing the recovery of bone marrow colonies after treatment of bone marrow mononuclear cells with M195 and rabbit complement (Table 7). Complement alone, antibody alone, and no antibody or complement treatments were used as negative controls. Antibody to human IA antigen (gift of Dr. J. D. Griffin) was used as a positive control. The number of CFU-GEMM recovered was not sufficient to obtain statistically significant data. In three of four experiments, M195 and complement eliminated almost all of the 14-day CFU-GM; burst forming unit erythrocytes were also killed, although the average recovery was somewhat higher.

TABLE 7

Recovery of Colonies after Treatment with Antibody and Complement

| | % Recovery of the Following Colonies | | |
|---|---|---|---|
| Treatment | Day 7 CFU-GM | Day 14 CFU-GM | BFU-F |
| Nil | 124[a] (111, 136)[b] | 126 (139, 104, 111, 110) | 103 (143, 83, 115, 71) |
| M195 alone | 108 (97, 120) | 124 (126, 181, 93, 98) | 107 (141, 114, 98, 74) |
| Complement alone | 100[c] | 100 | 100 |
| M195 plus complement | 6 (10, 1) | 17 (0, 60, 3, 6) | 33 (8, 77, 6, 40) |
| Anti-IA plus complement | 0 (0, ND[d]) | 1 (0, 2, 0, ND) | 6 (5, 11, 1, ND) |

[a]Mean of all experiments shown.
[b]Percent recovery of an individual experiment.
[c]The "complement alone" treatment was considered to be 100% recovery, and other data on this chart were normalized to that value. Plating efficiency was between 0.10 and 0.15 percent.
[d]ND = Not determined.

In order to determine the extent of expression of M195 on early hematopoietic progenitors, radioimmunoassays were conducted on highly purified blasts. The cells used were isolated by negative selection with a panel of 12 monoclonal antibodies and immunorosetting or panning followed by freezing and thawing once (22). These cells are morphologically blasts and represent a progenitor cell population 50–100-fold purer than bone marrow mononuclear cells. Five to fifteen percent of these cells typically form myeloid and erythroid colonies.

No binding of $^{125}$I-M195 above background was found in testing three different samples of these normal, early blast cells. A small percent of positive cells could escape detection using this assay.

Because these data suggested that M195 antigen was expressed on a minor population of bone marrow cells responsible for CFU-GM colonies, we attempted to identify these cells by positive selection with panning, immunomagnetic bead separation, affinity sepharose bead separation, and fluorescence-activated cell sorting. None of these methods selected out a M195-positive subpopulation. This may be due to weak antigen expression, antibody affinity, or other unknown problems.

Effects of M195 on Bone Marrow progenitors in the Presence of Human Complement. Because we anticipated use of M195 in vivo for therapy of ANLL, we studied the effects of M195 on CFU-GM and 5FU-E from normal bone marrow in the presence of human serum as a complement source (Table 8A). No killing of CFU-GM or BFU-E was seen at 14 days. The effect of the continued presence of M195 in bone marrow culture was also studied by adding the antibody to the methyl cellulose at days 1 and 5 after plating, with no added complement (Table 8B). These experiments were done to determine if the antibody had a growth stimulatory or inhibitory effect on progenitor cells in the marrow. No effects were seen. Similar growth studies of peripheral blood mononuclear cells and HL60 leukemia cells were also negative.

TABLE 8A

Effects of M195 on Hematopoietic Stem Cells in the Presence of Human Complement[a]

| Treatment | No. of Colonies, Day 14 | |
|---|---|---|
| | CFU-GM | BFU-E |
| None | 116 (100%)[b] | 154 (100%) |
| Complement (C') alone | 102 (100%) | 121 (100%) |
| M195 | 132 (113%) | 158 (102%) |
| M195 + C' | 141 (138%) | 127 (105%) |

TABLE 8B

Effect of the Continued Presence of M195 on Colony Forming Cells[c]

| Treatment | No. of Colonies, Day 14 | |
|---|---|---|
| | CFU-GM | BFU-E |
| Nil | 125 (100%) | 188 (100%) |
| M195 | 124 (99%) | 168 (89%) |

[a]Human serum was added at a final dilution of 1/6 as described for rabbit complement in Materials and Methods.
[b]Quadriplicate control plate results are normalized to 100%.
[c]M195 IgG was added directly to growing cultures as described in Materials and Methods.

DISCUSSION

This experiment describes the distribution of mAb M195's binding on fresh leukemia cells and early hematopoietic progenitors. we showed that the M195 antigen was present on myelomonocytic leukemia cells and a fraction of monocytes but was not detectable on more mature myeloid cells present in the bone marrow or peripheral blood nor on nonhematopoietic cells and tissues (118). In this experiment we extend the description of the M195 antigen and directly compare it to other well-characterized myeloid and monocytic antigens. Among 227 fresh hematopoietic samples studied, M195 antigen expression was largely restricted to differentiated ANLL. Undifferentiated and Tdt-positive ANLL were less likely to display antigen. However, FAB classification did not correlate specifically with M195 expression.

Quantitative analysis by radioimmunoassay showed that about 10,000 sites were expressed on the cell surface of ANLL cells. Our studies (118) have demonstrated rapid modulation of these sites after antibody binding.

Several antigens are currently used to diagnose ANLL by flow cytometry. Among these, CD33 antibodies, MY9 (14), and L4F3 or LIB2 (13), appear to be most widely and most specifically distributed on ANLL. M195 antigen was concordantly expressed with MY9 on 83% of cases. Moreover, although neither antigen was expressed on 100% of ANLL, the combination of both M195 and MY9 could be used to diagnose ANLL with 98% specificity if both were expressed on a leukemia sample. We are currently using this combination to aid in the diagnosis of acute leukemias at Memorial Hospital.

The close coexpression of M195 and MY9 suggested that M195 might bind to the CD33 protein target [p67] (121). Efforts to identify the M195 target have been unsuccessful (118). Blocking experiments shown here demonstrated probable identity of the M195 target with the CD33 protein. Moreover, binding of M195 and CD33 DNA transfectants was shown. Despite these data, since flow cytometry data showed nonidentical concordance with MY9, it is likely that M195 does not bind to the same CD33 epitope as MY9 or L4F3.

Although M195 antigen was found on a greater percentage of ANLL samples of the FAB classifications M2, M3, and M4 than on other types, the presence of M195 binding could not be used to predict morphology or vice versa. Other studies comparing immunophenotype with morphologic phenotype have come to similar conclusions since there was considerable overlap of markers into each type of ANLL (123–125). Some discrimination of monocytic from myeloid ANLL has been shown (123,126), however.

The CD33 antigen is expressed on early myelomonocytic progenitors cells (13,14 Ref.a), but not on the ultimate progenitors (119). This restriction has allowed selective purging of ANLL cells from bone marrow while still permitting regrowth of normal cells in selective cases (127 see Experiment 5). M195, as expected, was expressed on CFU-GM and to a lesser extent on BFU-E. Since, like MY9 and L4F3, M195 readily kills cells with rabbit complement, it is useful as a purging agent in ANLL.

Radioimmunoassays with M195 on highly purified early blasts did not detect significant antigen expression. Because the radioimmunoassay could miss M195 expression on small subpopulations within this group of cells, longterm marrow cultures were done (see Experiment 5) to help further define and confirm this finding. Based on the data here and in Experiment 1 the distribution of the M195 antigen among hematopoietic differentiation appears similar to that described for other CD33 antigens (13,14). This includes early committed myeloid progenitors, but not the earliest colony forming cells (see Experiment 5)(17,18 Ref.a).

The M195 antigen is not expressed on adult human tissues. Therefore, in addition to its use as a diagnostic marker of ANLL and as a purging agent, M195 can potentially be used as a therapeutic agent in vivo. Since the antibody does not have in vitro cytotoxic effects alone or in the presence of human serum as a complement source, it is not likely to cause lysis of ANLL cells. However, upon binding of mAb M195, the antibody is rapidly internalized (Experiment 3), and thus the application of mAb M195 as a carrier of toxins or isotopes to ANLL cells in vivo is feasible.

EXPERIMENT 3

In this experiment, we focus on the impact of modulation and mAb internalization and release on the delivery of radionuclide into tumor cells. We investigated the behavior of two prototype radionuclides, radioiodine and radioindium, when attached to mAbs currently under evaluation at Memorial Sloan-Kettering Cancer Center in Phase I clinical trials. Iodine-125 serves as a prototype for all halides such as $^{77}$Br, $^{123}$I, $^{131}$I, $^{211}$At, and $^{124}$I. $^{111}$In serves as a prototype for all radiometals such as $^{212}$Bi, $^{212}$Pb, $^{90}$Y, $^{186}$Rh, and $^{188}$Rh. The mAbs modulate subsequent to interaction with antigen. Mab M195 is reactive with a 67 KD cell-surface glycoprotein found on most myeloid leukemia cells (128, 129), and is reactive with the Epstein Barr Virus (EBV) receptor, a 140 KD glycoprotein surface receptor expressed on most B-cell lymphoma cells and chronic lymphocytic leukemia (130, 131). In addition, we explored the behavior of a proteolytic digestion fragment of the antibody.

MATERIALS AND METHODS

Cells HL60, a myeloid leukemia cell line, were maintained in log phase growth in RPMI 1640 supplemented with 10% FCS and 10% 1-glutamine at 37° C. in 5% carbon dioxide. Cells were utilized only if the viability (as estimated by trypan blue exclusion) was 95% or greater.

Antibodies M195 is an IgG2a monoclonal antibody (mAb) reactive with a 67 KD cell-surface glycoprotein found on most myeloid leukemia cells (128,129 Ref.c). The antibody was purified from mouse ascites fluid using Protein A affinity chromatography. M195 F(ab')$_2$ was prepared by pepsin digestion of the intact immunoglobulin; OKB7 Fab was prepared by papain digestion.

Radaiodination Intact antibodies and their fragments were labeled with iodine-125 by the chloramine-T method (132). 100 µg of antibody was incubated with 2 mCi of $^{125}$I and 20 µl of a freshly prepared solution of chloramine-T at a concentration of 2 mg/mL in 0.2M phosphate at pH 7.4 for 1 minute at room temperature. The reaction was quenched with 20 µl of a freshly prepared solution of sodium metabisulfite at 20 mg/mL and incubated for 5 minutes. The radiolabeled antibody was purified by exclusion chromatography (Sephadex G25, Pharmacia Inc., Piscataway, N.J.). Further purification of the mAb from free radionuclide was effected by dialyzing the radiolabeled mAb at 4° in phosphate buffered saline (PBS), pH 7.4.

Immunoreactivity of the labeled antibody (that proportion of antibody molecules in a preparation which were capable of binding to antigen) was determined by modifications of previously described methods (132,133) as follows: $10^7$ cells of at least 95% viability at 4° C. were incubated with 5 ng of the radiolabeled antibody for 60 minutes. The percent bound was estimated; the supernatant obtained after centrifugation was transferred to a similar set of cells and the process repeated until binding was no greater than with a control cell line. Immunoreactivity was not less than 65% for M195.

$^{111}$Indium Labeling The intact immunoglobulins were conjugated with diethylene triamine pentaacetic acid (DTPA) as described in reference 134. After conjugation, each antibody was labeled with $^{1111}$In by incubation with $^{111}$In at a pH of 3.0 for 60 minutes at room temperature. The reaction was quenched by increasing the pH to greater than 6.5 using 0.2M metal-free phosphate buffer (pH 7.4). The radiolabeled mAb was purified using a Chelex metal-binding column followed by size exclusion chromatography. Further removal of free $^{111}$In from mAb was accomplished by dialyzing the radiolabeled mAb at 4° in metal-free PBS, pH 7.4. Immunoreactivity of the labeled antibody was comparable to that of the respective radioiodinated antibody.

Radionuclide Internalization 5 million viable cells in 5 mL media were incubated with 5 µg radiolabled antibody, at either 4° C. or 37°. Immediately after addition of the radiolabeled mAb (or fragment) and at several times afterward, 200 µl aliquots from each batch of cells were taken and washed three times. 1.5 mL glycine/sodium chloride (50 mM glycine/HCl, 150 mM sodium chloride, pH 2.8) was added to each pellet. "Total" cell-associated radioactivity was determined in a gamma counter after mixing. The cells were then centrifuged, the supernatant aspirated, and the cell pellet re-counted to determine "internalized" radioactivity. "Cell surface" radioactivity was calculated as the difference between total and internalized radio-activity. This general method has been used to study internalization of other cell surface receptors (72–74). We have confirmed that this direct method measures true losses of antibody from the surface by indirect methods (indirect radioimmunoassay and complement fixation) as well. The percent radioiodine bound to protein in the supernatant was estimated by TCA precipitation of the supernatant; it was never less than 95%. Similarly, protein-bound radioindium was estimated in aliquots of selected supernatants by thin layer chromatography and was always greater than 90%.

Radionuclide Release: 5 million viable cells in 5 mL media were incubated with 5 µg radiolabeled mAb or fragment at 4° for 60 minutes. The incubated cells were then washed two times in media and resuspended to the same volume. Baseline total and internalized radioactivity was determined as described above. Immediately after washing, the washed cells were separated into two parts and kept at either 4° or 37°. Total cell-associated radioactivity and internalized radioactivity were then determined over time as described above.

RESULTS

All experiments were done 2–6 times and all time points were done in duplicate. The mean of two determinations was recorded. Maximal binding of M195 was about 10,000 sites per cell.

Internalization experiments were designed to study changes in the kinetics of binding and cell-associated radioactivity in the presence of excess ambient antibody, a condition which might occur during an antibody infusion in patients. The release experiments were designed to study the same phenomena, after a period of binding, in the absence of ambient antibody which might mimic conditions in vivo following termination of mAb infusion.

$^{125}$I-M195 Internalization and Release (FIGS. 8A–D) At 4°, there were initial increases in the total amount of cell-associated radioactivity, with minimal internalization of $^{125}$I (FIG. 1A). Bound $^{125}$I increased about 4-fold and plateaued by 2 hours, suggesting completion of binding and saturation of sites within this time period. At 37°, there was a similar increase in total cell-associated radioactivity over time as at 4°. In contrast, there was a significant greater increase in the amount of internalized radioactivity over time, with most of the increase being noted in the first two hours. After two hours, the internalized radioactivity stabilized at about a 12-fold higher level than at time 0.

The release experiments for M195 IgG (FIGS. 9C, 9D) showed no significant change in cell-associated radioactivity over time at 4°; the amount of radioactivity in the surface and within the cell did not change over time. At 37°, there was an initial rapid clearance of about 40% of the cell-associated radioactivity. The radioactivity that cleared appeared to be accounted for by net loss from the cell surface. Whether this was direct or via an internalization step cannot be determined from these data. There was an increase in internalized radioactivity with time. Clearance of radioactivity from the cell surface occurred during the first hour, after which the total amount of cell-associated radioactivity stayed constant while the amount of internalized radioactivity increased to plateau toward the end of the experiment.

Figure 8A:
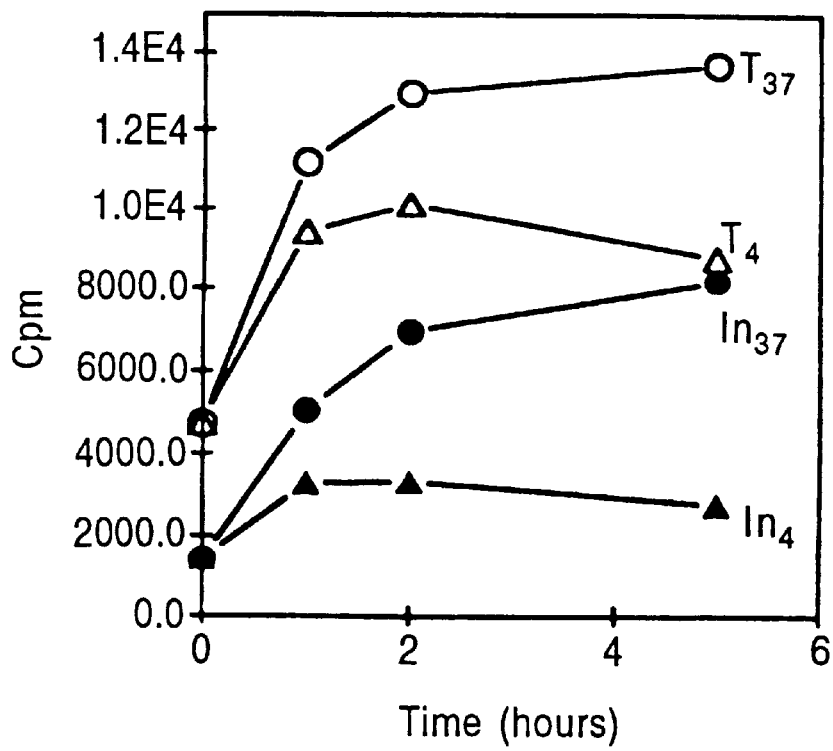
Figure 8B:
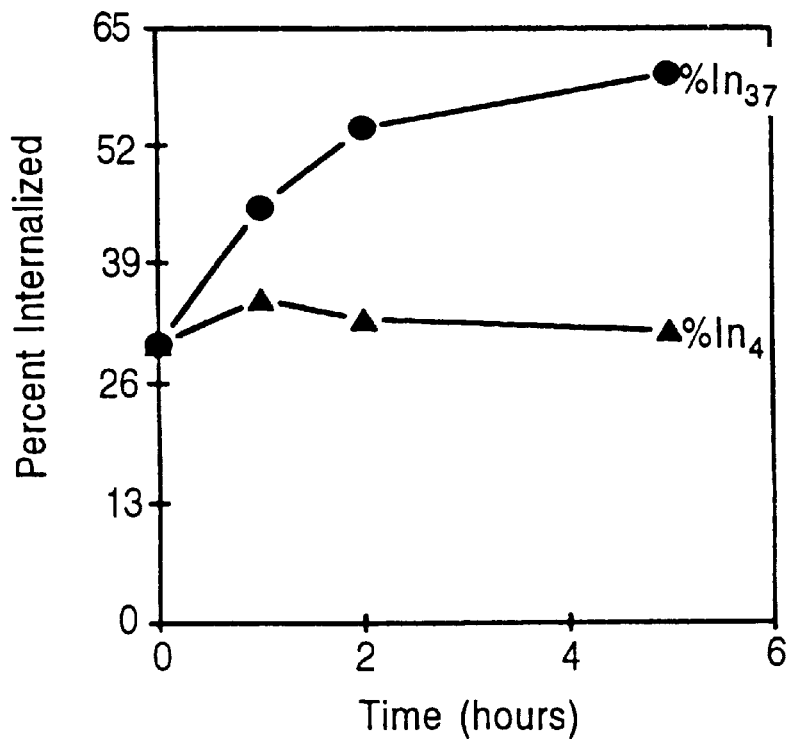
Figure 8C:
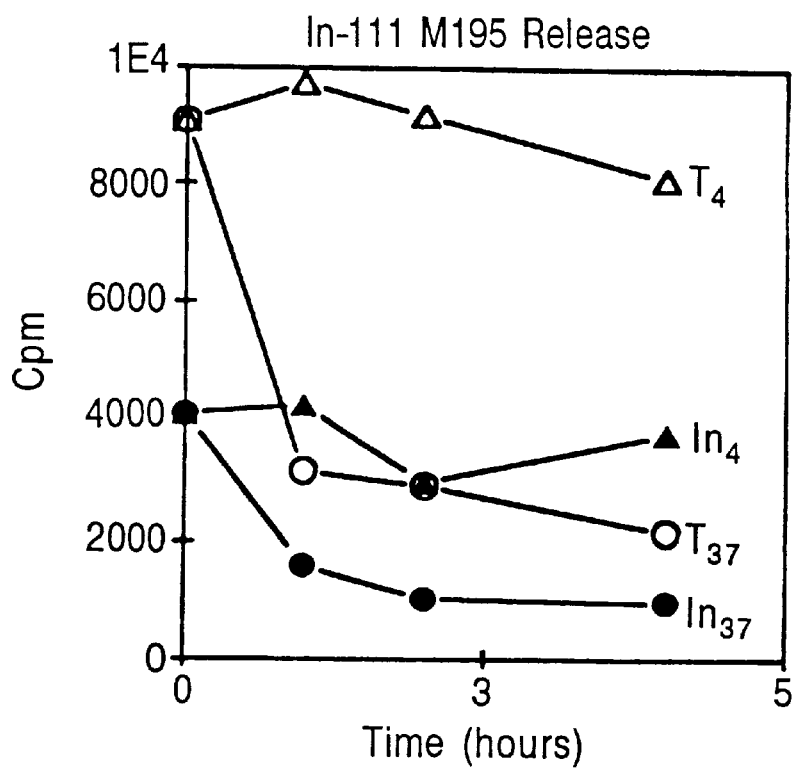
Figure 8D:
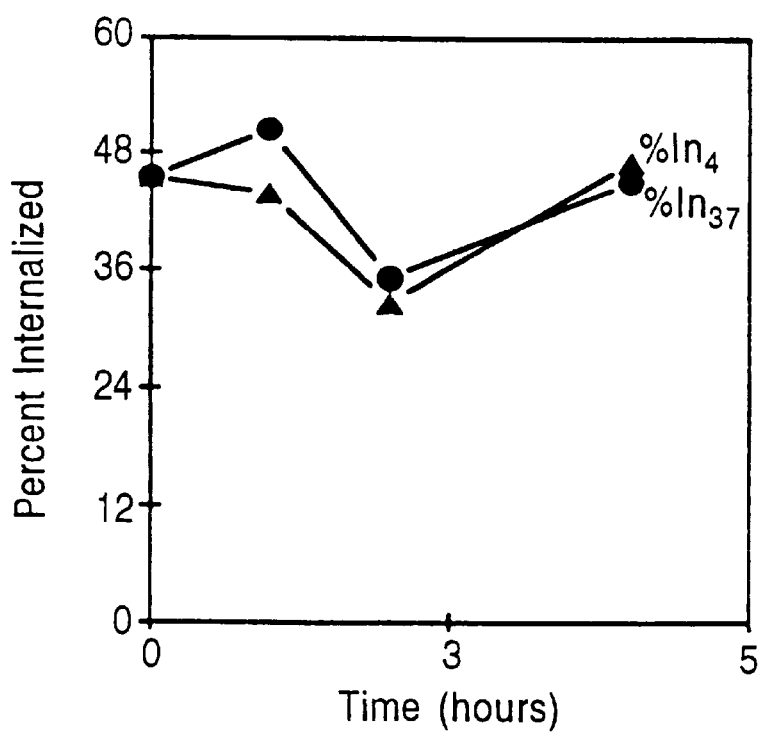
Figure 9A:
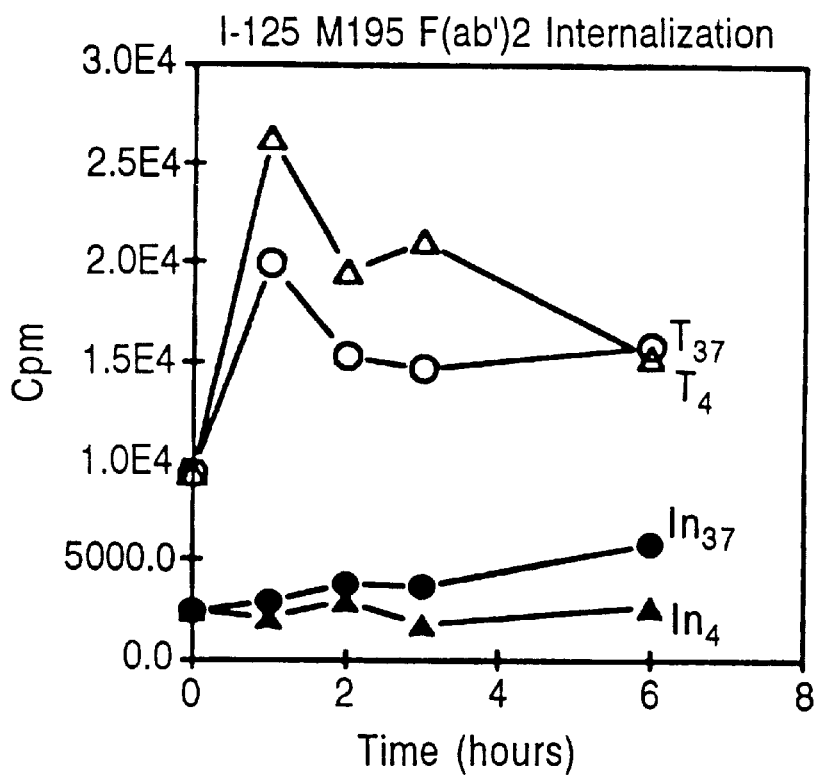
Figure 9B:
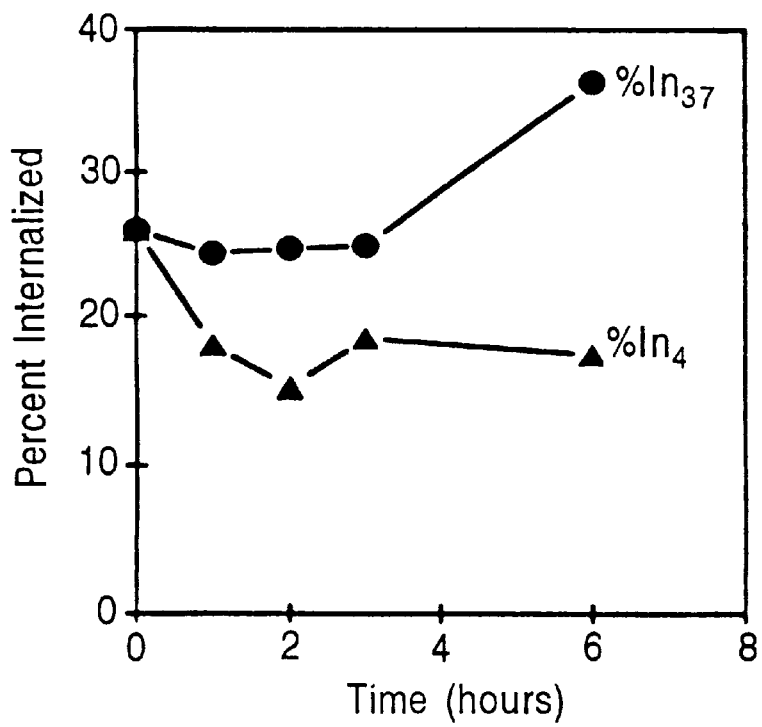

The present of cell-associated radioactivity that was internalized was constant for cells at 4° (FIGS. 8B, 8D). At 37° the percent of internalized radioactivity approached 35% of total cell-associated radioactivity in the presence of excess antibody, and up to 60% in the absence of ambient antibody.

In the presence of surrounding antibody there appeared to be no net loss of cell-associated radioactivity, with increases in the amount within the cell contributing to the increase in percent radioactivity internalized. In contrast, in the absence of ambient antibody (FIGS. 8C, 8D), there was a net loss of total cell-associated radioactivity manifest as a transfer of radioactivity from the cell surface to both the surrounding media and to the cell interior.

This may have occurred either because of internalization followed by release or by an independent direct release of surface-bound radioactivity into the media. This net loss translated to an increase in the percent radioactivity internalized greater than that apparent solely from the increase in internalized radioactive counts. The net result was that after 2 hours, more than half the radioactivity associated with the HL60 cells was intracellular.

$^{111}$In-M195 Internalization and Release (FIGS. 9A–9D) Additional experiments were conducted as above, using $^{111}$In-M195 (FIGS. 2a, b). Large increases in internalized radioactivity occurred over time at 37° as compared to 4° (FIG. 2a). Internalization of $^{111}$In as a percentage was consistently higher than with $^{125}$I, increasing with time, not showing a plateau out to 4 hours, to reach approximately 70% in some experiments. This may be due in part to a greater loss (60%) of total $^{111}$In at 37° (FIG. 9C), perhaps by release of chelated $^{111}$In from surface-bound IgG. In this as well as the $^{111}$In-OKB7 experiments, the background percent internalization was considerably greater than observed with $^{125}$I-labeled antibody, perhaps due to transchelation of $^{111}$In to cellular protein.

In summary, at 4°, when cells would be expected to be metabolically quiescent, there were no major changes in cell-associated radioactivity over time, whether on or in the cell and whether or not there was surrounding antibody present. In contrast, cell-associated radioactivity changed dramatically over time at 37° when the cells are metabolically active.

$^{125}$I M195 F(ab')$_2$ Internalization and Release (FIGS. 10A–10D) In contrast to the findings observed with the intact Ig, with the F(ab')$_2$ the early increase in total cell-associated radioactivity decreased moderately with time. The internalized radioactivity, however, increased gradually with time at 37° while staying relatively constant at 4°. Background (time 0) radioactivity was consistently higher with the F(ab')$_2$. The increase in internalized radioactivity was not as great over time with the fragment as with the intact Ig (26% to 37% with the fragment compared to 6% to 32% with the Ig).

In the absence of ambient antibody, there was rapid decrease in the total cell-associated radioactivity with time at 37%; this was accompanied by a significant, albeit small, decrease in the total amount of radioactivity within the cell; the percent internalized over time at 37° therefore did not increase as much as with the intact Ig.

Because of differences in specific activity of the labeled Ig and fragments and differences in counting efficiency of the two radionuclides among the different sets of experiments, all changes over time in an individual experiment were related to conditions at time 0 to enable us to compare experiments (Table I). Radioactive counts at time (n) were expressed as a percentage of those at time 0 (Cpm$_{(t=n)}$/Cpm (t=0)×100). Several conclusions became apparent.

With M195 Ig, an antibody that rapidly internalizes in the presence of ambient excess antibody (the internalization experiments), there was no significant difference between the changes in amounts of radioindium internalized as compared to the changes in amounts of radioiodine internalized (1130% vs. 1300%). In contrast, the percent losses of radioiodine from the cell in the absence of ambient antibody (the release experiments) were considerably less than the losses in amounts of $^{111}$In. The relative increase in percent internalized was primarily a result of greater loss of cell-associated radioactivity. Radioiodine attached to the fragment cleared at an even faster rate than that of $^{111}$In.

DISCUSSION

As the number of clinical trials employing radioactively tagged monoclonal antibodies for diagnostic imaging or radioimmunotherapy increases, the need for an understanding of the kinetics of antibody binding and internalization of nuclide become increasingly important. Significant differences in binding of $^{111}$In labeled antibody compared to radioiodinated antibody have been demonstrated in vitro and in vivo (66–69). The experiments here attempt to describe some of these differences at the cellular level. We show that internalization of radionuclide into target tumor cells is dependent upon the choice of radionuclide, the antigen-antibody system concerned, and the nature of the antibody used, either intact immunoglobulin or fragment.

Recently, Press et al.(72) compared the binding and degradation characteristics of a panel of radioiodinated antibodies reacting against B-cell tumors. As we have also confirmed here, distinct differences in internalization kinetics were found between mAbs. In addition, we also studied the behavior of intact and fragmented mAbs when labeled with two different prototype radionuclides, $^{125}$I and $^{111}$In. Significant detachment of radionuclide from antibody was not seen at the early time points we studied. This is similar to results observed by Press and associates. Because steady states were reached within 2–4 hours, we did not examine behavior at late time points.

In the presence of excess surrounding antibody, M195 Ig was rapidly internalized by the cell subsequent to interaction with the target antigen. For both nuclides, there were no differences in binding kinetics (Table I). With the F(ab')$_2$, there were minimal changes in total and internalized radio-activity. After ambient M195 Ig or F(ab')$_2$ had been washed away, there was greater loss of $^{111}$n-labeled compared to $^{125}$I-labeled Ig, and much greater internalization with the Ig than with the F(ab')$_2$. We do not know if these differences reflect the minor difference in avidity (3×10$^9$ L/M for the intact Ig compared to 10$^9$ L/M for the F(ab')$_2$).

Internalization and release kinetics of radionuclide labeled to a mAb that is internalized rapidly were not dependent on the nature of the radionuclide used. Radionuclide attached to the intact M195 Ig showed far greater internalization than when attached to its fragment. Studies with the Fab fragment suggested that lack of modulation and internalization may be more apparent in the absence of excess surrounding antibody.

In a clinical trial using M195 (whether diagnostic or therapeutic), intact M195 Ig might be preferable to the fragment, as a significantly greater amount of radioactivity would then be internalized. The K$_D$ of the F(ab')$_2$ is 10$^9$ L/M compared to a K$_D$ of 3×10$^9$ L/M for the intact immunoglobulin; we do not know if the difference in internalization was caused by this small difference in dissociation constants or some other unknown change in antibody binding consequent to creation of the F(ab')$_2$. Although there was greater clearance of $^{111}$In from the cell in the absence of ambient mAb, there was also a significantly greater amount internalized. Since in the absence of ambient antibody there is greater loss of cell-associated radioactivity when $^{111}$In is the radionuclide used, the ideal radiolabel to be used might either be a suitable isotope of iodine or a radiometal depending upon the physical half-life of the radionuclide and the biological half-life of the antibody in the host.

Although the kinetics of binding, internalization, and release are important, the choice of nuclide for clinical therapy trials would also be affected by the physical half-life, emission characteristics, and cytotoxic potential of the radionuclide under consideration, as well as by labeling characteristics and serum clearance. Dehalogenation of iodine-labeled antibody has been described (69), but current methods of chelation also result in detachment of radiometal from antibody in vivo (69) and human trials have not been uniformly successful to date. Progress in new chelation chemistry may solve these problems (135). Moreover, if radionuclides that decay by electron capture are more cytotoxic when internalized into the cell than those that undergo beta-minus decay, then $^{125}$I and $^{123}$I would be candidate radionuclides for therapeutic purposes. A recent report by Woo et al. (65) has shown significant cytotoxicity with $^{125}$I-labeled antibody compared to unlabeled antibody, postulated to be due to cytotoxicity of intranuclear $^{125}$I. We have also seen significantly enhanced growth suppression of $^{125}$I-labeled anti-epidermal growth factor receptor antibody compared to $^{131}$I-labeled or unlabeled antibody in cells expressing increased quantities of the receptor. We are now studying the cytotoxicity of iodine labeled M195 in vitro.

In summary, the choice of both the radionuclide and the antibody form has great impact on the kinetics of radionuclide internalization and retention in target cells and therefore, may be of crucial importance in the design of clinical trials utilizing radiolabeled antibodies. Preclinical studies of cell binding and internalization such as those described here may help suggest an optimal approach for imaging or therapy.

EXPERIMENT 4

A PHASE I TRIAL OF MONOCLONAL ANTIBODY M195 IN ACUTE MYELOGENOUS LEUKEMIA: SPECIFIC BONE MARROW TARGETING AND INTERNALIZATION OF RADIONUCLIDE

MATERIALS AND METHODS

M195. The isolation and characterization of mAb 195 has been reported (88, 89, 91, 136). Purification of clinical grade M195 was done at Sloan-Kettering Institute under IRB approval, essentially as described (137). The final product was tested for the presence of murine viruses, endotoxin, pyrogen, bacteria or fungal contamination, mycoplasma, and DNA. General safety testing was done on mice and guinea pigs. Purity was assessed by silver stained polyacrylamide gels and cation exchange fast performance liquid chromatography.

Radiolabeling. 1.5 mg of M195 was labeled with approximately 5 mCi of iodine-131 (New England Nuclear) using chloramine-T (138) and aseptic pyrogen-free technique. Pure antibody was isolated by exclusion chromatography and filtered through a 0.45 μm filter before clinical use.

Quality Control. $^{131}$I-M195 was tested for the following: specific activity, trichloroacetic acid precipitable $^{131}$I-protein, free iodine-131 by high performance thin layer chromatography, biochemical impurities by high performance liquid chromatography, and immunoreactivity on HL60 myeloid leukemia cells. Doses for injection were greater than 98% free of $^{131}$I and showed immunoreactivities of about 60% in a one step binding assay in antigen excess.

Trial Design. All patients over 18 years of age with relapsed or refractory AML, accelerated or blastic chronic myelogenous leukemia (CML), or chronic myelomonocytic leukemia (CMMOL) were eligible if their leukemic blasts expressed the CD33 antigen by flow cytometry. No restrictions were placed on initial white blood cell counts or platelets, or concurrent use of intravenous antibiotics. All chemotherapy or radio-therapy was stopped four weeks prior to beginning M195. Hydroxyurea was permitted to control peripheral blood counts up to 3 days prior to beginning M195.

Patients were pretreated with Lugol's solution and allopurinol. A total of four daily doses of M195 were administered over 4–6 days. A minimum of three patients were treated at each dose level (1 mg/m$^2$, 5 mg/m$^2$, and 10 mg/m$^2$; times four doses each) by 20 minute infusions. The first dose of M195 in each patient was trace-labeled with $^{131}$I as described above. Physical exam, complete blood counts, coagulation indices, biochemical and electrolyte values were measured daily. Pharmacologic, dosimetric, and radiolocalization data were obtained as described below. Toxicity was assessed according to the common criteria established by the National Cancer Institute (NCI).

This trial was conducted under Institutional Review Board approval after informed consent was given by all participating patients.

Pharmacology and Dosimetry. Heparinized blood samples were drawn 5, 10, 15, 30, 45, 60, 120, 240, 480 minutes after the first M195 infusion and then twice daily for 5 days. Whole blood and plasma were analyzed separately for $^{131}$I and quantitative two exponential decay curves were generated using BLD software (Department of Nuclear Medicine, NIH). Trichloroacetic acid precipitable $^{131}$I and the immunoreactivity of $^{131}$I-M195 with HL60 cells were measured in selected samples of serum as well. Cumulative urine excretion of $^{131}$I was also determined in selected patients. A bone marrow biopsy and aspirate were obtained at 1 hour and at 2–3 days after the infusions. $^{131}$I per gram of bone marrow core and per 10$^9$ Ficoll-Paque (Pharmacia, Piscataway, N.J.) separated bone marrow mononuclear cells were measured. In patients with elevated peripheral blood blasts, $^{131}$I bound to isolated mononuclear cells was also measured. Stained cytospins or smears of marrow or blood mononuclear cells were carried out to assess the percent of leukemic involvement.

Anterior and posterior whole body gamma camera images were obtained daily using a Technicare Gemini II (General Electric, Madison, Wis.). Regions of interest (ROI) were drawn on computer images for determination of cpm using Mirage software (Department of Nuclear Medicine, NIH). Whole body radioactivity measurements were determined at 3 meters as well. Single exponential $^{131}$-I decay curves were generated for whole body, bone marrow, and organs of interest from the data obtained using BLD software. Internalization and release of $^{131}$I-M195 from leukemic blasts over time a vitro and ex vivo were conducted as described below (136).

Serum levels of unlabeled M195 over time were also determined using a sandwich enzyme linked immunosorbent assay (ELISA). Optical densities were converted into protein concentrations using purified M195 diluted into the patient's pre-treatment serum as a standard.

Plasma and whole-bodyplasma ion determinations. The plasma clearance data were integrated and used to determine the non-penetrating plasma dose in rads per mCi administered using MIRD-S factors (139). The total plasma dose was determined by adding the non-penetrating dose to the total body dose. The effective whole-body clearances (described above) were also used with MIRD S-factors to calculate whole-body doses for I-131 and I-123 labelled M195. These estimates were compared with individual determinations using heights and weights to calculate a g-factor (140), with good agreement between both sets of results. Liver doses were determined by analyzing ROI over time on gamma camera scan data acquired in 512×512 mode on the Mirage software system. Effective clearance times were determined with BLD as described above, and cumulative doses calculated using the S-factor methodology (139).

The number of keV deposited in target cells nuclei per injected mCi was determined using the assumptions and procedures of Kassis, et al (141). The decay scheme values for I-123 and I-131 were taken from Brown and Firestone (142). The radioactivity that was incorporated into the cell was assumed to be uniformly distributed within the cytoplasm. The keV per disintegration deposited in the nucleus was calculated and was determined as 0.53 keV per disintegration and 0.54 keV per disintegration for $^{123}$I and $^{131}$I respectively. Doses from the surface or outside of the cell were not calculated.

HAMA. Plasma samples were tested for HAMA beginning 8–10 days after the end of infusions and then every 3–4 weeks using an ELISA essentially as described (15).

Flow Cytometry. Peripheral blood and bone marrow cells were examined for expression of M195 antigen (CD33) and other myeloid cell surface markers before, 1 hour, and 24 hours after treatment with M195 using an EPICS Profile flow cytometer (89). Goat anti-mouse Ig-fluorescein isothiocyanate conjugate was also used without primary antibody to look for M195 bound to cells in vivo. MY4 (CD14), MY9 (CD33) and 12 (HLA-DR) monoclonal antibodies were purchased from Coulter (Hialeah, Fla.).

RESULTS

Patients Important characteristics of the patients are summarized in Table 1. Because patient no. 4 experienced unusual symptoms (see below) and patient no. 5 did not receive four doses due to the onset of typhlitis and acute abdomen, an additional patient was added at the 5 mg/m$^2$ dose level to confirm safety at this level (Table 2).

Pharmacology Pharmacokinetics were based on the first trace-labeled dose of M195 as well as on ELISA analysis for mouse mAb in plasma. Since total plasma radioactivity closely approximated the trichloroacetic acid precipitable plasma radioactivity, only the former was used. Analysis of $^{131}$I-M195 in selected samples of patient plasma showed that there was no significant loss of immunoreactivity of the M195 remaining in serum up to 2 days after infusion. Thus, half-life calculations probably reflect the behavior of the biologically active M195.

Single M195 doses ranged from 1.5 mg to 19 mg (1 to 10 mg/m$^2$) and total doses ranged from 6 mg to 76 mg (Table 2). Two-phase kinetics were seen in all but two patients. Median plasma T½ alpha was 1.3 hours; median plasma T½ beta was 52 hours; median whole body half-life was 53 hours. Pharmacokinetics were not dose related. with one exception, initial volume of distribution (Vd) adjusted for patient size was slightly larger than expected blood volume (median 3.3 L/m$^2$)and steady state Vd/m$^2$ was 5.1 L (median). Marked absorption in vivo of M195 onto target cells was observed clearly in the first patient where initial Vd was three times greater than blood volume and steady state Vd was 25 L. In this patient, approximately 1 mg of M195 was injected per Kg of tumor, whereas in all of the other patients, M195 IgG doses were in excess of 10 mg M195 per Kg of estimated tumor burden (Table 2).

Plasma levels of M195 Ig were also measured during the days of treatment using samples obtained twice daily. Peak M195 levels (Table 2), which were reached after the third or fourth dose, and trough levels, which were reached just prior to the second dose, were dose-related. Serum M195 levels at the lowest dose level, however, were lower than would be predicted by simple distribution of the dose into the plasma, and suggested again that continuous removal of M195 out of the plasma and onto a saturable target was occurring. Above this first dose level, this effect was not seen, presumably due to saturation of binding sites with the first 2 to 3 mg of injected M195.

Toxicity. Patient no. 1 complained of transient mild pruritus during infusions; no urticaria was seen. There were no other symptoms during infusions even at doses 15 times higher in the nine other patients. Patient no. 4 began to complain of severe bone pain and tenderness in the sternum, pelvis, skull, long bones, beginning after her third dose of M195 (27 mg cumulative). All of these areas demonstrated uptake of $^{131}$I-M195 on scans (see below). The pain persisted for 3 days following the last infusion and required intravenous narcotics for control of pain. Patient no. 8 had left parotid extramedullary involvement with leukemia. She complained of severe parotid pain and swelling after 2 days (36 mg cumulative M195 dose). Distinct uptake of M195 into this gland was seen on scans as well. No other short or long term toxicities or effects were seen in any other patients.

Biological Effects. In two of the patients with elevated leukemic cells at the start of therapy, transient (less than 18 hours) drops in peripheral blood blast counts attributable to the M195 infusions were observed. No sustained changes in peripheral blood counts, or bone marrow blast counts or differentials were observed. There were no significant changes in platelets, hemoglobin levels, chemistries or electrolytes associated with the M195 infusions.

Fibrinogen, partial thromboplastin times (PTT) and prothrombin times (PT) were followed in all patients. In patient no. 4, with APL, normalization of fibrinogen from 99 to 144 mg per dl occurred concurrently with M195 therapy. Seven of the other nine patients with normal fibrinogen levels also showed an increase of fibrinogen levels (30% to 60% increases) while on M195 therapy.

There were no tumor responses in the patients studied. Patients no. 1 and 4 required retreatment with hydroxyurea immediately upon stopping M195 and patient no. 8 had to be restarted on hydroxyurea after two doses of M195 due to rapidly escalating blasts.

Figure 12A:
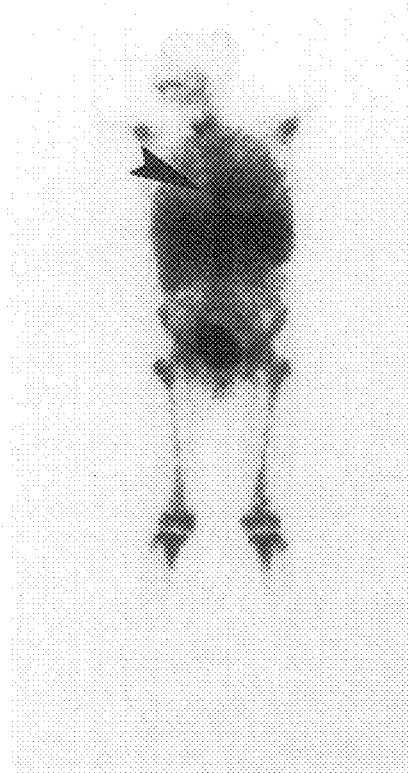
Figure 12B:
Figure 12C:
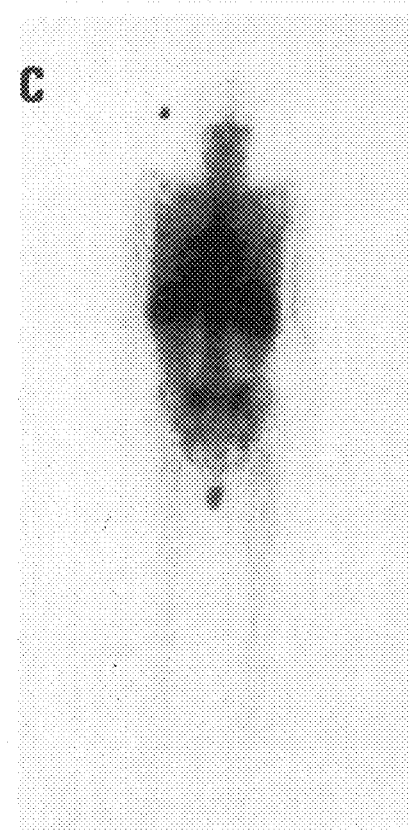
Figure 12D:
Figures 12E, 12F:
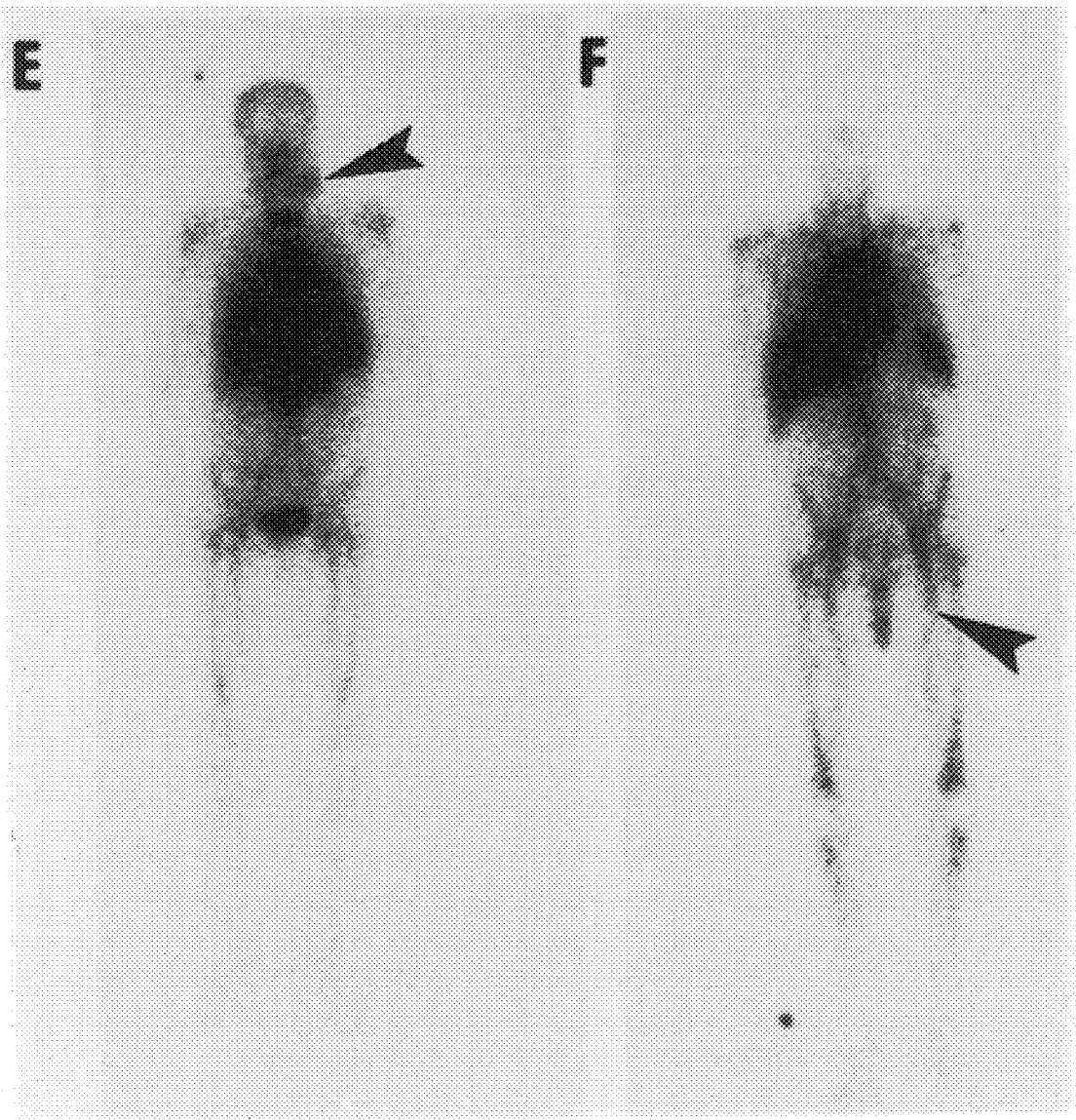

Radiolocalixation. Anterior and posterior whole body imaging demonstrated marked uptake of $^{131}$I-M195 into all areas of bone marrow in all patients (FIGS. 12A–12F, 13A–13C). Skull, sternum, ribs, vertebrae, pelvis and long bones of upper and lower extremities were clearly seen beginning within 2–4 hours after injection and lasting in most patients for up to 48 hours. Earlier time points had the clearest images due to gradual loss of isotope from the bone marrow over time. At doses of 5 and especially 10 mg/m$^2$, the blood pool (iliac veins, vena cava, and heart) was much more clearly seen showing that antibody saturation in the hematopoietic tissue had been achieved and excess antibody was circulating in the blood (FIGS. 12 E, F). In contrast, in patient no. 1 with a 1.5 mg total injected dose and elevated WBC and a hypercellular bone marrow, no blood pool was seen (FIG. 12A).

The liver and spleen were imaged in all patients. The liver uptake, about 12%, may be attributed to the large blood pool in this organ, targeting to resident leukemia cells, monocytes or macrophages as well as accumulation of labeled leukemia cells after antibody binding elsewhere. Although Fc receptor mediated binding of M195 was not seen in vitro, non-specific uptake by the reticuloendothelial system (RES) was further discounted by comparison to a standard bone marrow scan using $^{99m}$Tc sulfur colloid done in four patients. The colloid scan is taken up by the RES throughout the body and the large majority of the dose accumulates in the liver and spleen (>80%) (FIG. 13B). Thus, in order to see the bone marrow the image has to be overexposed (FIG. 13C). In contrast, the large majority of the $^{131}$I-M195 is concentrated in the bone marrow (FIGS. 12, 13A). The anatomic distribution of marrow for both the $^{131}$I-M195 and the $^{99m}$Tc were the same in the patients showing that the M195 was targeting to all known areas of bone marrow.

Two patients with extramedullary leukemic involvement also showed marked uptake into these areas as well. This included a left parotid gland (FIG. 12E) and a large mediastinal granulomatous sarcoma (FIG. 12A). Iodine-131 metabolism and excretion was seen in most patients in the thyroid and bladder. No nonspecific organ uptake was seen in any patient. These images demonstrated rapid, specific and substantial targeting of the M195 to all areas of known leukemia in every patient, not only in patients with high WBC and packed marrows, but also in hypoplastic patients and patients after bone marrow transplantation with percentages of CD33 positive blasts as low as 15–30%. Comparisons of images versus injected dose also suggested that higher doses were less effective (that is, less specific) due to increased blood pool activity following saturation of bone marrow sites.

The decrease in percentage uptake of $^{131}$I-M195 at the highest dose may be explained by the saturation of sites at earlier levels. However, the loss of total binding at 10 mg/m$^2$ level is paradoxical. This might be attributed to clinical differences in the patients such as increased peripheral blood blasts as compared to marrow or to decreased M195 expression on blasts (Eg in patient 10). In addition, modulation of the M195 antigen-antibody complex has been shown to be dose dependent in vitro (88).

Dosimetry. The percentage of the injected dose of $^{131}$I-M195 found per gram of plasma was similar at 1 hour for all three dose levels (means: 0.011%, 0.015%, 0.014%) and similar for all three levels at three days (means: 0.005%, 0.006%, 0.003%). The percentage uptake of $^{131}$I-M195 into bone marrow core biopsies per gram was highest at the 5 mg/m$^2$ dose level at both sampling times (Table 3). The marrow to plasma ratios were similar at both sampling times suggesting that the halflives of the $^{131}$I-M195 in marrow were similar to those in the plasma. Several lines of evidence suggest that the actual ratio of radiation doses of the red marrow (cellular components) to the whole blood is probably at least twice the dose ratios of marrow core biopsies to plasma shown in Table 3: 1. Since the bone marrow core biopsy contains about 50% non-hematopoietic tissue (143) with a wide range of cell numbers (144), the recorded percentage uptake in the biopsy underestimates the percentage uptake into the cellular compartment of the marrow by 50%. 2. In seven patients, radioactivity per Ficoll-Paque separated bone marrow mononuclear cells was also determined and showed that in five patients (no. 1, 3, 6, 7, 10) bone marrow core $^{131}$I-M195 doses were underestimating the actual cellular $^{131}$I-M195 doses by 33 to 300%. In patient no. 5 calculated $^{131}$I-M195 doses were equal by both methods and in patient no. 8, the aspirate showed a 50% lower dose. The data are confounded, however, both by contamination of the aspirates by peripheral blood cells and by losses of $^{131}$I-M195 during the separation and washing processes. 3. Whole blood percentage uptake was about 30% lower than plasma (due to dilution from untargeted red cells), thus raising marrow biopsy to whole blood ratios of $^{131}$I about 30% more. 4. The ability to clearly image the bone marrow at 3–4 hours after infusion at lower M195 dose levels without seeing the major blood vessels, also suggests that $^{131}$I-M195 levels must be significantly higher in the marrow than in the blood at this later time-point. It is probable that the 1 hour sampling does not reflect the maximum $^{131}$I-M195 dose to the marrow since maximum binding to peripheral blood target cells required several hours (when measured in a selected patient).

In the three patients at the lowest dose level, percentage uptake in the bone marrow core biopsy sample was approximately two thirds that found in the plasma at both time points. In the four patients at the 5 mg/m$^2$ dose level, percentage uptake in the bone marrow was initially 1.3 to 4 times higher than in plasma. These four patients generally maintained the higher ratios of marrow to plasma until the second sampling time. At the highest dose level, marrow to plasma ratios of $^{131}$I were lowest at both timepoints, averaging about 1:3. Therefore, bone marrow percentage uptake was dosedependent and was greatest at 5 mg/m$^2$. Using conservative estimates that the true ratios of radiation doses to red marrow cells as compared to blood are at least twice that of core biopsy to plasma, estimates of the radiation dose ratios of marrow to blood in patients treated at 1 mg/m$^2$ were from 1.0 to 1.5, at the 5 mg/m$^2$ level were from 2.6 to 8.6, and at the 10 mg/m$^2$ were from 0.7 to 1.7.

To determine total incorporation of $^{131}$I-M195 into the entire marrow, we assumed 3000 grams of bone marrow (fat and cells) in a standard man (143). As before, the highest percentage incorporation occurred in the four patients receiving 5 mg/m$^2$ doses (mean±SD: 85%±25). The incorporation into marrow of patients no. 5–7 are undoubtedly overestimated, most likely due to sampling error in the biopsies. Percentage uptake into the entire marrow in patients at dose levels 1 mg/m$^2$ and 10 mg/m$^2$ were considerably lower but still substantial (mean±SD=17%±3 and 23%±10). By assuming approximately 10$^9$ cells per gram of a normocellular bone marrow (37), and calculating 4×10$^9$ IgG molecules per ng of M195, we could also estimate the initial targeting of several hundred to several tens of thousands of M195 IgG per cell depending on the patient. At three days, the numbers of IgG were about 50 to 75% less.

The decrease in percentage uptake of $^{131}$I-M195 at the highest dose may be explained by the saturation of sites at earlier levels. However, the loss of the total binding at 10 mg/m$^2$ level is paradoxical. This might by attributed to clinical differences in the patients such as increased peripheral blood blasts as compared to marrow or to decreased M195 expression on blasts (e.g. in patient 10). In addition, modulation of the M195 antigen-antibody complex has been shown to be dose dependent in vitro (88).

Radiation doses delivered to the bone marrow, blood, whole body and liver were next calculated using the pharmacokinetic data and areas of interest on images. The liver was the only organ selected for dosimetric study because it was the only non-hematopoietic tissue to show uptake on scans (other than bladder and thyroid which were considered non-relevant). Rads per mCi were calculated for both $^{131}$I and $^{123}$I, an auger electron emitter, since either might be used in future therapeutic trials. For $^{131}$I, total whole body doses (penetrating plus nonpenetrating) ranged from 0.33 rad/mCi to 1.00 rad/mCi; total plasma doses, from 1.1 rad/mCi to 6.1 rad/mCi; liver doses, from 1.8 rad/mCi to 4.0 rad/mCi. These doses of radiation were not related to M195 IgG dose.

Bone marrow radiation doses have been traditionally assumed to be similar to the blood dose (145), but this is in systems where the bone marrow is not a target organ. We have already shown (discussed above and in Table 3) that the marrow cellular uptakes are probably at least twice as high as predicted by the core biopsy itself. Thus, marrow cell radiation doses can be estimated to be at a minimum equal to: (blood dose)×(the ratio of bone marrow core to blood uptakes of $^{131}$I)2×(2). This would predict red marrow cellular doses of 5 to 34 rad/mCi at the 5 mg/m$^2$ dose level; doses of 2–5 rad/mCi would be achieved in patients at the other dose levels (Table 3).

Since the M195 is internalized and radioiodine is subsequently retained within cells, microdosimetric calculations were made as well, in terms of KeV delivered within a cell nucleus per decay. For $^{131}$I, assuming one atom of iodine-131 per IgG molecule, minimum cell nucleus doses would range in our patients from 10 KeV to 960 KeV per cell and would be highest at the 5 mg/m$^2$ dose level (mean: 523; range: 130–960 KeV; 1000 KeV is 250 rad). Doses to nuclei at levels 1 mg/m$^2$ and 10 mg/m$^2$ were a lower (mean: 33; range:10–70 KeV and mean: 113; range 60–220 KeV; respectively). These estimates do not include cell surface to nucleus doses or beta and gamma doses from the M195 in the blood or neighboring cells and thus represent a minimum estimated additional dose to the nucleus (140, 141).

Human Anti-Mouse Antibody (HAMA) Responses. Serum was assayed for the presence of HAMA in 6 patients who had adequate survival and follow-up after treatment. Sera from four patients were positive. HAMA was seen in two patients as early as 14 days, but was delayed to 3 weeks in another patient.

Antigen-Antibody Modulation and Isotope Internalization. Peripheral blood leukemia cells were analyzed for the presence of CD33 antigen and other specific cell surface proteins as well as for the presence of bound M195 before and after infusion of $^{131}$I-M195. Lymphocytes, blasts or monocytes, and polymorphonuclear leukocytes were examined separately, simultaneously with single color fluorescence using three bit maps. By comparing the amount of directly labeled anti-CD33 antibody (M195-FITC or My9-FITC) able to bind to leukemia cells ex vivo after infusion of M195 to the quantity able to bind before, we could demonstrate the binding in viva of M195 on the circulating cells. This was confirmed using FITC-goat anti-mouse Ig added directly to the cells ex vivo, to demonstrate the new presence of surface bound M195 following infusion. Unrelated surface markers (HLA-Dr or My4 (CD14)) were used to identify the blasts which may have modulated (lost) both antigen and antibody from the surface.

At high doses, there was a selective saturation of CD33 sites after infusion. $^{131}$I-M195 saturation was complete at 1 hour in vivo, as shown by the lack of My9 binding and complete goat anti-mouse Ig (GAM) binding (FIG. 14). By the following day, however, both antigen and antibody were lost from the cells, as shown by loss of both My9 and GAM binding. Therefore, modulation had occurred. This has been described for M195 in in vitro models (88, 136). M195 antigen and antibody slowly returned with time. A similar phenomenon occurred in four other patients although it was less complete. In two patients neither saturation nor modulation was observed.

The fate of bound $^{131}$I-M195 following modulation was determined by sequential radioimmunoassay of the purified blasts in five patients. Cells were studied after binding of M195 ex vivo in four of the five patients (no. 1, 4, 8, 9) and after binding in vivo in three of the five patients (no. 8, 9, 10). Ex vivo, 30–50% of bound M195 internalized into leukemia cells over two to four hours and was retained within the cells for variable amounts of time. In vivo, an even larger percentage (30%, 70%, 75% in patients no. 8, 9, 10, respectively) of the bound $^{131}$I entered an acid-resistent compartment, showing that the M195 had internalized into the cell after binding. The in viva internalized $^{131}$I-M195 was slowly lost over time but a large percentage remained within the cells for up to 24 hours (FIG. 15).

DISCUSSION

There is no effective curative therapy for the acute and chronic myeloid leukemias which affect about 15,000 people yearly in the United States. Nonspecific chemotherapy is able to kill these cells but also kills normal hematopoietic progenitors, mature hematopoietic cells of all lineages, and can severely damage other tissues. Monoclonal antibodies which selectively target specific cell populations may offer an alternative therapeutic modality providing that the antigen target is not expressed on other adult tissues, ultimate hematopoietic stem cells, mature myeloid cells, or nonmyeloid lineages. Gp67 (CD33) is such an antigen (84–89). If selective elimination of all cells to which M195 binds could be achieved without damage to other cells and tissues, elimination of leukemia cells with acceptable morbidity would be possible.

We describe here a trial of a monoclonal antibody in AML showing specific bone marrow upake and imaging. The study was designed to answer two major questions: 1. Could an antibody that binds to CD33 be administered safely and would the binding by a non-cytotoxic murine antibody alone result in biological responses, toxicity, or regressions? 2. What are the pharmacokinetics, localization characteristics, and dosimetry of mAb M195 which might be used to design trials where M195 is used as a carrier of a cytotoxic isotope or other agent? The first question was answered by infusing 10 patients over 1 week with dose-escalating amounts of M195 to levels adequate to more than saturate all CD33 sites on leukemia cells in the blood and marrow. Because the first dose of M195 was also trace-labeled, we were able to answer the second question by serial blood and bone marrow sampling and whole body imaging, which allowed quantitative kinetic levels of M195 on various tissues and cells to be determined.

Bioloaical effects and patient responses Adverse reactions were absent in seven of ten patients, but included transient pruritus in one patient, severe bone marrow pain in a second patient and parotid pain in a third. We cannot clearly attribute the parotid pain to the M195 because Lugol's solution may cause parotitis (146). However, the affected left parotid also showed marked uptake of $^{131}$I-M195 on scans.

There were no therapeutic effects nor changes in serum chemistries or blood counts. Eighty percent of patients showed marked rises in fibrinogen levels, including the patient with APL and DIC, but the significance of this is unclear without clinical leukemia responses; the increases may be due to a nonspecific acute phase reactant increase. The lack of biological effects at doses shown to be saturating in vivo suggests that a non-cytotoxic mouse mAb to CD33 will not be useful unless used as a carrier of another biologically active agent. The function of the CD33 protein is unknown. If toxic or therapeutic effects are achieved with mouse mAb conjugates or biologically active humanized mAb to CD33, these effects can now be clearly attributed to the effector mechanisms of the constructs and not to the blocking of CD33 sites.

Four of six patients tested developed HAMA, showing that even in a severely immunosuppressed, heavily pretreated population, the mouse antibody was immunogenic.

Interestingly in one patient, the HAMA may have derived from a donor bone marrow. Because of the small sample size and reduced follow-up in this population, conclusions about the true incidence of HAMA after treatment with M195 cannot be made; however, unlike the reduced incidence of HAMA in patients with B cell neoplasms (147), HAMA may be a prominent response in patients with AML, despite heavy pretreatment including bone marrow transplantation or cytopenias.

Pharmacology. Pharmacologic study showed mAb M195 to be distributed largely in the blood with halflives ranging from 33 hours to 111 hours. In all but one patient, however, infused doses were in vast excess of those necessary to saturate estimated target sites. Since 2.5 mg of M195 ($10^{16}$ molecules) is equal to the estimated number of antigenic sites ($10^{16}$) on a Kg of cells, it is not surprising that no major changes in Vd or T½ were seen in response to changes in dose in these latter patients. Since the M195 dose in patient no. 1 was five times below a saturating dose, absorption out of the serum and subsequent elevated Vd can be predicted. In this patient with calculated antigen excess, absorption of the majority of the injected dose into target cells occurred immediately after infusions, resulting in a Vd of 8.3 L/m² and the clearest bone marrow images. Although the bone marrow imaged in all patients, increasing blood activity occurred with increasing doses of mAb M195. Therefore, the highest specificity of delivery was achieved at the lowest dose level, a result quite different from that observed in other systems, but consistent with the rapid and efficient saturable targeting seen. The concentration of M195 at the lowest dose level is about 1 nM, the same concentration as the calculated avidity constant in vitro (88). Thus, the behavior of the mAb in vivo in this hematologic system is similar to its activity in vitro.

Modulation of M195 antigen and antibody occurred rapidly after binding. This phenomena had been shown to occur in in vitro models of M195 with both $^{125}$I and $^{111}$In labels (136). surprisingly, the retention of $^{131}$I inside the target blasts was greater after in vivo binding and internalization as compared to similar binding ex vivo (136; and this work). Up to 70% of the cell-associated $^{131}$I was within the cells after binding in vivo. This may be attributable to the less physiologic conditions in the experiments done solely in vitro or to shorter times of incubation in vitro (1 hour at 37° in vitro versus 1½–2 hours in vivo). Although modulation resulted in internalization of isotope, it also implies that repeated doses of mouse M195 may not be useful, since HAMA may develop before the return of antigen positive cells. Use of a humanized mAb may allow repeated dosing at intervals designed to allow re-expression of target antigen.

Dosimetry. Radiation dosimetry based on pharmacology, biopsies, and image analysis showed that M195 would be capable of delivering extraordinary doses of radiation specifically to the bone marrow using $^{131}$I as a conjugate. At the intermediate dose level an estimated 5 to 34 rads would be delivered for each mCi of $^{131}$I injected. Whole body (0.3 to 1.0 rad/mCi) and normal organ doses would be minimal except for those to the liver (1.8 to 4.2 rad/mCi); tolerable liver radiation doses could be maintained by limiting injected $^{131}$I-M195 to 500 mCi, which would still enable an estimated delivery of 2500 to 17,000 rad to the marrow. This would permit complete marrow ablation to be achieved using $^{131}$I-M195 with minimal non-hematopoietic toxicity—a feasible therapeutic strategy in advance of bone marrow transplantation or autologous marrow rescue. Because it is not possible to determine uptake into total cells contained in the bone marrow, the magnitude of possible sampling errors, or the true marrow halflife without numerous aspirations and biopsies in every patient, these estimates remain crude.

For therapeutic strategies not requiring bone marrow rescue, nuclides emitting shorter-ranged cell-specific emissions would be preferable; these include $^{123}$I, an auger emitter. Radiation doses were calculated for $^{123}$I, which may be conjugated to M195 with similar techniques. Because of the shorter T½ of this isotope (14 hours) as compared to $^{131}$I (193 hours), non-specific radiation doses are ten to twenty times lower than for a comparable $^{131}$I dose. Whole body doses were about 0.05 rad/mCi, plasma doses, 0.15 rad/mCi, and liver, about 0.2 rad/mCi. Doses to the whole bone marrow would also be about 10–20 times less than those calculated for $^{131}$I and would range from 0.1 to 1.4 rad/mCi. In contrast, due to the high auger electron flux, calculated Kev per target cell nuclei are very high when using $^{123}$I, especially at the 5 mg/m² dose level where 1.5 to 10.7 MeV per cell nucleus will be delivered. As before, these are minimum estimates which do not include auger or beta flux from the cell surface or beyond. Because doses from $^{123}$I to the whole body and organs are so low, when comparing radiation doses to target and nontarget tissues, $^{123}$I tagged M195 might yield a therapeutic index more than one hundred times greater than $^{131}$I-M195. These theoretical doses will be limited by achievable specific activities of labeling, however. The attachment of about one iodine-123 atom for every 10 IgG may be more realistic, so that feasible doses may be 10 times lower, or about 1 MeV to the marrow cells and under 10 rad to body. Although $^{125}$I has been used in this manner (83), $^{123}$I has not yet been used as a cytotoxic nuclide.

Alpha particle emitting nuclides such as Bismuth-212 might also be selectively therapeutic to target cells because of their short range and high LET (4). The rapid uptakes into marrow demonstrated in this report and achievable specific activities of Bismuth labeled M195 make this a reasonable alternative approach (Scheinberg and Gansow, unpublished). The specificity of delivery also allows for the use of genetically engineered immunotoxins, or cytotoxic humanized mAb (40, 41) as therapeutic modalities. Moreover, the efficacy of delivery and internalization of mAb following binding may also permit delivery of other biologically important molecules directly into leukemia cells or normal marrow progenitors in vivo.

RESULTS

MOUSE M195 A phase 1 trial of tracelabeled M195 ($^{131}$I-M195) and escalating doses of unlabeled M195 involving 10 patients with myeloid leukemias was completed. This trial confirmed safety of the M195, showed specific, rapid, and quantitive delivery of the M195 to leukemia cells, followed by internalization of isotope into cells in blood and bone marrow, showed ability to image all sites of leukemia involvement by nuclear scan, and showed that human anti-mouse antibody is formed by most patients. Extensive pharmacology and dosimetry are described which allowed a second trial to be done with $^{131}$I-M195 for therapeutic intent.

A phase 1 trial of escalating doses of $^{131}$I-M195 showed that the observations of the phase 1 above are confirmed as well as the following: Enormous cell killed was demonstrated in 6 of 8 patients with 200,000,000,000 to 1,000,000,000,000 leukemia cells killed. This occurred in heavily pretreated patients, including after bone marrow transplant, in patients who had completely failed to respond to the best available chemotherapy, and in patients with high circulating blast counts. There has been no significant non-hematologic toxicity, despite this cytoreduction of leukemia. There have been no tumor lysis syndromes and no liver function abnormalities seen. In some patients, even normal hematopoietic cells have been spared.

NOTES TO TABLE I aAHL is acute myelogenous leukemia followed by the FAB classification if available; CMMOL is chronic myelomonocytic leukemia.

[b]Abbreviations: COPBLAM is cytoxan, vincristine, prednisone, bleomycin, adriamycin, methotrexate; IDA is idarubicin; HDAC is high dose Ara-C; MITO is mitoxantrone; HU is hydroxyurea. Ara-C is cytosine arabinoside. AZQ-CTX-TBI-BMT is AZQ, high dose cytoxan and total body irradiation followed by allogeneic bone marrow transplantation. DAT is daunomycin, Ara-C, and thioguanine. CROP is cytoxan, adriamycin, vincristine, prednisone. AMSA is amsacrine. HMBA is hexamethylenebisacetamide.

[c]WBC is white blood cells per ul$\times 10^{-3}$; Platelets is per ul$\times 10^{-3}$; Hgb is hemoglobin in g per dl; ANC is absolute granulocyte count per ul. Several of the patients were platelet or red cell transfusion dependent.

[d]For the purposes of estimating tumor burden to assist in dosimetry calculations, normocellular marrows were assumed to have 1 kg or $1\times 10^{12}$ cells and were thus assigned an arbitrary value of 1.0 kg; hypercellular: 1.2 kg; hypocellular: 0.8 kg; and very hypocellular: 0.3 kg (see also ref. 37).

[e]Promyelocytes and blasts in this patient.

[f]Monocytes and blasts in this patient.

[g]The patients were receiving multiple antibiotics.

NOTES TO TABLE 2

[a]No Fit means only one slope was determined by regression analysis.

[b]ND is Not Determined.

[c]Determined by urine clearance in patients nos. 1 and 5 due to morbidity of the patients.

[d]Determined by ELISA.

[e]total tumor burden in Kg (where 1 Kg is assumed to be $10^{12}$ cells) was estimated as the blood involvement: [WBC per ul times % blasts times 0.003 times the body surface area]; plus the bone marrow involvement: [cellularity factor times % blasts times 0.01]. Cellularity was defined arbitrarily as on Table 1 using (37) as a guide. The "total" burden is probably an underestimate since spleen, liver and extramedullary involvement are not included. Moreover, there is no way to determine the accuracy of our assumed burden in the marrow.

[f]Mg of M195 injected per dose for each estimated Kg of leukemia cell burden.

[g]NA: Not applicable since only two doses were given.

TADLE 1

CLINICAL CHARACTERISTICS OF PATIENTS UNDER STUDY

| PATIENT NO. | AGE/ SEX | DIAGNOSIS[a] | PRIOR THERAPY[b] | INITIAL CBC[a] | | | | | INITIAL BONE MARROW | | PERFORMANCE STATUS | MULTIPLE ANTIBIOTICS[a] |
|---|---|---|---|---|---|---|---|---|---|---|---|---|
| | | | | WBS | BLASTS | PLATELETS | HqB | ANC | CELLULARITY[d] | % BLASTS | | |
| 1 | 24/M | ANL - N2 Refractory | COP-BLAM;IDA-HDAC; MITO-VP16; HU. | 39.0 | >90% | 21 | 10.7 | 1800 | Hypercellular | 100 | 50 | Yes |
| 2 | 20/F | AML - M2 Relapsed | IDA-Ara-C;IDA-HDAC;AZQ-CTX-TBI-BMT. | 1.2 | <10% | 45 | 9.2 | 200 | Very Hypocellular | 54 | 70 | N0 |
| 3 | 24/M | AML - M2 Refractory | DAT;IDA-HDAC;HU. | 2.4 | <10% | 135 | 8.3 | 1500 | Hypocellular | 13 | 70 | N0 |
| 4 | 43/F | AML Refractory | CHOP;MITO-VP16; Ara-C;MITO;DA;HU. | 4.1 | 50% | 17 | 9.4 | 500 | Hypercellular | 78 | 60 | Yes |
| 5 | 34/M | AML - M3 Refractory | CTX-HDAC-VCR;DAT; HDAC;Ara-C-VP16; Daunorubicin-VP16. | 0.5 | <10% | 29 | 10.0 | 300 | Normal | 51* | 60 | No |
| 6 | 46/F | AML Refractory | DA;HDAC;IDA-HDAC; G-CSF;Ara-C. | 0.7 | <10% | 74 | 8.2 | 0 | Normal | 89 | 60 | Yes |
| 7 | 60/M | AML - M5B Relapsed | DA;IDA. | 1.8 | <10% | 32 | 9.2 | 100 | Hypocellular | 74[f] | 60 | Yes |
| 8 | 47/F | AML Refractory | DA;AMSA-HDAC; MITO-VP16; HU. | 91.0 | >90% | 134 | 9.7 | 600 | Hypercellular | 87 | 60 | Yes |
| 9 | 74/M | CMMOL Untreated | NONE | 26.0 | 42%[f] | 50 | 8.2 | 11,300 | Hypercellular | 27[f] | 80 | N0 |
| 10 | 29/F | AML Relapsed | IDA-Ara-C;AMSA-HDAC;VP16-MITO; AZQ-CTX-TBI-BMT HMBA. | 5.4 | >90% | 27 | 9.4 | 65 | Hypercellular | 79 | 70 | Yes |

TABLE 2

PHARMACOLOGY OF $^{131}$I M195

| PT. # | DOSE LEVEL mg/m$^2$ | TOTAL DOSES GIVEN | TOTAL (mg) | PLASMA HALF-LIFE T½α | PLASMA HALF-LIFE T½β | WHOLE BODY HALF-LIFE T½ (hr) | INITIAL Vd/m$^2$ (L) | PEAK PLASMA LEVEL (ng/ml)$^d$ | ESTIMATED TUMOR BURDEN (KG)* BLOOD | ESTIMATED TUMOR BURDEN (KG)* TOTAL | Mg. Inj. M195 PER Kq TUMOR$^f$ |
|---|---|---|---|---|---|---|---|---|---|---|---|
| 1 | 1 | 4 | 6 | No Fit$^a$ | 39 | 28* | 8.3 | ND$^b$ | 0.166 | 1.4 | 1 |
| 2 | 1 | 4 | 6 | 1.7 | 39 | 54 | 3.3 | 320 | 0.001 | 0.1 | 10 |
| 3 | 1 | 4 | 8 | No Fit | 35 | 50 | 4.5 | 60 | 0.002 | 0.1 | 20 |
| 4 | 5 | 4 | 36 | 0.6 | 35 | 26 | 4.1 | 3000 | 0.011 | 0.9 | 10 |
| 5 | 5 | 3 | 29 | 1.7 | 58 | 111* | 2.2 | 8000 | 0.001 | 0.5 | 20 |
| 6 | 5 | 4 | 38 | 2.3 | 77 | 68 | 3.1 | 4000 | 0.001 | 0 9 | 10 |
| 7 | 5 | 4 | 38 | 0.5 | 53 | 84 | 3.3 | 1200 | 0.002 | 0.6 | 16 |
| 8 | 10 | 2 | 36 | 4.6 | 69 | 61 | 2.9 | NA$^a$ | 0.490 | 1.5 | 12 |
| 9 | 10 | 4 | 76 | 1.0 | 50 | 36 | 3.5 | 5000 | 0.060 | 0.4 | 48 |
| 10 | 10 | 4 | 72 | 0.8 | 43 | 52 | 4.6 | 5500 | 0.029 | 1.0 | 17 |

TABLE 3

$^{131}$I-M195 UPTAKE AND DOSIMETRY

| PATIENT NUMBER | DOSE PER M$^2$ | % INJECTED DOSE PER GRAM OF BONE MARROW$^b$ 1H | % INJECTED DOSE PER GRAM OF BONE MARROW$^b$ 3D$^a$ | NG IgG DELIVERED PER GRAM OF BONE MARROW$^b$ 1H | NG IgG DELIVERED PER GRAM OF BONE MARROW$^b$ 3D$^a$ | WHOLE BODY DOSES (Rad/mCi) $^{131}$I | PLASMA DOSES (Rad/mCi) $^{131}$I | LIVER DOSES (Rad/mCi) $^{131}$I | RED MARROW DOSES (Rad/mCi) $^{131}$I |
|---|---|---|---|---|---|---|---|---|---|
| 1 | 1 | .005 | .002 | 75 | 29 | 0.35 | 1.1 | ND | 1.7 |
| 2 | 1 | .007 | .005 | 105 | 76 | 0.60 | 5.1 | 4.0 | 5.1 |
| 3 | 1 | .006 | .002 | 120 | 40 | 0.57 | 2.2 | 3.1 | 2.6 |
| 4 | 5 | .013 | .002 | 1170 | 171 | 0.33 | 1.9 | 1.8 | 4.9 |
| 5 | 5 | .030 | .010 | 2100 | 900 | 1.00 | 6.1 | 3.4 | 16.7 |
| 6 | 5 | .050 | .003 | 4750 | 290 | 0.72 | 4.2 | 4.2 | 26. |
| 7 | 5 | .060 | .030 | 5700 | 2850 | 0.83 | 3.9 | 3.1 | 33.5 |
| 8 | 10 | .006 | .001 | 1080 | 162 | 0.68 | 3.6 | 3.4 | 2.4 |
| 9 | 10 | .011 | .002 | 1980 | 375 | 0.43 | 2.9 | 1.8 | 4.9 |
| 10 | 10 | .004 | .001 | 540 | 125 | 0.58 | 2.6 | 1.8 | 1.8 |

Patienta #1 and #8 had biopsies at 4 days; Patients #4 and #5 had biopsies at 2 days.

EXPERIMENT 5

AUTOLOGOUS BONE MARROW TRANSPLANTATION IN ACUTE MYELOGENOUS LEUKEMIA; IN VITRO TREATMENT WITH MYELOID-SPECIFIC MONOCLONAL ANTIBODIES AND DRUGS IN COMBINATION

MATERIALS AND METHODS

Human Cell Line. HL-60 is a human acute promyelocytic leukemia cell line growing with a doubling time of 24 hours and a plating efficiency of 7–12% (148). The cell line was maintained in exponential growth in RPMI-1640 supplemented with 10% fetal calf serum (FCS-Hyclone, Logan, U.S.A.) 1% L-Glutamine at 37° C. in a humidified atmosphere of 5% $CO_2$ air. Cell viability was always higher than 95% and cells were free of mycoplasma contamination.

Bone Marrow Cells. Bone marrow was aspirated from the posterior iliac crest of healthy volunteers after obtaining written informed consent and BM mononuclear cells were collected after Ficoll-Hypaque gradient (1.077 g/cm$_3$).

Leukemic Samples. Cells were obtained from peripheral blood of eight AML patients (Table 1). The diagnosis of AML was established by morphological criteria, cytochemical staining and by surface markers analysis using a panel of MaABS. Leukemic specimens were subclassified according to the FAB classification system (149). If the platelet count was sufficiently high, the blood was first depleted of platelets by centrifugations over Percoll (1.050 g/CM$_3$) (Pharmacia Fine Chemicals Co, Piscataway, N.J.), and light density cells were subsequently obtained by centrifugation over Percoll

TABLE 1

AML CASES

| # | AGE/SEX | Source of Cells | FAB[1] Classification | % P.E.[2] | % Blasts[3] | % Promyelo-[3] cytes |
|---|---|---|---|---|---|---|
| 1 | 69/F | PB* | M1 | 0.016 | 79 | 7 |
| 2 | 35/F | PB | M2 | 2.7 | 89 | 4 |
| 3 | 60/M | PB | M4 | 0.93 | 95 | 4 |
| 4 | 69/M | PB | M4 | 1.1 | 98 | 0 |
| 5 | 54/M | PB | M5B | 0.35 | 86 | 0 |
| 6 | 39/M | PB | M5B | 1.6 | 69 | 19 |
| 7 | 44/F | PB | M2 | 0.2 | 92 | 2 |

TABLE 1-continued

AML CASES

| # | AGE/ SEX | Source of Cells | FAB[1] Classification | % P.E.[2] | % Blasts[3] | % Promyelo-[3] cytes |
|---|---|---|---|---|---|---|
| 8 | 36/M | PB | M4 | 0.93 | 87 | 5 |

[1]French-American-British
[2]P.E. Plating Efficiency
[3]The percentages of blasts and promyelocytes were obtained by counting 200 cells from May-Grunwald-Giemsa-stained cytocentrifuge smears after thawing.
*PB, Peripheral Blood (1.075 g/CM$_3$). The leukemic cells were suspended in fetal calf serum and cryopreserved using a mixture containing 5% dimethylsulfoxide (DMSO) and 6% hydroxyethyl starch (HES) as described (150). Cells were froze at −120° C. in a Revco Freezer (Revco Scientific., Asheville, N.C.). After thawing the cells were suspended in Iscove's modified Dulbecco's medium (IMDM) supplemented with 10% fetal calf serum (FCS) (Hyclone laboratories, Inc., Logan, UT), 60 u/ml of Deoxyribonuclease 1 (DNAse) (Cooper Biomedical, Malvern Pa.) and incubated for 30 min on ice. Viable cells were recovered by Ficoll-Hypaque gradient. All samples contained more than 86% of blasts and promyelocytes (Table 1). Content of residual T cells was assessed by immunofluorescent staining with panel of MoAbs (anti $T_3$, $T_1$ and $T_{11}$) and was for all the patients less than 2%.

Chemotherapeutic Compounds. VP-16 (Bristol Labs, Syracuse, N.Y.) and 4 HC (kindly provided by Dr. O. M. Colvin, John Hopkins University, Baltimore, Md.) were diluted immediately before use with RPMI-1640 and PBS without calcium and magnesium, respectively.

MoAbs. M195 is a mouse IgG2a monoclonal antibody which reacts with the CD33 protein p67 (151). F23 is a mouse IgG2a monoclonal antibody (kindly provided by Dr. L. J. Old) whose target antigen (CD13) is expressed on early and mature myeloid cells. HPCA-1 (My10, Becton-Dickinson, Mountain View, Calif.) is a mouse IgG1 monoclonal antibody directly toward CD34 antigen expressed on putative human hemopoietic progenitors (152).

Incubation Procedure and Culture Techniques. Tumor cells and normal BM cells were adjusted to a concentration of $2 \times 10^6$/ml and $20 \times 10^6$/ml, respectively. VP-16 was added at the concentration of 5 μg/ml; 4HC:80 μM or 100 μM; M195 and F23: 40 μg/ml while the optimal complement (Baby Rabbit Complement, Pel Freez, Brown Deer, Wis.) concentration was found to be 1.6 (V/V). After completion of 1 hr incubation at 37° C., the cells were put on ice for five minutes and washed twice with RPMI supplemented with FCS. To simulate "ex vivo" BM purging conditions, the HL-60 cells were also incubated together with irradiated (3,000 cGy) BM cells (1:10 ratio). Tumor cells, after incubation alone or in mixture with irradiated normal BM cells were plated in 35 mm plastic Petri dishes (Miles Lab, Naperville, Ill.) in quadruplicate. The culture medium consisted of 1.1% methlcellulose (Methocel A4M, Dow Chem Co, Midland, Mich.) in IMDM containing 20% FCS, 1% antibiotics and 1% L-glutamine. The number of cells plated in 1 ml of medium was 1,000 untreated and $10^5$ treated. Cells were incubated at 37° C. in humidified atmosphere of 5% of $CO_2$ in air and scored for colonies (>50 cells) after 7 days of incubation using an inverted microscope.

After treatment, normal bone marrow cells were assayed for colonies derived from CFU-GM, BFU-E and CFU-GEM as already described (150). Briefly, culture medium consisted of 1 ml of IMDM (Gibco), supplemented with 24%, 0.8% Bovine Serum albumin (BSA—Sigma Chemical Co, St. Louis, Mo.) $10^{-4}$M of 2-Mercaptoethanol (Sigma), 1 U of partially purified human urinary erythropoietin (Toyobo Inc., NY, N.Y.), 10% of a selected lot of MoCM prepared from the human MO T lymphoblastic cell line (153) (kindly provided by Dr. David Golde, UCLA—Los Angeles, Calif.) and bovine hemin 0.2 mM (Sigma). Mehtylcellulose was added at a final concentration of 1.32%. Quadruplicate cultures were incubated as described above and the colonies were scored after 14 days of incubation. Clonogenic assay for CFU-L (149) was the same as used for normal BM progenitors without the addition of bovine serum and erythropoietin. A total $10^5$ irradiated autologous cells (3,000 cGy with a $^{137}$CS source) were added per ml of culture. The number of cells plated was adjusted in order to have about 100 colonies per ml of culture in the control samples; the treated samples were cloned at higher cell concentration. Colonies (>20 cells) were scored after 10 days of incubation.

Enrichment of CD34$^+$, CD33$^-$ cells and DELTA value. Purified progenitor cells were obtained by immunopanning technique (16 after 30 min incubation with HPCA-1) (MY10, 10 μg/ml, Becton-Dickinson) as reported elsewhere (154). The percentage of CD34$^+$ blasts, evaluated by morphological analysis and immunofluorescence was always higher than 90%. $5 \times 10^4$ CD34$^+$, CD33$^-$ cells were plated in semisolid medium for CFU-GM with r-GM-CSF (1000 U/ml, Amgen, Thousand Oaks, Calif.), IL3 (50 ng/ml, Genetics Institute Cambridge, Mass.) or MoCM (10%, V/V) as colony stimulating factor. Colonies were counted after 14 days of incubation with an inverted microscope and recorded as the Day 0 (D0) CFU-GM frequency. Simultaneously, $1 \times 10^5$ cells were suspended in 1 ml of IMDU supplemented with 20% FCS containing IL3 (50 ng/ml) or IL3+IL1 (100 μ/ml, Syntex, Palo Alto, Calif.) or MoCM (10% v/v). On day 7, cells were counted and $1 \times 10^4$ cells from each suspension were plated for CFU-GM in triplicate as described above. Fourteen day colonies were recorded as D7 CFU-GM frequency, since seven days elapsed from the beginning of the liquid culture. The Delta value is determined by dividing the D7 CFU-GFM frequency by the DO CFU-Gm frequency and it is an indicator of the number of progenitors of earlier stage that the 14 day CFU-GM. When DO CFU-GM value was 0 the $D_7$ CFU-GM frequency was divided by 0.33 since the clonogenic assay was set up in triplicate and one colony was the lower limits of detection.

DATA ANALYSIS. All experiments were performed three or more times and the mean+standard deviation (SD) values of each experiment were calculated. Colony counts after drug treatment were expressed as a percent of the untreated control cells.

RESULTS

Effect of Chemo and/or Immunotherapy on Tumor Cells. Clinical characteristics of the AML patients are reported in Table 1. The median age was 49 years (range 35–69), the percent of leukemic blast ranged from 69 to 98% and residual T cells were always less than 2%. The results of HL-60 and CFU-L clonogenic assay inhibition are shown in FIGS. 16, 17. A greater than four logs of HL-60 tumor cell elimination was observed after immunochemotheapy treatment (i.e. M195 plus 4HC either used at 1000 μM or 80 μM+VP-16 and combination of M195 and F23 plus HC+VP-16) while the single procedure provided for a mean of 95+0.9% SD of colony-forming inhibition (complement-mediated lysis by M195 and F23 used together); 99.5+0.8%

SD-4HC (100 μM) used alone; 99./95+0.2% SD 4HC AND VP-16 mixture (FIG. 16).

Eight AML patients were treated according to the four protocols. No CFU-L (i.e more than 3 logs of tumor cells elimination) were found after the combined treatment with MoAb M195 plus 4HC (100 μM) and VP-16 whereas the mean colony-forming inhibition was 92.3+2.5% SD, 95.5 1.4% SD and 99+0.8% SD following antibody treatment and complement lysis, 4HC and 4HC+VP-16 treatment respectively (FIG. 17).

Complement-dependent lysis by single MoAb (I.e. M195 or F23) resulted in less than 90% of tumor cell elimination when treated on both HL-60 cells and leukemic cells from AML patients (data not reported).

Cytotoxic activity of four different purging protocols on normal BM progenitors. The mean recovery of committed normal BM precursors after treatment with MoAbs with and without 4HC+VP-16 is shown in Table 2. The low number of CFU-GEM observed in our experiments did not allow nay statistical analysis therefore only the results of CFU-GM and BFU-E recovery are reported. The single treatments showed as mean recover of 12% CFU-GM and 22.9% of BFU-E (immunotherapy) and 4.4% CFU-GM and 5.6% BFU-E (chemotherapy). The colony-forming efficiency of hemopoietic cells was completely abolished by the combined protocol in most of the experiments. When 4HC was tested a the concentration of 80 μM and combined with VP-16 and MoAbs, the recovery of CFU-GM and BFU-E was 2.7%+3 SD and 1% 2.5 SD, respectively (data not shown in table). Additional experiments were then designed to assess the recovery of progenitor cells from enriched population of CD34$^+$, CD34$^-$ cells after immunopharmacological treatment. Our assay consisted of the stimulation of the pre-CFU-GM (CD34$^+$, CD33$^-$) compartment by r-CSFs or MoCM in liquid culture followed by a clonogenic assay to evaluate the recovery of CFU-GM derived from the enriched blast population. We also compared different culture conditions to investigate the optimal combination of CSFs for stimulating early hematopoietic progenitors. In this set of experiments, the addition of the MoAb F23 to the combined treatment did not give different results than the MoAb M195 used alone with drugs, therefore only the data of M195 plus 4HC+VP$_{13}$16 protocol are reported in Table 3.

In the first three experiments IL3 alone (#1,2) or combined with IL1 (#1,2,3) and MoCM were chosen as stimulating factors in the suspension culture whine TGM-CSF and IL3 were used for inducing CFU-GM growth in the semi-solid assay. These three experiments did not show any CFU-GM recovery after the immunopharmacological treatment before enrichment of CD34$^+$ cells by

TABLE 2

Recovery of Hematopoietic Precursors after Treatment with MoAbs with and without 4HC + VP-16

| TREATMENT | COLONY FORMING INHIBITION[1] | |
|---|---|---|
| | CFU-GM | BFU-E |
| CTR + C'[2] | 11.8 ± 4.6 | 9.6 ± 3 |
| CTR + MoAbs | 10.4 ± 7.1 | 12.3 ± 2.4 |
| M195 + C' | 62.7 ± 7.2 | 46.8 ± 5 |
| F23 + C' | 48.3 ± 10.2 | 43.7 ± 6.8 |
| M195 + F23 + C' | 88 ± 7.4 | 67.1 ± 9.6 |
| 4HC | 84 ± 10 | 80.3 ± 12.5 |
| 4HC + VP-16 | 96.4 ± 3.5 | 97.2 ± 2.3 |

TABLE 2-continued

Recovery of Hematopoietic Precursors after Treatment with MoAbs with and without 4HC + VP-16

| TREATMENT | COLONY FORMING INHIBITION[1] | |
|---|---|---|
| | CFU-GM | BFU-E |
| M195 + C' + 4HC + VP-16 | 99.6 ± 1.4 | 100 |
| F23 + C' + 4HC + VP-16 | 99.4 ± 2.8 | 99.8 ± 1.6 |
| M195 + F23 + C' + 4HC + VP-16 | 99.5 ± 3.2 | 100 |

[1]Aggregates (more than 50 cells) were scored at day 14. These numbers are expressed as mean ± SD of percentages of colony-forming inhibition in comparison with control cultures. Mean numbers ± SD of CFU-GM and BFU-E, colonies per 10$^5$ cells plated were 119 ± 22, 206 ± 51, respectively.
[2]CTR represents control medium

TABLE 3

Pre-CFU-GM Assay in Vitro
Ficoll/Immunochemotherapy/CD34$^+$, CD33$^-$ Population

| | Stimulus in Conditioned Suspension Culture | Medium in semi solid assay | CFU-GM* | CFU-CM** from CD34$^+$, CD33$^-$ cells | | Delta Value |
|---|---|---|---|---|---|---|
| | | | | D0 | D7 | |
| Exp 1 | IL3 | GM | 0 | 3 | 168 | 56 |
| | | IL3 | 0 | 7 | 51 | 7.3 |
| | IL1 + IL3 | GM | 0 | 3 | 615.6 | 205.3 |
| | | IL3 | 0 | 7 | 92 | 13.1 |
| | MO-CM | GM | 0 | 3 | 1084 | 361.3 |
| | | IL3 | 0 | 7 | 367.2 | 52.4 |
| Exp 2 | IL3 | GM | 0 | 0 | 4 | >12 |
| | | IL3 | 0 | 0 | 0 | 0 |
| | IL1 + IL3 | GM | 0 | 0 | 8 | >24 |
| | | IL3 | 0 | 0 | 0 | 0 |
| | MO-CM | GM | 0 | 0 | 8 | >24 |
| | | IL3 | 0 | 0 | 8 | >24 |
| Exp 3 | IL1 + IL3 | GM | 0 | 4 | 36 | 8 |
| | | IL3 | 0 | 4 | 6 | 1.5 |
| | MO-CM | GM | 0 | 4 | 72 | 18 |
| | | IL3 | 0 | 4 | 102 | 25.5 |
| Exp 4 | IL1 + IL3 | GM | 1 | 0 | 3 | >9 |
| | | IL3 | 1.5 | 0 | 5 | >15 |
| | | MO-CM | 2.5 | 2.5 | 6 | 2.4 |
| | MO-CM | GM | 1 | G | 10 | >30 |
| | | IL3 | 1.5 | 0 | 15 | >45 |
| | | MO-CM | 2.5 | 2.5 | 18 | 7.2 | immunopanning. When CD34$^+$, CD33$^-$ cells were assayed we observed few CFU-GM in 2 experiments (#1,3) (DO value) and no granulocyte-macrophage progenitors were obtained in Exp #2. The number of CFU-GM colonies scored after one week of liquid culture (D7 value) was remarkably higher than the DO value specifically following stimulation in suspension culture with MOMC either using GM-CSF or IL3 in semisolid assay (Delta value of 361.3,.24 and 25.5 in Exp #1,2 and 3, respectively). Given the poor delta value obtained after incubation of enriched blast cells with IL3 alone, we decided to use only IL1+IL3 and MoCM and CSFs in liquid culture for the next experiments. In addition MoCM was also used as colony stimulating factor in short term assay since other studies performed at the same time in our lab, showed MoCM as the most effective CSA for a highly enriched blast cell population (155). Experiment #4 and 5 reported the highest delta value (which indicates the proliferating capacity of CFU-GM derived from CD34$^+$, CD33$^-$ cell population) when IL3 or GM-CSF were used in semisolid assay after one week of stimulation with MoCM (>45 and >30, respectively, Exp #4).

Finally, Experiment #6 compared the effect of two different immunochemotherapy protocols (4HC used at 100 μm -A- vs 80 µM -B- on early CD34+,CD33− stem cells. The pluripotent cells compartment seemed to be less affected by using the lower dose of 4HC (delta value of 180 when MoCm was used after IL1 and IL3 stimulation and >144 when GM-CSF followed either MoCM or cystimues combination stimulation) while the "contamination" of committed myeloid progenitors was similar after immunopanning in both cases. Interestingly, in four experiments (2,5, 6a and b) BM progenitors lost their responsiveness to IL3 after exposure to the same growth factor, used alone or combined, in liquid culture.

DISCUSSION

The therapeutic benefit of various techniques for purging BM in animal system is well established (156) and preliminary studies using 4HC or 4HC+VP-16 purged BM for patients with AML reported encouraging results (157,158). Although there are no data available from randomized trials to substantiate the role of BM purging for AML patients, the multicenter registration data from the European Bone Marrow Transplantation Group in 1989 showed superior results of mafosfamide purged marrow versus unpurged marrow in AML patients transplanted in CR 1 after myeloblative conditioning regimen (159).

Use of MoAbs for selective removal of tumor cells from BM is another approach and several groups have reported the production of MoAbs reactive with antigens expressed on myeloid cells that are also capable of recognizing leukemic cells from patients with AML (160–163).

Some of those MoAbs have been also used in purging protocol in the treatment of AML and trials are currently in progress involving MoAbs and complement treated marrow for leukemic patients (164–166).

However, both of these approaches (i.e chemotherapy and immunotherapy) did not show, when used alone, convincing evidence of selective killing of clonogenic leukemic cells compared to normal BM progenitors. Purging protocols using Cyclosphsphamide (CY) active derivatives (i.e. 4HC and Mafosfamide) or other alkylating agents alone or combined with different chemotherapeutics showed a differential activity between myeloid cell lines and normal BM precursors (167–169) but the same results were not confirmed when CFU-L from leukemic patients were tested (170,171) suggesting that the data obtained on continuously growing cell lines may not be predictive in view of clinical studies. Similarly, studies of the expression of cell surface antigens on AML cells demonstrated that phenotypic features are acquired in an analogous manner to their normal counterparts (32,33). Therefore, the lack of a specific MoAb which reacts on the leukemic cells is the major obstacle for this procedure. In addition, the heterogeneity in antigen expression on CFU-L could allow some leukemic cells to escape lysis (174).

In order to improve current purging methods, we attempted to remove occult leukemic cells from autologous marrow by combining two different purging methods. In particular, a multiagent chemotherapeutic protocol (4HC+VP-16) was compared and combined with complement-mediated lysis by two MoAbs broadly reactive with myeloid cells (anti-CD33 and anti CD-13).

A similar approach (i.e. immunochemotherapy) has been already proposed for purging of T-ALL and Burkitt's lymphoma cells providing a significant increase in tumor cell killing when compared with the single treatment although the results of normal BM recovery have not been reported in the first study (175,176).

The 4HC+VP-16 (100 µM and 5 µg/ml, respectivly) purging protocol has proven to have a synergistic activity on HL-60 cells and antagonistic on normal BM precursors (167) and it is being used as purging treatment for AML and non-Hodgkin lymphoma patients at Memorial Hospital (177,178). M195 MoAb recognized CD33 antigen and it was found expressed on most of the myeloblastic leukemia studied. M195 and rabbit complement were able to eliminate almost all of the committed BM progenitors in a clonogenic assay (i.e. 14 day CFU-GM and BFU-E) while no binding of $^{125}$I M195 was found on early blast cells collected by negative selection (160). These observations could suggest a therapeutic advantage for a protocol involving the use of M195 (alone or combined with an anti CD13 MoAb, namely F23) which is positive on the majority of AML cells but not on the earliest normal colony forming cells. A similar MOAb, MY9, also reactive with CD33 antigen has been used to purge AML patients marrow from residual leukemic cells (166).

In our experimental system HL-60 leukemic cell line clonogenic efficiency was reduced more than 4 logs, in presence of marrow cell excess, after 1 hr incubation with M195 plus 4HC+VP-16 while the treatment with chemotherapy or immunotherapy alone was less effective on clonogenic tumor cells. The same combined protocol produce, at sensitivity level of 3 logs, a compete eradication of CFU-L form 8 patients with AML. The addition of F23 MoAb did not further enhance the elimination of both HL-60 and CFU-L cells while a lower concentration of 4HC (i.e. 80 µM) showed the same results on HL 6-0 of the optimal 4HC concentration (100 µM) found in a pervious study (167).

After incubation of normal marrow with the immunochemotherapy protocol CFU-GM and BFU-E were undetectable in most of the experiments by direct assay in semisolid medium. However, since infusion of chemopurified marrow containing no detectable CFU-GM produced hematologic recovery in transplanted patients (179) this assay does not adequately predict the hemopoietic reconstitution capacity. Therefore, a more sensitive assay of early stem cell viability and capability to give raise to more mature progenitors is needed. Recent experimental evidences suggest that early hemopoietic progenitors with self renewal property expressed CD 34 antigen and that they are distinguishable from more differentiated myeloid cells (152, 180,181).

Furthermore, CD34+ cell fraction can be divided into distinct precursors populations according to the coexpressions of HLA-DR and CD33 antigens (181). Andrews et al. have recently demonstrated that only CD34+,CD33− cell population was able to sustain CFU-C production for five weeks in long term bone marrow culture (LTMC) system while cells that expressed both the antigens generated few CFU-C (182). The importance of CD34+ cells is also underlined by studies showing that these cells, isolated by avidin-biotin immunoadsorption technique, can restore lymphohematopoiesis in lethally irradiated baboons and humans (183, 184).

More recently, Siena et al. demonstrated that many CD34+ cells are induced to circulate in the peripheral blood of cancer patients after high dose chemotherapy and iv administration of r-Hu-GM-CSF and that the enrichment of CD34+ cell fraction is a crucial point to ensure recovery of normal hematopoiesis after myeloablative chemotherapy (185). We therefore tried to assess the ability of the immunochemotherapeutic treatment to spare the putative hemopoietic precursors (CD34+,CD33−) collected after positive selection by panning with monoclonal anti-MY10 antibody. A short-term suspension culture system, which was shown specific to self-renewal of pluripotent myeloid precursors in murine (186,187) and human model (154) was then set up and the increased in number of clonogenic efficiency of blast cells was assessed following stimulation with IL3, IL1+IL3 and MoCM. Our results demonstrated the recovery of the earlier hematopoietic progenitors than day 14 CFR-GM after immunochemotherapy. In particular, cultures containing both IL1 and IL3 or MoCM, in the absence of any preformed feeder layer, showed a marked increase in pluripotent precursors whereas IL3 used alone was less effective.

Finally, an experiment was addressed to compare the effect of two different combined protocols (4HC used at 80 $\mu$M vs 100 $\mu$M, which both gave the same results in terms of HL-60 clonogenic efficiency inhibition) on pluripotent stem cells. The lower dose of 4HC allowed a better recovery of the hematopoietic progenitor compartment and the Delta value obtained was comparable to the values observed in a large series of experiments on normal BM samples where different techniques were employed to ensure the optimal recovery and stimulation of early blast cells (154). Further experiments are currently in progress to investigate the recovery of leukemic cells after immunochemotherapy and panning with anti CD34 MoAb. In addition, the comparison between the Long Term Bone Marrow Culture System and our short-term liquid culture is underway in order to accurately quantitate pre CFU-GM precursors.

In summary, our results showed that the combination of single cycle complement-mediated lysis by MoAbs and a pharmacologic protocols can produce additive tumor cell killing on leukemic cells while, under the same experimental conditions, early hematopoietic precursor are substantially spared. Conversely, in our experiments the depletion of the committed hematopoietic progenitors was nearly complete suggesting, according to Rowley et al. (188), the efficacy of our immunopharmacological purging method in view of its clinical application. The responsiveness of early BM progenitors to IL1 and IL3 in combination also suggest that preincubation of autologous marrow with these cytokines may enhance the delayed hematopoietic reconstitution following the reinfusion of purged marrow. recent data form our lab support the use of IL1 and IL3 combination compartment without affecting the stem cell poll in the long-term BM culture stem (44). Thus, the use of 4HC+VP-16 and MoAbs would seem a reasonable approach to purge minimal residual leukemia from autologous graft.

LEGEND TO THE FIGURES

FIG. 16: Cytotoxic activity of four protocols on HL-60 cell line. MoAb+C treatment represents one cycle of 40 $\mu$g/ml of M195 and F23 with complement at 1/6 (v/v) dilution. 4HC concentration is 100 $\mu$M when used alone. 80 $\mu$M or 100 $\mu$M of 4HC gave the same result when the drug was combined to VP-16 with and without MoAbs.

FIG. 17: cytotoxic activity of four protocols on CFU-L. For details see Legend to FIG. 16.

EXPERIMENT 6

PREPARATION OF PATIENT FOR REINFUSION

Patients receiving autologous bone marrow transplantation for the treatment of acute myelogenous leukemia still largely fail due to relapse. This may be due to inadequate preparation of the host or due to inadequate purging. We propose to attempt to improve both aspects of this regimen using cytotxic monoclonal antibodies specific for acute myelogenous leukemia cells and early myeloid progenitors. In this trial, we will first assess the safety and efficacy of $^{131}$I-M195 to improve on patient conditioning.

Phase I toxicity and pharmacology studies with $^{131}$I-M195 done here suggest that in patients with low tumor burden 3–5 rads per mCi will be delivered to the marrow with $^{131}$I-M195. Thus, in the proposed trial here, we expect to deliver specifically to the marrow up to an additional 200, 400 and 600 rads at the three escalating dose levels of $^{131}$I-M195. Doses to other organs should not be significant.

M195 targets to bone marrow and carries a long range isotope for the preparative regimen such as $^{131}$I or $^{90}$Y instead of the short range isotope such as Bismuth or auger electron generators that are used for killing leukemias as described in Experiment 3 (above) to kill not only the cell on which it is attached but also nearby normal and neoplastic cells. This allows reinfusion of the new marrow. At the same time it kills residual neoplastic cells that may escape the chemotherapy or radiotherapy given as part of the conventional regimen.

This preparative regimen is useful for all allogeneic transplants, even those for non-hematopoietic cancer. It is useful in autologous transplants as well.

Study Design and Objectives. This is an escalating dose, phase I study of a radiolabeled monoclonal antibody specific for myeloid leukemia cells in patients with refractory or relapsed myeloid leukemias. Safety, toxicity, pharmacology, dosimetry and biological effects will be studied in a minimum of 9 patients.

Objectives. To determine the toxicity of radiolabeled monoclonal antibody M195 in patients with relapsed acute non-lymphoid leukemias (ANLL). To determine the pharmacology and dosimetry of radiolabeled M195. To study biological responses to M195 including host responses, cellular responses and leukemia responses.

Background and Rationale

ANLL. Long-term survival in ANLL with the best current chemotherapeutic regimens is generally less than 20% (190). Survival of patients who relapse or who fail first attempts at induction chemotherapy is far lower. Autologous or allogeneic bone marrow transplantation may improve survival, but only in a small subset of patients (191). There are no effective therapies for myelodys-plastic syndromes or chronic monocytic leukemias and long term survival in these diseases is rare. Among patients with chronic myeloid leukemias (CML), only allogeneic bone marrow transplant has had an impact on survival (192).

Monoclonal Antibody Therapy. Several pilot trials have been conducted using unlabeled antibodiese hematopoietic neoplasms (reviewed in 193). Toxicity was tolerable and responses were seen, but they were almost always transient. None of the original trials used antibodies with intrinsic cytotoxic capability and responses were probably abrogated by lack of effector functions, antigen modulation and human antimouse Ig responses. More recent trials (194,195) using radioisotope-labeled monoclonal antibodies have achieved high major response rates. These trials utilized large doses of $^{131}$I-labeled monoclonal antibodies to T-cell lymphomas, chronic lymphocytic leukemias, and nodular lymphomas. The major adverse reactions were hematologic, related to the high doses of radiation. In the trial with T cell lymphomas and CLL, remissions were short lived. It is too soon to know the long term outcome in the nodular lymphoma trials. No study of monoclonal antibodies has been completed with patients with ANLL, but three patients were treated (196) with minimal responses and toxicity with a cocktail of antibodies. These antibodies recognized different antigen targets than M195 recognizes. Despite large doses of antibody (up to several hundred mg), blast counts were suppressed only transiently in the three patients. All three patients had fever and one had urticaria due to the infusions, but the antibodies were not highly purified. We have seen minimal toxicity here in 30 patients with B-NHL, Hodgkins Disease, and T-NHL, treated with monoclonal antibodies OKB7 or R24, at doses ranging from 0.1 to 100 mg.

M195. Mouse monoclonal antibody M195 is a IgG2a developed at Sloan-Kettering Institute (196,197) which reacts with 60–70% of samples of blasts from patients with ANLL. M195 also binds to early meyloid cells (CFU-GM) and some monocytes but not to the earliest myeloid progenitors. The target antigen is not expressed on any other hematopoietic or non-hematopoietic tissue. Antibodies to a related antigen on the same protein (CD33), My9 and L4F3, are currently being used to purge bone marrow of ANLL before autologous transfusion (199,200). M195 is rapidly internalized into cells after binding and this effect can enhance delivery of radiometals, radioiodine or conjugated toxins into cells (201). M195 is able to kill leukemia cells with rabbit or guinea pig complement, but not by use of human complement or human antibody-dependent cellular cytotoxicity in vitro. Activation of these mediators in vitro has correlated with these effects in vivo (202), but it is not known if the lack of in vitro effects will predict lack of in vivo effects. Because M195 also reacts with early myeloid cells, normal marrow progenitors may be affected also.

Studies of M195 in Humans. In order to determine the toxicity, biodistribution, pharmacology and dosimetry of radiolabeled M195 in humans, a pilot trial involving patients with ANLL was initiated under IRB approval (#89-113A(1)) at Memorial Hospital in 1989.

Ten patients with myeloid leukemias were treated in a phase 1 trial with escalating doses of mouse monoclonal antibody M195, reactive with CD33, a glycoprotein found on myeloid leukemia blasts and early hematopoietic progenitor cells. M195 was trace-labeled with idodine-131 to allow detailed pharmacokinetic and dosimetric studies by serial sampling of blood and bone marrow and whole body gamma-camera imaging. Individual doses ranging from 1.5 mg to 19 mg and total doses, from 6 mg to 76 mg, were administered safely without toxicity. Median serum halflife was 52 hours and total body halflife was 53 hours. Volume of distribution was slightly larger than blood volume. In vivo absorption of M195 onto targets was demonstrated by biopsy, pharmacology, flow cytometry and imaging; saturation of available sites occurred at doses of 5 mg/m² or greater. The entire bone marrow was specifically and clearly imaged beginning within hours after injection; optimal imaging occurred at the lowest dose level because after saturation of binding sites in the bone marrow, excess $^{131}$I-M195 was visible in the blood vessels. Bone marrow biopsies demonstrated significant uptake of M195 as early as 1 hour after infusion in all patients. At the 5 mg/m² dose level, estimated total marrow uptake accounted for the majority of the injected dose. Toxicity was seen in one patient, who developed severe bone marrow pain in all areas of marrow. Aside from 30 to 60% increases in fibrinogen levels in 8 of 10 patients, including one patient with acute promyelocytic leukemia and disseminated intravascular coagulation, no biological, hematological, or biochemical effects were seen. MIRD dosimetry based on pharmacology, imaging and biopsy data demonstrated that with $^{131}$I-M195 an estimated 0.33 to 1.0 rad/mCi would be delivered to the whole body, 1.1 to 6.1 rad/mCi would be delivered to the plasma, and between 4 and 34 rad/mCi would be delivered to the red marrow compartment. Flow cytometry and radioimmunoassay analyses showed that the $^{131}$I-M195 was rapidly modulated with up to 70% of the bound IgG being internalized into target cells. Microdosimetric estimates based on biopsy data and internalization of radiolabel into leukemia cells demonstrated feasible delivery of up to 1 MeV to target cell nuclei with $^{123}$I, with trival radiation doses to the whole body. These data show that with isotope dose escalation, whole bone marrow ablative doses of $^{131}$I-M195 could be safely and easily achieved, and leukemia-specific purging doses of $^{123}$I-M195 might be possible. Moreover, because of the rapid, specific, and quantitive delivery to the bone marrow and the efficient internalization of M195 into target cells la vivo, delivery of other isotopes such as alpha emitters, toxins, or other biologically important molecules into leukemia cells or normal hematopoietic progenitor cells is feasible.

Microdosimetry of $^{131}$I. The localization of the M195 mAb on the surface of the leukemia cell and its subsequent incorporation into the cytoplasm presents an opportunity to select a radionuclide with properties that exploit this situation. Electron emissions that have a range on the order of a cell diameter (10–20 microns) deposit a large fraction of their energy within the cell (203). Electron capture (EC) is a mode of decay that gives rise to a large percentage of such low energy emissions. The isotopes of iodine that decay by EC include I-125 (T1/2=60 d) and I-123 (T-1/2=14 h), the latter being advantageous in terms of a physical half-life matching the expected biological clearance times. From a microdosimetric point of view, in cells on the order of 10–12$\mu$ in diameter, it is more effective than I-131.

However, technical problems of achieving adequate specific activity, supply of isotope and enormous cost make $^{123}$I unfeasible at this time. $^{131}$I also generates an equivalent number of low energy emission per disintegration and is technically and economically more feasible to use. With $^{131}$I-M195 we have estimated specific doses to the target cell nucleus of up to 1 MeV (about 250 rads) are achievable with a dose of M195 labeled with 110 mCi per mg (1 atom per IgG). At the same dose level, whole body radiation doses will be about 70 to 110 rads, and plasma doses 220 to 660 rads. The bone marrow dose is difficult to estimate but may be two to ten times the plasma dose, especially if the marrow is involved. Due to the additional auge flux in the target cells as noted above, we. may get 50% more radiation to the leukemia cells than to the normal marrow cells. Relative sensitivity of normal versus leukemic cells are unknown.

Limitations on Doses. The nonhematopoietic organ that will be dose limiting appears to be the liver. Because the liver may receive up to 4 rad/mCi in some patients, 500 mCi (2000 rad total to liver) would be an estimated endpoint.

The hematologic dose-limiting point may be less than this since in certain patients on the phase 1 trial, significant accumulation of $^{131}$I-M195 was seen in the marrow; which may receive in excess of 10 rad/mCi, although it was usually in the range of 2–6 rad/mCi. Thus, dose limiting hematologic toxicity may be reached in the range of 200 mCi injected dose. Because marrow dosimetry is not predictable yet, it is possible that complete marrow ablation may occur.

Patient Selection

A minimum of nine patients are treated.

Eligibility

1. Patients with acute non-lymphoid leukemia (ANLL) or chronic myelogenous leukemia in myeloblastic or accelerated phase (CML, MBL) or chronic myelomonocytic leukemia (CMMOL) in accelerated phase, who have relapsed from or failed conventional therapy and who are not eligible for other bone marrow transplantation protocols, are eligible.

2. Leukemic blasts must be positive for M195 antigen expression (greater than 25% positive cells by flow cytometry).
3. Patients must be off chemotherapy (except for hydroxyurea) and radiation therapy for at least four weeks prior to treatment. Hydroxyurea must be stopped at least 2 days prior to entering this trial with stable or rising WBC counts.
4. Patients must be expected to live six weeks after therapy.
5. Patients must have a Karnofsky performance status of 60% or greater.
6. Serum creatinine must be less than 2 mg/100 ml; serum bilirubin, less than 2 mg/100 ml; and prothrombin time, less than 1.3×control.
7. Patients must sign an Informed Consent to participate in the study.

Exclusions

1. Clinically significant cardiac disease (New York Heart Association Class III or IV).
2. Serious infections requiring amphotericin, or a positive blood culture within 10 days of treatment, serious pulmonary disease with <90 saturation or a CXR showing active disease or other serious illness.
3. Age <16 years. (Since we do not have pharmacologic data on smaller patients from the phase I trial #89–113.)
4. Prior mouse monoclonal antibody therapy if an anti-mouse Ig response is present.
5. Active CNS leukemia or cranial nerve involvement.
6. Pregnancy or lactation in women.
7. Recent CNS bleeding.
8. Known HIV infection, as additional complications may be expected.

M195 Antibody Production, Labelina

Production and Purification. Hybridoma ascites was produced in pristane-treated, irradiated mice. Only high titer ascites batches were pooled for purification. Cell-free fluid will be pooled and concentrated for purification.

Ascites and supernatants were tested for murine virus (MAP, MS6V, EdIM, thymic virus, LDH, MuLV (complete) LCM). Only ascites negative in these tests were pooled for purification.

M195 was purified from ascites by removal of lipoprotein by ultracentrifugation at 100,000 g and chromatographic fractionation and affinity chromatography on protein A.

Purified M195 was tested for absence of DNA and characterized by electrophoresis, HPLC, labeling characteristics and titer.

Preclinical Safety Testing. Purified M195 underwent safety testing including the pyrogenicity assay in rabbits, the limulus assay for endotoxin, sterility testing and general safety tests in small animals.

Only batches of M195 that satisfied the purity and safety criteria outlined above are used in the proposed study.

Labelina with Radionuclides. Two mg of M195 will be labeled with iodine-131 using aseptic pyrogen-free technique. Pure antibody will be isolated by exclusion chromatography. Unlabeled antibody will be added subsequently to bring the total antibody dose to 2 mg/m$^2$.

Treatment Plan. Patients are admitted to a single room. Patients are hydrated overnight at 150 cc/hr before treatment and begin allopurinol 300 mg TID orally at least 12 hours before treatment. Allopurinol will stop after 1 week. Patients begin Lugol's solution as early as 5 days before antibody treatment (if possible) and continue for 7 days after treatment. 400 mg potassium percholorate po bid is begun on the day before antibody treatment and continue for 4 days total.

Adminsitration of M195. Three patients are treated at each dose level. There are three isotope dose levels: 50 mCi/m$^2$, 70 mCi/m$^2$, 90 mCi/m$^2$ given in 2 divided doses of 25, 35, 45 mCi/m$^2$. Each patient is treated on days 1 and 3. The M195 is infused in 50 ml of saline/5% human serum albumin over 20 minutes. The dose of M195 is always 2 mg/m$^2$, although the isotope dose and the specific activity will escalate.

Retreatment. Patients with 50% or greater clearing of marrow blasts six weeks after the start of therapy may be treated again on the same schedule. HAMA+patients will be eligible for retreatment.

Patients are treated and isolated in a single room until certified as safe to leave by the Radiation Safety Service.

Evaluation

Pre-treatment Evaluation

1. History and physical examination.
2. Complete blood count, prothrombin time, partial thrambaplastin time, platelet count, thrombin time, fibrinogen, coagulagram.
3. Biochemical screening profile, electrolytes.
4. Serum creatinine.
5. Urinalysis including microscopy.
6. Serum for circulating M195 antigen.
7. 12-lead electrocardiogram.
8. Chest X-ray.
9. Bone marrow aspirate for morphology, blast count, and cytogenetics (if not previously done).
10. Serum sample for analysis of pre-treatment human antimouse Ig response.
11. Vital signs (pulse, blood pressure, respiratory rate and temperature.
12. Flow cytometry analysis of bone marrow and blood mononuclear cells for T, B, myeloid markers and M195 reactivity.
13. Thyroid function tests.
14. Bone marrow core biopsy for cellularity.

Post-Treatment Evaluation

1. Vital signs (pulse, blood pressure, respiratory rate, temperature), are monitored and recorded before treatment, every 30 minutes during infusion of M195, and 30 and 60 minutes after the end of infusion, and hourly thereafter for 4 hours. Less than 200 ml of blood is drawn during the one week of study.
2. Other tests are done as follows:

| Test | Timing |
|---|---|
| Physical exam and performance status | gd during treatment |
| CBC, differential, platelets | 6 hours post M195 therapy, then gd × 6 days, then as indicate |
| PT, PTT, fibrinogen | 6 hours post-treatment, gd × 6, then weekly |
| Urinalysis | daily × 6 days |
| Electrolytes, BUN, creatinine, Phos, Ca, Uric Acid | 6, 12 hours post therapy then gd × 6 days. |

-continued

| Test | Timing |
| --- | --- |
| Human antimouse Ig | 8 days after treatment, q4 weeks post-treatment × 2, then q8 weeks until EOS. |
| Isotope levels (green top) | 5, 10, 15, 30, 45, 60, 120, 240, 360, 480 min. after M195 dose #1, then pre- and post dose #2, then BID × 6 days. |
| Bone marrow biopsy for cellularity | Day #9. |
| Flow cytometry of peripheral blood | Days 4–6 |
| Bone marrow aspirate for morphology and blast count | Days 9 then Q14 d. |
| Gamma camera imaging (Nuclear Medicine) | Days 1–4 |
| Thyroid function tests | 3 months, 1 year |

Special Studies

Blood radioactivity levels are obtained by testing samples at the time intervals stated above and generating quantitative radioactive decay curves.

Blood cells are obtained at the times above and tested for expression of antigen, presence of mouse immunoglobulin, quantitation of isotope and leukemia cell phenotype.

Whole body imaging using a Gemini scanner to assess dosimetry to the whole body, liver, spleen and other major organs is done daily during treatment. Additional images may be necessary.

Pharmacokinetics of M195. Specimen collection: 1 ml of blood is collected at 5, 10, 15, 30, 45, 60, 120, 240, 360, 480 min and then pre-and post-infusions for 2 days.

M195 serum levels will be determined by $^{131}$I and by ELISA assay using the "double-antibody sandwich" technique. Each serum sample drawn above is assayed. Pretreatment serum is used as negative control. A standard curve is generated using known concentrations of mAb diluted in the patent's pretreatment serum. This assay can detect antibody concentrations as low as 20 ng/ml.

The total amount of blood drawn is less than 50 ml including standard admission bloods on admission, less than 80 ml on day 1 and less than 120 ml total for the remainder of the hospital stay.

Other Assays

M195 Activity Titers. Following infusions selected sera is tested for the presence of M195 activity using direct RIA.

Human Antimouse Ig Response. The patient's serum is assayed by the ELISA technique for the presence of immunoglobulin which binds to M195 coated microtiter plates.

Flow Cytometric Analysis of M195 Binding. Bone marrow and peripheral blood mononuclear cells are analyzed for binding of M195 and other markers by flow cytometric methods. Modulation of antigen is tested in blook at 24 hours as well. These specimens will need to be on ice.

Criteria for Being Evaluable

For toxicity: Patients receiving at least one dose of M195 should be evaluable for toxicity.

For therapeutic response: Patients receiving two doses of M195 are evaluated for therapeutic response.

Criteria for Being Not Evaluable

Patients are considered not evaluable for the following reasons:

1. Refusal to comply with the protocol for reasons other than toxicity or tumor progression.
2. Death from causes unrelated to the drug or tumor.
3. Failure to return for follow-up evaluation or treatment.

Toxicity

Toxicity is graded according to the common toxicity criteria developed by the NCI which are on file with the IRB.

Toxicity During Antibody Infusions. If grade I–II toxicity occurs, treatment may be continued at the same dose and schedule.

If grade III toxicity occurs, treatment may be continued at the descretion of the investigator, with a rate of M195 infusion that is slowed by 50% of the original rate. If grade III toxicity continues or recurs, retreatment is continued at 50% of that dose. If grade III toxicity persists at the lower dose, treatment is discontinued and the patient withdrawn from the study.

Other Toxicity. The maximum tolerated dose (MTD) is set at such time as when 2 of 3 patients at a dose level have grade III or greater non-hematologic toxicity. If this occurs at dose level two, then three additional patients are treated at dose level one. If this occurs at dose level three, then an addtional patient is treated at dose level two. If this occurs at dose level one then three additional patients are treated at one half the isotope dose given in dose level one.

Hematologic MTD. Failure of the return of WBC (normal or leukemic) after 5 weeks in 2 of 3 patients are considered MTD and additional patients are added as described in the Section above.

Patients who have an increase in blasts after administration of all doses of M195 or who develop new symptoms showing progression of disease are removed from study. In that case, alternative therapy is administered. If the leukemia remains stable four weeks after administration of M195, patients are kept on study, off therapy, until there is evidence of tumor progression.

Criteria for Removal From Study

Infusion is terminated for:

A. Fall in systolic blood pressure of more than 25 mm Hg.
B. Respiratory distress.
C. Pulse >130/min.
D. Temperature >39° C.
E. Clinician's judgement.
F. Patient's request.

Criteria for Therapeutic Response

Complete Remission. Achievement of a normocellular bone marrow with <5% blasts in a patient with HGB >9 gm %, WBC >3,000 and platelets >100,000.

Partial Remission. The achievement of a cellular bone marrow with 5–10% blasts with peripheral blood counts: HGB >9 gm %, WBC >3,000, platelets >100,000.

Minor Response and Stable Disease. Although drug-induced marrow hypoplasia or aplasia is recorded, it is not considered a therapuetic effect. Patients failing to achieve either a complete or partial remission are counted therapeutic failures.

Statistical Considerations. This is a Phase I study in which toxicity information as well as pharmacokinetic and radio-immunolocalization data is obtained. Other studies with mAbs have shown variability from patient to patient in pharmacokinetics of labeled mAb. It is not the purpose of this study to demonstrate statistically significant differences between these groups of patients treated at different dose levels or in responses of tumors.

Concurrent Medications. Any non-cytotoxic, non-chemotherapeutic medications needed in the management of the patient is allowed. Use of any treatment known to be effective in killing or altering leukemia cells will cause termination of the patient from the study.

Assent of a Minor. This study involves research which presents greater than minimal risk to children (46.404–45 code of Federal regulations Part 46). The assent of any minor patient should be obtained before the patient is entered onto this study.

Experiment 7

Introducing genetic information into Hematopoietic cells.

We have previously shown unique features of M195 which enable it to be used as a carrier of biologically important agents into specific cells: In experiments 1 and 2 we show specificity of binding to human leukemia cells and normal hematopoietic progenitor cells; In experiment 3 we show that binding of M195 is followed by internalization of the antibody and that which is attached to the antibody, for example an isotope such as iodine-125 or chelating agent with an isotope within.

We further showed that fragments of M195 comprising the hypervariable region will also be useful for internalization. In experiment 4 we show that internalization can be readily accomplished in a live human patient: The M195 can be injected intravenously and will target to specific cells of the bone marrow or blood and be bound internalized into those cells. It follows therefore that other important agents might be internalized into specific hematopoietic cells after targeting with M195. This should be accomplished in vitro, ex vivo, (as in a bone marrow culture before reinfusion) or in vivo.

One of the most important agents for delivery would be genetic information or genes. The most effective method for packaging genes is in the form of retroviral vectors. These can be constructed by well known methods familiar to those skilled in the art (204–206)

These methods of packaging genes have been available for more than five years. Some of the most important genes are those which regulate or produce hematopoietic cells or proteins comprising hematopoietic cells. This is because defective genes in hematopoietic cells are responsible for human disease afflicting millions of people. These diseases include sickle cell anemia, thalasernia, leukemias and myelodysplastic syndromes, and are well known to those familiar with treating them (207). Hematopoietic cell genes have therefore been the focus of much work and those skilled in the art have provided methods for introduction of genes into mouse and human hematopoietic cells (208–210). In this last work, a mouse model of thalassernia was corrected by introduction of new genes into the germ line.

Therefore, the need for genetic therapy is clear, the methods for packaging genes that will enable their subsequent expression are well known, and the use of retroviral vectors to carry genes into cells are well known. What is lacking is a method for specific targeting of the retroviral vector carrying hematopoietic genes into hematopoietic progenitor cells. M195 being specific for these cells (also known as CFU-GM, CFU-GEMUR, and BFU-E) can serve this function. One must attach the M195 antibody to the outside of the retroviral vector so as to target the vector to the appropriate cell where it and the vector, containing the genes will be internalized into the cells.

Methods for attaching antibodies to viruses are known (211). In similar fashion, M195 can be attached to the vector using a rabbit anti-mouse IgG bridge which links to a monoclonal antibody which binds to the retroviral vector surface protein (FIG. 19). Methods to produce and purify M195 are described in experiments 1 and 2 here. Methods to produce monoclonal antibodies to retrovirus surface proteins have been well known for ten years (212). Rabbit polyclonal antibody against mouse monoclonal antibody which can be used to link the two monoclonal antibodies together can be purchased from commercial sources. (TAGO, DAKO, and SIGMA).

The three antibodies are linked to the virus in a manner analogous to linking three similar antibodies in a bridge to red blood cells surfaces and are well known (213). In this method, (FIG. 19) monoclonal antibody against the retrovirus is incubated for 1 hour at 4° C. with the retrovirus at antibody excess (50–100 μg/ml antibody). Unbound antibody is removed by ultracentrifugation of the virus onto a sucrose cushion. An excess of the rabbit antibody is next incubated similarly with the monoclonal antibody coated retrovirus, followed by ultracentrifugation to rid unbound rabbit antibody; finally the M195 is added at 50 μg–100 μm/ml, incubated and washed as above. The resulting structure has the bridge as seen in FIG. 19. Because the M195 is specific for hematopoietic progenitors it will bind the virus only to them. Because of the unique feature of M195 to internalize, the vector will be brought into the target cells. This process should be achieved by mixing the M195 -vector contruct with normal human bone marrow ex vivo followed by reinfusion of the marrow or by intravenous infusion of the construct into patients. Analogously genes may also be delivered into neoplastic cells such as leukemia cells for the purpose of inserting anti-oncogenes, suppressor genes, or other genes that might alter their function.

Alternative methods for attaching the M195 to the retrovirus can be used such as genetically attaching the M195 to the retroviral surface protein, linking the M195 to shaph A protein A which is on the retroviral surface, or chemically attaching the M195 to the virus coat. (FIG. 18).

Experiment 8

Humanized antibody

The benefits of the M195 antibody have been shown above. However, because it is a mouse derived antibody it may cause adverse effects when administered to a human patient because it will be recognized as foreign, thus causing an immunogenic response. This has lead researchers to "humanize" the antibody by substituting human portions for those of the mouse antibody, in an effort to reduce the immunogenic response triggered by the M195 antibody. Well known techniques of genetic engineering are employed to effect these changes.

This humanizing may be done on varying levels. One may replace the mouse constant region of the antibody with a human constant region (214–216). This leaves the region which binds to the antigen completely in tact, thus the binding capabilities of the antibody should remain. Taking it one step further, one may construct an antibody which contains the CDR sequences of the mouse antibody grafted into the human antibody. (217–219). Additionally, with the aid of computer modeling techniques it is possible to identify, on an amino acid by amino acid level, those amino acids which play a role in the variable binding region and those which do not. (MicroGenie Sequence Analysis Software, Beckman; Encad; Midas). Using this method the optimal humanized sequence which retains the desired binding level can be determined. From this one can generate a polypeptide with the desired sequence from a sequencer.

CHIMERIC M195. Chimeric monoclonal antibodies (mAb) M195-IgG1, and M195-IgG3 (produced by PDL) were tested in the Hematopoietic Cancer Immunochemistry Laboratory at MSKCC. Hybridomas making both chimeric mAb grow well in culture producing about 5 μg per ml of mAb. Both mAb can be purified by 50% neutral ammonium sulfate precipitation followed by affinity chromatography on Protein A sepharose. The affinity of both mAb as tested by Scatchard analysis is similar to the original mouse M195 (about $10^9$ L/M). Mouse M195 competes for binding of chimeric M195. Chimeric Ig1 M195 can be grown in nude mice, BALB/c mice, and CByF1 mice as ascites producing about 1 mg mAb per ml which can be purified as in B. Both chimeric mAb can be radiolabeled to high specific activity with $^{125}$Iodine. Both mAb internalize into target leukemia cells. Both chimeric mAb bind specifically to target myeloid leukemia cells. Both chimeric mAb will activate rabbit complement to kill target leukemia cells at concentrations of mAb below 1 µg/ml. Neither chimeric mAb has significant complement activity with human complement. Both chimeric mAb will mediate cell mediated killing (ADCC) of target leukemia cells at concentrations of 1 to 10 µg/ml and effector to target ratios of 25–100:1.

In Summary. Both chimeric M195 mAb retain all of the characteristics of the original mouse M195 with the added features of human constant regions and human ADCC function.

REFERENCES

1. Tanimoto M., Scheinberg D. A., Cordon-Cardo C., et al. Leukemia 3:339–348 (1989).
2. Scheinberg D. A., Tanimoto M., McKenzie S., et al. Leukemia 3:440–445 (1989).
3. Bernstein I. D., Singer J. W., Andrews R. G., et al. J. Clin. Invest. 79:1153–1159 (1987).
4. Griffin J. D., Linch D., Sabbath K., et al. Leukemia Res. 8:521–534 (1984).
5. Divgi C. R., Minniti J. G., Old L. J., Scheinberg D. A. Amer. Assoc. Cancer Res. 30: Abs #1606 (1989).
6. Houghton A. N., Mintzer D., Cordon-Cardo C., et al. Proc. Natl. Acad. Sci. U.S.A 82:1242–1246 (1985).
7. Clarkson B. D., Gee T. S., Mertelsmann R., et al. CRC critical review in Oncology/Hematology 4:221–248 (1986).
8. Gale R. P., Horowitz M. M., Biggs J. C., et al. Lancet 8647:1119–1121 (1989).
9. Clarkson B. D. J. Clin. Oncol. 3:135–139 (1985).
10. Civin C. I., Mirro J., Banquerigo M. L., Blood 57:842–845 (1981).
11. Griffen J. D., Ritz J., Nadler L. M., Schlossman S. F., J. Clin. Invest 68:932–941 (1981).
12. Perussia B., Trichieri G., Lebman D., Jankiewicz J., Lange B., Rovera G. Blood 59:382–392 (1982).
13. Andrews R. G., Torok-Storb B., Bernstein I. D. Blood 62:124–132 (1983).
14. Griffin J. D., Linch D., Sabbath K., Larcom P., Schlossman S. F. Leuk. Res. 8:521–534 (1984).
15. Civin C. I., Strauss L. C., Brovall C., Fackler M. J., Schwartz J. F., Shaper J. H. J. Immunol. 133L157–165 (1984).
16. Katz F. E., Tindle R., Sutherland D. R., Greaves M. F. Leuk. Res. 9:191–198 (1985).
17. Askew D. S., Eaves A. C., Takei F. Leuk. Res. 9:135–145 (1985).
18. Ferrero D., Gab bianelli M., Peschle C., Lange B., Rovera G. Blood 66:946–502 (1985).
19. Drexler H. G., Sagawa K., Menon M., Minowada J. Leuk. Res. 10:17–23 (1986).
19A. Katz F. E., Tindle R., Sutherland D. R., Geraves M. F. Leuk. Res. 91:191–198 (1985).
20. Peng R., Al-Katib A., Knowles D. M., Lu L., Borxmeyer H., Tolidjiian B., Chiao J-W, Koziner B., Wang C. Y. Blood 64:1169–1178 (1984).
21. Wisniewski D., Knowles R., Wachter M., Strife A., Clarkson B. Blood 69:419–429 (1987).
22. Strife A., Lambek C., Wisniewski D., Gulati S., Gasson J. C., Golde D. W., Welte K., Gabrilove J. L., Clarkson B. Blood 69:1508–1523 (1987).
23. Ball E. D., Mills L. E., Coughlin C. T., Beck R., Cornwell G. G. Blood 68:1311–1315 (1986).
24. Ball E. D., bernier G. M., Cornwell G. G., McIntyre O. R., O'Donnel J. F., Fanger M. W. Blood 62:1203–1210 (1983).
25. Foon K. A., Todd R. F. Blood 68:1–31 (1986).
26. Alvey P. L., Greaves M. F. 1:527–540 (1987).
27. Wilson W. E. C., Walker I. R., Saeed N., McBride J. A. Blood 68:1355–1362 (1986).
28. Griffin J. D., Linch D., Sabbath F., Larcam P., Schlossman S. F. Leuk Res 8:521–534 (1984).
29. Dinndorf P. A., Andrews R. G., Benjamin D., Ridgway D., Wolff L., Bernstein I. D. Blood 67:1048–1053 (1986).
30. Pessano S. Palumbo A. Ferrero D., Pagliardi G. L., Bottero L., Lai S. k., Meo P., Carter C., Hubbell H., Lange B., Rovera G. Blood 64:275–281 (1984).
31. Griffin J. D., Mayer R. J., Weinstein H. J., Rosenthal D. S., Coral F. S., Bevendga R. P., Schlossman S. F. Blood 62:557–563 (1983).
32. Van der Reijden H. J., Van Rhenen D. J., Lansdorp P. M., Van't Veer M. D., Langenhuijsen M. M. A. C., Engelfriet C. P., Von dem Borne A. F. G. K. Blood 61:443–448 (1983).
33. Linch D. C., ALlen C., Beverley P. C. L., Bynoe A. G., Scott C. S., Hogg N. Blood 63:566–573 (1984).
34. Drexler H. G., Minowada J. Leuk. Res. 10:279–290 (1986).
35. Ball E. D., Bernier G. M., Cornwell G. G., McIntyre O. R., O'Donnel J. F., Fanger M. W. Blood 62:1203–1210 (1983).
36. Ball E. D., Mills L. E., Coughlin C. T., Beck R., Cornwell G. G. Blood 68:1311–1315 (1986).
37. Griffin J. D., Lowenberg B. Blood 68:1185–1195 (1986).
38. Lange B., Ferrero D., Pessano S., Palumbo A., Faust J., MeO P., Rovero G. Blood 64:693–700 (1984).
39. Sabbath K. D., Ball E. D., Larcom P., Davis R. B., Griffin J. D. J. Clin. Invest. 75:746–753 (1985).
40. Lowenberg B., Bauman J. G. J. Blood 66:1225–1232 (1985).
41. Peiper S. C., Lemons R. S., Ashmun R. A., Look A. T. In:McMichael A. J., ed. Leucocyte Typing III. New York: Oxford University PRess, 622–625 (1987).
42. Berenson R. J., Bensinger W. I., Kalamasz D. J. Immunol. Methods 91:11–19 (1986).
43. Civin C. I., Strauss L. C., Brovall C., Fackler M. J., Schwartz J. F., Shaper J. H. J. Immunol. 133:157–165 (1984).
44. Strauss L. C., Rowley S. D., LaRussa V. F., Sharkis S. J., Stuart R. K., Civin C. I. Exp. Hematol. 14:878–886 (1986).
45. Askew D. S., Eaves A. C., Eaves C. J., Takei F. Blood 67:2098–1102 (1986).
46. Askew D. S., Eaves A. C., Takei F. Leuk. Res. 9:135–145 (1985).
47. Bernstein J. D., Singer J. W., Andrews R. G., Keeting A., Powell J. S., Bjornson B. H., Cuttner J., Najfeld V., Reaman G., Raskin W., Sutton D. M. C. Fialkow P. J. J. Clin. Invest. 79:1153–1159 (1987).
48. Andrews R. G., Takahashi M., Segal G. M., Powell J. S., Bernstein I. D., Singer J. W., Blood 68:1030–1035 (1986).
49. Andrews R. G., Torok-Storb B., Bernstein I. D., Blood 62:124–132 (1983).
50. Griffin J. D., Ritz J., Nadler L. M., Schlossman S. F., J. Clin. Invest 68:932–941 (1981).
51. Peng R., Al-Katib A., Knowles D. M., Lu L., Broxmeyer H., Tolidjian B., Chiao J-W, Koziner B., Wang C. Y., Blood 64:1169–1178 (1984).

52. Wisniewski D., Knowles R., Wachter M., Strife A., Clarkson B., Blood 69:419–429 (1987).
53. Kohler G., Milstein C. Nature 256:495–497 (1975).
54. Larson S. M. J. Nucl. Med 26:538–545 (1985).
55. Houghton A. N., Scheinberg D. A. Sem. Oncol. 13:165–179 (1986).
56. Goldenberg D. M., Deland F., Kim E. et al. N. Engl. J. Med. 298:1384–1388 (1978).
57. Bunn P. A., Jr., Carrasquillo J. A., Keenan A. M. et al. Lancet 2:1219–1221 (1984).
58. Larson S. M., Brown J. P., Wright P. W. et al. J. Nucl. Med 24:123–129 (1983).
59. Press O. W., Eary J. F., Badger C. C. et al. J. Clin. Oncol 7:1027–1038 (1989).
60. Rosen S., Zimmer A., Golman-Leikin R. et al. J. Clin. Oncol. 5:562–573 (1987).
61. Carrasquillo J. A., Bunn P. A., Keenan A. A. et al. N. Engl. J. Med. 315:673–680 (1986).
62. Eptein A. L., Zimmer A. M., Spies S. M. et al., Cavalli F., Bonadonna G., Rozencweig M., eds Boston Martinus Nijhoff (1985).
63. DeNardo S. J., DeNardo G. L., O'Grady L. F. et al. Antibody Immunoconj. Radiopharm. 1:17–33 (1988).
64. Rao D. V., Narra V. R., Howell R. W. et al. Lancet vol.2:650–653 (Sep. 16, 1989).
65. Woo D. V., Li D., Mattis J. A. et al. Cancer Res. 49:2952–2952 (1989).
66. Scheinberg D. A., Strand M. Cancer Res. 43:265–272 (1983).
67. Khaw B. A., Cooney J., Edgington T., et al. J. Nucl. Med. 27:1293–1299 (1986).
68. Carrasquillo J. A., Mulshine J. L., Bunn P. A., Jr. et al. J. Nucl. Med. 28:281–287 (1987).
69. Anderson W. M., Strand M., NCI Monogr 3:149–151.
70. Lamm M. E., Boyse E. A., Old L. J. et al. J. Immunol. 101:99–103 (1968)
71. Shawler D. L., Micelli M. C., Wormsley S. B., Royston I., Dillman R. O. Cancer Res. 44:5921–5927 (1984).
72. Press O. W., Farr A. G., Borroz K. I. et al. Cancer Res. 49:4906–49012 (1989).
73. Matzku S., Brocker E. -B., Brugen J. et al. Cancer Res. 46:3848–3854 (1986).
74. Wang B. S., Lumanglas A. L., Silva J. et al. Cell Immunol. 106:12–21 (1987).
75. Olsnes S., Sandvig K., Petersen O. W., van Deurs B. Immunol. Today 10:290–295 (1989).
76. Kirsch M. E., Hammerling, U. L. *J Immunol* 127:805–910. 1981.
77. Bernstein I. D., Tam M. R., Nowinski R. C. *Science* 207:68–71. 1980.
78. Scheinberg D. A., and Strand M. *Cancer Res.* 42:44–49, 1982.
79. Scheinberg D. A., Strand M., and Gansow O. A. *Science* 215:1511–1513, 1982.
80. Nadler L. M., Stashenko P., Hardy R., et al: *Cancer Res* 40:3147–3154, 1980.
81. Shawler D. L., Miceli M. C., Wormsely S. B., et al: *Cancer Res* 44:5921–5927, 1984.
82. Sastry K. S. R., Rao D. V. Dosimetry of low energy electrons. Rao D. V., Chandra R., Graham M. C. eds. *In: Physics of Nuclear Medicine*, American Association of Physicists in Medicine, 1984.
83. Rao D. V., Narra V. R., Howell R. W., Govelitz G. F., Sastry KSR. In vivo radiotoxicity of DNA-incorporated $^{125}$I compared with that of densely ionizing alpha-particles. *Lancet* 650–653, 1989.
84. Griffin J. D., Linch D., Sabbath F., Larcam P., Schlossman S. F. Leut Res 8:521–534, 1984.
85. Sabbath K. D., Ball E. D., Larcom P., Davis R. B., Griffin J. D. *J. Clin. Invest* 75:746–753, 1985.
86. Bernstein I. D., Singer J. W., Andrews R. G., Keeting A., Powell J. S., Bjornson B. H., Cuttner J., Najfeld V., Reaman G. Raskind W., Sutton D. M. C., Fialkow P. J. *J. Clin. Invest* 79:1153–1159, 1987.
87. Andrews R. G., Takahashi M., Segal G. M., Powell J. S., Bernstein I. D., Singer J. W. *Blood* 68:1030–1035, 1986.
88. Tanimoto M., Scheinberg D. A., Cordon-Cardo C., Huie D., Clarkson B. D., and Old L. J. *Leukemia* 3:339–348, 1989.
89. Scheinberg D. A., Tanimoto M., McKenzie S., Strife A., Old L. J., and Clarkson B.D. *Leukemia* 3:440–445, 1989.
90. Robertson M. J., Griffin J., Soiffer R., Anderson K., Freedman A. S., Nadler L. M., Ervin T., Ritz J. *Blood* 74:283a, 1989.
91. Lemoli R. M., Gulati S. C., Scheinberg D. A., Gasparetto C., Moore M. A. S., Clarkson B. D., Gee T. *Blood* 74:280a, 1989.
92. Waldmann, T. A. (1989) Annu. Rev. Biochem. 58, 875–911.
93. Uchiyama, T., Broder, S. & Waldmann, T. A. (1981) J. Immunol. 126, 1393–1397.
94. Leonard, W. J., Depper, J. M., Uchiyama, T., Smith, K. A., Waldmann, T. A. & Greene, W. C. (1982) Nature 300, 267–269.
95. Gilboa, E., Retroviral Gene Transfer: Application to Human Therapy, Retroviruses and Disease (1989) Academic Press, pp. 95–111.
96. Kabat, E., et al., Sequences of Proteins of Immunological Interest, U.S. Department of Health and Human Services, (1987).
97. Cholthia and Lesk, J. Mol. Biol., 196, 901–917 (1987).
98. Morrison, S. L., Johnson, M. J., Herzenberg, L. A., Oi, V. T., Proc. Natl. Acad. Sci. U.S.A., 81: 6851–6855 (1984).
99. Jones, P. T., Dear, P. H. Foote, J., Neuberger, M. S. & Winter, G. (1986) Nature (London) 321:522–525.
100. Verhoeyen, M., Milstein, C. & Winter, G. (1988) Science 239:1534–1536.
101. Reichmann, L. Clark, M., Waldmann, H. & Winter, G. (1988) Nature (London) 332:323–327.
102. PCT International Patent Publication No. WO 89/09622, published Oct. 19, 1989 entitled "IL-2 Receptor Specific Chimeric Antibodies".
103. Hutson et al., Proc. Natl. Acad. Sci. U.S.A., 85, 5879–5883 (1988).
104. Bird et al., Science, 242, 423–426 (1988).
104A. Cairncross J. C., Mattes M. J., Beresford H. R., Albino A. P., Houghton A. N., Lloyd K. O., Old L. J., Proc. Natl. Acad. Sci. U.S.A. 79:5641–5645 (1982).
104B. Shiku H. Takahashi T., Oettgen H. F. Old L. J., J. Exp. Med. 144:873–881 (1976).
105. Mattes J. M., Tanimoto M., Pollack M. S., Maurer D. H., J. Immunol. Methods 61:145–150 (1983).
106. Cayre Y., Raynal M. C., Darzykiewicz Z., Dorner M. H., Proc. Natl. Acad. Sci. U.S.A. 84:7619–7623 (1987).
107. Welt S., Carswell E. A., Vogel C. W., Oettgen H. F., Old L. J., Clin. Immunol. Immunopathol. 45:214–229 (1987).
108. Old L. J., Stockert E., Boyse E. A., Kim J. H., J. Exp. Med. 127:523–539 (1968).
109. Scheinberg D. A., Tanimoto M., McKenzie S., Strife A., Old L. J., Clarkson B. D., Leukemia 3:440–445 (1989).
110. Berkowitz R. S., Umpierre S. A., Goldstein D. P., Andersen D. J., Gynecol. Oncol. 29:94–100 (1988).
111. Sakamoto J., Furukawa K., Cordon-Cardo C., Yin B. W. T., Rettig W. J., Oettgen H. F., Old L. J., Lloyd K. O. Cancer Res. 46:1553–1561 (1986).

112. Drexler H. G., Sagawa K., Menon M., Minowada J., Leukemia Res 10:17–23 (1986).
113. McMichael A. J., ed. Leukocyte Typing III. New York: Oxford University Press, 577–602 (1987).
114. Krolick K. A., Villenmez C., Isakson P., Uhr J. W., Vitetta E. S., Proc. Natl. Acad. Sci. U.S.A. 77:5419–5423 (1980).
115. Shimazaki C., Wisniewski D., Scheinberg D. A., Atpodien J., Strife A., Gulati S., Fried J. Wisniewolski R., Wang C. Y., Clarkson B. D., Blood 72:1248–1254 (1988).
116. Lemoli R. M., Gulati S. C., Scheinberg D. A., Gasparetto C., Moore M. A. S., Clarkson B. D., Gee T., Blood 74 (7):suppl, p280a abstract (1989).
117. Hudson, Anne-Marie, Makrynikola, V., Kabral A., Bradstock K. F., Immunophenotypic . . . Blood, 74 (6):2112–2120 (Nov. 1, 1989).
118. Tanimoto M., Scheinberg D. A., Cardo C. C., Huie D., Clarkson B. D., Old L. J. Leukemia 3:339–348 (1989).
119. Andrews R. G., Takahashi M., Segal G. M., Powell J. S., Bernstein I. D., Singer J. W. Blood 68:1030–1035 (1986).
120. Bennett J. M., Catovsky D., Daniel M. T., Flandrin G., Galton D. A. G., Gralnick H., Sultan C. Ann. Intern. Med. 103:626–629 (1985).
121. Peiper S. C., Lemons R. S., Ashmun R. A., Look A. T. In:mcMichael A. J., ed. Leukocyte Typing III. Oxford: Oxford University Press, 622–625 (1986).
122. Alvey P. L., Greaves M. F. Leukemia 1:527–540 (1987).
123. Neame P. B., Soamboonsrup P., Browman G. P., Meyer R. M., Bender A., Wilson W. E. C., Walker I. R, Saeed N., McBride J. A. Blood 68:1355–1362 (1986).
124. Pessano S., Palumbo A., Ferrero D., Pagliardi G. L., Bottero L., Lai S. K., Meo P., Carter C., Hubbell H., Lange B., Rovera G. Blood 64:275–281 (1984).
125. Griffin J. D., Mayer R. J., Weinstein H. J., Rosenthal D. S., Coral F. S., Bevendga R. P., Schlossman S. f. Blood 62:557–563.
126. Linch D. C., Allen C., Beverley P. C. L., Bynoe A. G., Scott C. S., Hogg N. Blood 63:566–573 (1984).
127. Bernstein I. D., Singer J. W., Andrews R. G., Keating A., Powell J. S., Bjornson B. H., Cuttner J., Najfeld V., Reaman G., Raskind W., Sutton D. M. C., Fialkow P. J. J. Clin. Invest. 79:1153–1159 (1987).
128. Tanimoto M., Scheinberg D. A., Cordon-Cardo C., Huie D., Clarkson B. D., Old L. J., Leukemia 3:339–348 (1989).
129. Scheinberg D. A., Tanimoto M., McKenzie S., Strife A., Old L. J., Clarkson B. D., Leukemia 3:440–445 (1989).
130. Mittler R. S., Talle M. A., Carpender K. et al. J. Immuno. 131:1754–1761 (1983).
131. Nemerow G. R., Wolfert R., McNaughton M. E. et al. J. Virol. 55:347–351 (1985).
132. Hunter W. M., Greenwood F. C., Nature 194:495–496 (1962).
133. Lindmo T., Boven E., Cuttitta F. et al. J. Immunol. Methods. 72:77–89 (1984).
134. Krejcarek G. E., Tucker K. L. Biochem. Biophy. Res. Commun. 77:581–585 (1977).
135. Brechbiel, M. W., Gansow, O. A., Atchor, R. W., et al., Inorg. Chem. 25:2772–2781 (1986). 89.
136. Divgi C. R., Minniti J. G., Old L. J., Scheinberg D. A. Cancer Res Suppl. Vol. 30:404a, 1989.
137. Scheinberg D. A., Straus D. J., Yeh S. D., Divgi C. R., Garin-Chesa P., Graham M., Pentlow K., Coit D., Oettgen H. F., Old L. J. J. Clin. Oncol. :792–803. 1990.
138. Hunter W. M. In: D. M. Weir (ed.), Handbook of Experimental Immunology. F. A. Davis Co., Philadelphia. 1967.
139. Snyder W. S., Ford M. R., Warner G. G., Watson S. B. MIRD Pamphlet No. 11. The Society of Nuclear Medicine, Neo York, N.Y., 1975.
140. Kerieakes J., Seltzer R., Blackburn B., Saenger E. Health Physics 11:999, 1965.
141. Kassis A. I., Adelstein S. J., Haycock C., Sastry, K. R. S. Radiat Res. 84:407–425, 1980.
142. Browne E., Firestone R. B. Table of Radioactive Isotopes. Wiley Publishers, New York, 1986.
143. Shleien B., Terpilak M. S. eds The Health Physics and Radiological Health Handbook. Nucleon Lecterns Associates, Inc., Olney, Md., 1984.
144. Hiddemann W., Clarkson B. D., Büchner T., Melamed M. R., Andreeff M. Blood 59:216–221, 1982.
145. Bigler R. E., Zanzonico P., Leonard R., Cosma H., et al. Bone marrow dosimetry for monoclonal antibody therapy. Proceedings of the Fourth International Symposium on Radiopharmaceutical Dosimetry, Oak Ridge, Tenn., 1985.
146. Solomon D. H. Treatment of Graves Hyperthyroidism. In: Werners—The Thyroid A Fundamental and Clinical Text, p998. S. Ingbar and L. Braverman—Eds. J. B. Lippincott, Philadelphia.
147. Houghton A. N., Scheinberg D. A. Sem Oncol 13:165–179, 1986.
148. Collins S. S., Gallo R. C., Gallagher RE: Nature 270:347, 1977.
149. Wisniewski D., Strife A., Arlin Z., Knowles R., Lambek C., Gulati S. C., McHendry B., McKenzie S., Clarkson B. D.: Leukemia 3:446, 1989.
150. Strife A., Lambek C., Wisniewski D., Gulati S. C., Gasson J. C., Golde D. W., Welte K., Gabrilove J. L., Clarkson B. D.: Blood 69:1508, 1987.
151. Tanimoto M., Scheinberg D. A., Cordon-Cardo C., Huie D., Clarkson B. D., Old L. J.: Leukemia 3:339, 1989.
152. Civin I. C., Stauss L. C., Brovall C., Fackler M. G., Schwartz J. F., Shaper J. H.: J. Immunol. 133: 157, 1984.
153. Golde D. W., Quan S. G.: Blood 52:1068, 1979.
154. Smith C., Gasparetto C., Collins N., Gillio A., Meunch M., O'Reilly R. J., Moore M. A. S.: Purification and partial characterization of a human pre-CFU percursor population. (Submitted).
155. Lemoli R. M., Gulati, S. C., Strife A., Lambek C., Perez A., Clarkson B. D.: Proliferative response of human acute myeloid leukemia cells and normal marrow enriched progenitor cells to human recombinant growth factors IL3, GM-CSF and G-CSF alone and in combination. (in press—Blood 1991).
156. Sharkis S. J., Santos G. W., Colvin O. M.: Blood 55:521, 1980.
157. Stewart P., Buckner C. D., Bensinger W. Appelbaum F. R., Fefer A., Clift R., Storb R., Sanders J., Meyers J., Hill R., Thomas E. D.: Exp. Hematol 13:267, 1985.
158. Yeager A. M., Keizer H., Santos G. W., Saral R., Colvin O. M., N. Engl. J. Med. 315:141, 1986.
159. Gorin N. C., Aegerter P., Avvert B., the EBMTG: Autologous bone marrow transplantation (AuBMT) for acute leukemia in remission: An analysis on 1322 cases. Bone marrow Transplantation 4:3, 1989 (Suppl 2).
160. Scheinberg D. A., Tanimoto M., McKenzie S., Strife A., Old L. J., Clarkson B. D.: Leukemia 3:440, 1989.
162. Griffin J. D., Ritz J., Nadler L. M., Schlossman S. F.: J. Clin. Invest. 68:932, 1981.
163. Ball E. D., Bernier G. M., Corkwell G. G., McIntyre O. R., O'Donnel J. F., Fanger M. W.: Blood 62:1203, 1983.
164. Ball E. D.: Bone Marrow Transplantation 3:387, 1988.
165. Ball E. D., Mills L. E., Gibbons G., Cornwell G. G., Davis B. H., Blood 75:1199, 1990.

166. Robertson M. J., Griffin J., Soiffer r., Anderson K., Blood 74 (1): 283a, 1989.
167. Chang T. T., Gulati S. C., Chan T. C., Colvin O. M., Clarkson B. D.: Cancer Res 47:119, 1987.
168. Lemoli R. M., Gulati S. C.: Exp. Hematol. 18:1008, 199.
169. Tamayo E., Herve P.: Exp. Hematol 16:97, 1988.
170. DeCormick E., Tamayo E., Herve P.: Bone Marrow Transplantation 5:13, 1990.
171. Nara N., Suzuki T., Yamashita Y., Murohashi I., Aoki N.: Cancer Res 48:2348, 1988.
172. Sabbath T. H., Ball E. D., Lorcam P., Davis R. B., Griffin J. D.: J. Clin. Invest. 75:746, 1985.
173. Wouters R., Lowenberg B.: Blood 63:684, 1984.
174. Pessano S., Palumbo A., Ferrero D., Pagliardi G. L., Blood 64:275, 1984.
175. Uckum F. M., Gajl-Peczalska K., Meyers D. E., Ramsay N. C., Blood 69:361, 1987.
176. De Fabritiis P., Bregni M., Lipton J., Greenberger J., Blood 65:1064, 1985.
177. Gulati S. C., Shank B., Sarris A., Berman E., Gee T., Bone Marrow Transplantation 4:116, 1989.
179. Keizer H., Stuart R. K., Broxmeyer R., Beschormer W. E., Blood 65:1504, 1985.
180. Andrews R. G., Singer T. W., Bernstein I. D.: Blood 67:842, 1986.
181. Brandt J., Baird N., Lu L., Srour E., Hoffman R.: J Clin Invest 82:1017, 1988.
182. Andrews R. G., Singer J. W., Bernstein I. D.: J of Exp Med 169:1721, 1989.
183. Berenson R. J., Andrews R. G., Bensinger W. I., Kalamasz D. F., J. Clin Invest 81:951, 1988.
184. Besinger W. I., Berenson R. J., Andrews R. G., Kalamasz D. F., Bone Marrow Transplantation 4:86, 1989 (Suppl 2).
185. Siena S., Bregni M., Brando B., Ravagnoni F., Bonadonna G., Blood 74:1905, 1989.
186. Moore M. A. S., Warren D.: Proc Natl Acad Sci U.S.A. 84:7134, 1987.
187. Iscove N. N., Shaw A. R., Keller G.: J of Immunol 142:2332, 1989.
188. Rowley S. D., Jones R. J., Piantadosi S., Brovine H. G., Blood 74:501, 1989.
189. Lemoli R. M., Tafuri A., Strife A., Andreeff M., Clarkson B. D., Gulati S. C.: Abstract accepted, 1990.
190. Clarkson B. D., Gee T. S., Mertelsmann R., et al. CRC critical review in Oncology/Hematology 4:221–248, 1986.
191. Gale R. P., Horowitz M. M., Biggs J. C., et al. Lancet 8647:1119–1121, 1989.
192. Clarkson B. D. J Clin Oncol 3:135–139, 1985.
193. Scheinberg D. A., Houghton A. N. Oncology 1:31–40, 1987.
194. Rosen S. T., Zimmer A. M., et al. J Clin Oncol 5:562–573, 1987.
195. Press O., Eary J., Badger C. C., et al. J Clin Oncol 17:1027–1038, 1989.
196. Ball E. D., Berneri G. M., Cornwell G. G., et al. Blood 62: 1203–1210, 1983.
197. Tanimoto M., Scheinberg D. A., Cordon-Carado C., et al. Leukemia 3:339–348, 1989.
198. Scheinberg D. A., Tanimoto M., McKenzie S., et al. Leukemia 3:440–445, 1989.
199. Bernstein I. D., Singer J. W., Andrews R. G., et al. J Clin Invest 79:1153–1159, 1987.
200. Griffin J. D., Linch D., Sabbath K., et al. Leukemia Res 8:521–534, 1984.
201. Divgi C. R., Minniti J. G., Old L. J., Scheinberg D. A. Amer Assoc Cancer REs 30: Abs #1606, 1989.
202. Houghton A. N., Mintzer D., Cordon-Cardo C., et al. Proc Natl Acad Sci USA 82:1242–1246, 1985.
203. Kassis A. I., Adelstein S. J., Haycock C., Sastry, K. S. R. Radiation Research 84, 407–425, 1980.
204. Coffin, J. M. in RNA Tumor Viruses, Supplement, eds. Weiss, R., Teich, N., Varmus, H. & Coffin, J. (Cold Spring Harbor., Cols Spring Harbor, N.Y.), pp. 36–73 (1985).
205. Temin, H. M. in Gene Transfer, ed. Kucherlapati, R. (Plenum, New York), pp. 149–187.
206. Gilboa, E. BioEssays 5, 252–258.
207. Williams et al., *Hematology,* 4th edition, McGraw Hill, 1990.
208. Karlssan et al, PNAS 85:6062 (1988).
209. Gruber et al. *Science* 230:1057 (1985).
210. Cuishanbir et al. *Science* 233:1192 (1986).
211. Goud et al *Virology* 163:251 (1988).
212. Scheinberg and Strand *Cancer Research* 42:44 (1982).
213. Shiku et al. *J Exp Med* 144:873 (1976).
214. Boulianne,G. L., Hozumi, N., Shulman, M. J., Nature (London), 312:643 (1884).
215. Neuberger, M. S., et al., Nature (London) 314: 268 (1985).
217. Verhoeyen, M. Milstein, C., Winter, G., Reshaping Human Antibodies: Grafting an Antilysozyme Activity, Science 239:1544–6 (1988).
218. Riechmond, L., Clark, M. R., Waldmann, H., Winter, G., Reshaping Human Antibodies for Therapy, Nature 332:323–27 (1990).

What is claimed is:

1. An antibody or antigen-binding fragment thereof, other than murine monoclonal antibody M195 (ATCC No. HB 10306), comprising an amino acid sequence capable of specifically binding to the epitope to which monoclonal antibody M195 binds.

2. The antibody of claim 1, wherein the amino acid sequence comprises the amino acids of the hypervariable regions of monoclonal antibody M195 (ATCC No. HB 10306) necessary for binding to the epitope.

3. The antibody of claim 2, wherein the amino acid sequence of the hypervariable regions is the same as the amino acid sequence of the hypervariable regions of monoclonal antibody M195 (ATCC No. HB 10306).

4. The antibody of claim 3, wherein the antibody further comprises a human immunoglobulin constant region.

5. The antibody of claim 4, which antibody is a humanized antibody.

6. The antibody of claim 5, which antibody is a dimeric antibody comprising two intact antibodies linked together.

7. A therapeutic agent which comprises the antibody of claim 5 and a cytotoxic agent conjugated thereto.

8. A pharmaceutical composition which comprises an amount of the therapeutic agent of claim 7 effective to treat leukemia and a pharmaceutically acceptable carrier.

9. The therapeutic agent of claim 7, wherein the cytotoxic agent is a toxin.

10. The therapeutic agent of claim 9, wherein the toxin is a polypeptide.

11. The therapeutic agent of claim 10, wherein the polypeptide is ricin.

12. The therapeutic agent of claim 7, wherein the cytotoxic agent is an alpha particle emitter.

13. The therapeutic agent of claim 12, wherein the alpha particle emitter is selected from the group consisting of Lead-212, Bismuth-212 and Astatine-212.

14. The therapeutic agent of claim 7, wherein the cytotoxic agent is a beta particle emitter.

15. The therapeutic agent of claim 14, wherein the beta particle emitter is selected from the group consisting of Iodine-131, Scandium-47, Rhenium-186, Rhenium-188 and Yttrium-90.

16. The therapeutic agent of claim 14, wherein the beta particle emitter is Iodine-131.

17. The therapeutic agent of claim 14, wherein the beta particle emitter is Yttrium-90.

18. The therapeutic agent of claim 7, wherein the cytotoxic agent is an auger electron generator.

19. The therapeutic agent of claim 18, wherein the auger electron generator is selected from the group consisting of Iodine-123, Iodine 125, Bromine-77 and Indium-111.

20. A therapeutic agent comprising monoclonal antibody M195 (ATCC HB 10306) and a cytotoxic agent conjugated thereto.

21. The therapeutic agent of claim 20, wherein the cytotoxic agent is a toxin.

22. The therapeutic agent of claim 21, wherein the toxin is a polypeptide.

23. The therapeutic agent of claim 22, wherein the polypeptide is ricin.

24. The therapeutic agent of claim 20, wherein the cytotoxic agent is an alpha particle emitter.

25. The therapeutic agent of claim 24, wherein the alpha particle emitter is selected from the group consisting of Lead-212, Bismuth-212 and Astatine-212.

26. The therapeutic agent of claim 20, wherein the cytotoxic agent is a beta particle emitter.

27. The therapeutic agent of claim 26, wherein the beta particle emitter is selected from the group consisting of Iodine-131, Scandium-47, Rhenium-186, Rhenium-188 and Yttrium-90.

28. The therapeutic agent of claim 26, wherein the beta particle emitter is Iodine-131.

29. The therapeutic agent of claim 26, wherein the beta particle emitter is Yttrium-90.

30. The therapeutic agent of claim 20, wherein the cytotoxic agent is an auger electron generator.

31. The therapeutic agent of claim 30, wherein the auger electron generator is selected from the group consisting of Iodine-123, Iodine 125, Bromine-77 and Indium-111.

* * * * *